United States Patent
Ghosh et al.

(10) Patent No.: US 10,954,300 B2
(45) Date of Patent: Mar. 23, 2021

(54) USE OF PENTOXIFYLLINE WITH IMMUNE CHECKPOINT-BLOCKADE THERAPIES FOR THE TREATMENT OF MELANOMA

(71) Applicants: Sankar Ghosh, New York, NY (US); Yenkel Grinberg-Bleyer, New York, NY (US)

(72) Inventors: Sankar Ghosh, New York, NY (US); Yenkel Grinberg-Bleyer, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 15/763,995

(22) PCT Filed: Sep. 28, 2016

(86) PCT No.: PCT/US2016/054127
§ 371 (c)(1),
(2) Date: Mar. 28, 2018

(87) PCT Pub. No.: WO2017/058881
PCT Pub. Date: Apr. 6, 2017

(65) Prior Publication Data
US 2018/0319886 A1    Nov. 8, 2018

Related U.S. Application Data

(60) Provisional application No. 62/233,574, filed on Sep. 28, 2015.

(51) Int. Cl.
```
A61K 31/522    (2006.01)
A61P 35/00     (2006.01)
C07K 16/28     (2006.01)
A61K 39/395    (2006.01)
A61K 39/00     (2006.01)
```

(52) U.S. Cl.
CPC ........ C07K 16/2818 (2013.01); A61K 31/522 (2013.01); A61K 39/3955 (2013.01); A61K 39/39558 (2013.01); A61P 35/00 (2018.01); *A61K 2039/505* (2013.01); *C07K 2317/73* (2013.01); *C07K 2317/76* (2013.01)

(58) Field of Classification Search
CPC ... A61K 31/522; A61K 2300/00; A61P 35/00; C07K 16/2818
See application file for complete search history.

(56) References Cited

U.S. PATENT DOCUMENTS

| | | |
|---|---|---|
| 4,426,330 A | 1/1984 | Sears |
| 4,534,899 A | 8/1985 | Sears |
| 5,013,556 A | 5/1991 | Woodle et al. |
| 5,108,921 A | 4/1992 | Low et al. |
| 5,213,804 A | 5/1993 | Martin et al. |
| 5,227,170 A | 7/1993 | Sullivan |
| 5,264,221 A | 11/1993 | Tagawa et al. |
| 5,354,844 A | 10/1994 | Beug et al. |
| 5,356,633 A | 10/1994 | Woodle et al. |
| 5,395,619 A | 3/1995 | Zalipsky et al. |
| 5,416,016 A | 5/1995 | Low et al. |
| 5,417,978 A | 5/1995 | Tari et al. |
| 5,459,127 A | 10/1995 | Felgner et al. |
| 5,462,854 A | 10/1995 | Coassin et al. |
| 5,469,854 A | 11/1995 | Unger et al. |
| 5,512,295 A | 4/1996 | Kornberg et al. |
| 5,521,291 A | 5/1996 | Curiel et al. |
| 5,527,528 A | 6/1996 | Allen et al. |
| 5,534,259 A | 7/1996 | Zalipsky et al. |
| 5,543,152 A | 8/1996 | Webb et al. |
| 5,543,158 A | 8/1996 | Gref et al. |
| 5,547,932 A | 8/1996 | Curiel et al. |
| 5,556,948 A | 9/1996 | Tagawa et al. |
| 5,571,894 A | 11/1996 | Wels et al. |
| 5,580,575 A | 12/1996 | Unger et al. |
| 5,583,020 A | 12/1996 | Sullivan |
| 5,587,458 A | 12/1996 | King et al. |

(Continued)

FOREIGN PATENT DOCUMENTS

| | | |
|---|---|---|
| WO | 1985/02092 | 5/1985 |
| WO | 1993/16185 | 8/1993 |

OTHER PUBLICATIONS

International Search Report and Written Opinion, International Patent Application No. PCT/US16/54127, dated Dec. 19, 2016, pp. 1-9.

Dua, et al., "Antiproliferative and antiproteolytic activity of pentoxifylline in culture of B16F10 melanoma cells," Cancer Chemother Pharmacol, Aug. 2006, pp. 195-202, vol. 58, No. 2.

Joshi, et al., "Phosphodiesterase (PDE) inhibitor torbafylline (HWA448) attenuates burn-induced rat skeletal muscle proteolysis through the PDE4/cAMP/EPAC/PI3k/Akt pathway," Mol. Cell Endocrinol. Aug. 5, 2014, pp. 152-163, vol. 393, No. 1-2.

Algul, H., et al., Pancreas-specific RelA/p65 truncation increases susceptibility of acini to inflammation-associated cell death following cerulein pancreatitis, J Clin. Invest., 2007, pp. 1490-1501, vol. 117.

(Continued)

*Primary Examiner* — Theodore R. Howell
(74) *Attorney, Agent, or Firm* — Wolter Van Dyke Davis, PLLC; Timothy H. Van Dyke

(57) ABSTRACT

Methods of treating a PD-1-resistant cancer are provided and comprise administering to a subject in need thereof a therapeutically effective amount of a c-Rel inhibitor and a therapeutically effective amount of a PD-1 inhibitor. A pharmaceutical combination comprising a therapeutically effective amount of a c-Rel inhibitor, and a therapeutically effective amount of a PD-1 inhibitor is also provided. Finally, methods of treating a cancer such as a CTLA-4-resistant cancer, a CD137-resistant cancer, and an OX-4-resistant cancer are provided and comprise administering to a subject in need thereof a therapeutically effective amount of a c-Rel inhibitor and a therapeutically effective amount of a CLTA-4, CD137 or OX-4 inhibitor, respectively.

16 Claims, 26 Drawing Sheets

(56) References Cited

U.S. PATENT DOCUMENTS

| | | | |
|---|---|---|---|
| 5,591,721 | A | 1/1997 | Agrawal et al. |
| 5,595,756 | A | 1/1997 | Bally et al. |
| 5,641,870 | A | 6/1997 | Rinderknecht et al. |
| 5,869,046 | A | 2/1999 | Presta et al. |
| 6,355,276 | B1 | 3/2002 | Illum et al. |
| 7,431,943 | B1 | 10/2008 | Villa et al. |
| 8,952,016 | B2 | 2/2015 | Tung et al. |
| 9,035,050 | B2 | 5/2015 | Tung et al. |
| 2006/0193787 | A1 | 8/2006 | Feng |
| 2009/0217401 | A1* | 8/2009 | Korman ............ A61P 7/06 800/18 |
| 2010/0055116 | A1 | 3/2010 | Liou et al. |
| 2010/0273803 | A1 | 10/2010 | Grafe et al. |
| 2013/0137693 | A1 | 5/2013 | MacDonald et al. |
| 2015/0165025 | A1 | 6/2015 | Medarex et al. |
| 2015/0218109 | A1 | 8/2015 | Liou et al. |

OTHER PUBLICATIONS

Bravo-Cuellar, A., et al., Pentoxifylline and the proteasome inhibitor MG132 induce apoptosis in human leukemia U937 cells through a decrease in the expression of Bcl-2 and Bcl-XL and phosphorylation of p65, Journal of biomedical science, 2013, p. 13, vol. 20.

Callahan, M.K., et al., CTLA-4 and PD-1 Pathway Blockade: Combinations in the Clinic, Frontiers in oncology, 2014, p. 385, vol. 4.

Chen, S., et al., Combination of 4-1BB agonist and PD-1 antagonist promotes antitumor effector/memory CD8 T cells in a poorly immunogenic tumor model, Cancer immunology research, 2015, pp. 149-160, vol. 3.

Curran, M.A., et al., PD-1 and CTLA-4 combination blockade expands infiltrating T cells and reduces regulatory T and myeloid cells within B16 melanoma tumors, Proc. Natl. Acad. Sci. USA, 2010, pp. 4275-4280, vol. 107.

Grinberg-Bleyer, Y., et al, NF-KB c-Rel is crucial for the regulatory T cell immune checkpoint in cancer, Cell, 2017, pp. 1096-1108, vol. 170.

Hecht, M., et al., In vitro and in vivo effects of pentoxifylline on macrophages and lymphocytes derived from autoimmune MRL-Ipr/Ipr mice, J Leukoc Biol, 1995, pp. 242-249, vol. 57.

Isomura, I., et al., c-Rel is required for the development of thymic Foxp3+ CD4 regulatory T cells. J Exp Med, 2009, pp. 3001-3014, vol. 206.

Kleffel, S., et al., Melanoma Cell-Intrinsic PD-1 Receptor Functions Promote Tumor Growth, Cell, 2015, pp. 1242-1256, vol. 162.

Ouyang, Z., et al., Regulatory T cells in the immunotherapy of melanoma, Tumour biology: the journal of the International Society for Oncodevelopmental, Biology and Medicine, 2016, pp. 77-85, vol. 37.

Sharma, P., and Allison, J.P., Immune checkpoint targeting in cancer therapy: toward combination strategies with curative potential, Cell, 2015, pp. 205-214, vol. 161.

Shono, Y., et al., Characterization of a c-Rel inhibitor that mediates anticancer properties in hematologic malignancies by blocking NF-KB-controlled oxidative stress responses, Cancer Res., 2016, pp. 377-389, vol. 76, Issue 2.

Soligo, M., et al., CD28 costimulation regulates FOXP3 in a RelA/NF-kappaB-dependent mechanism, European journal of immunology, 2011, pp. 503-513, vol. 41.

Suresh, R., et al., Pentoxifylline functions as an adjuvant in vivo to enhance T cell immune responses by inhibiting activation-induced death, J Immunol, 2002, pp. 4262-4272, vol. 169.

Wang, et al., c-Rel is a target of pentoxifylline-mediated inhibition of T lymphocyte activation, Immunity, 1997, pp. 165-174, vol. 6.

* cited by examiner

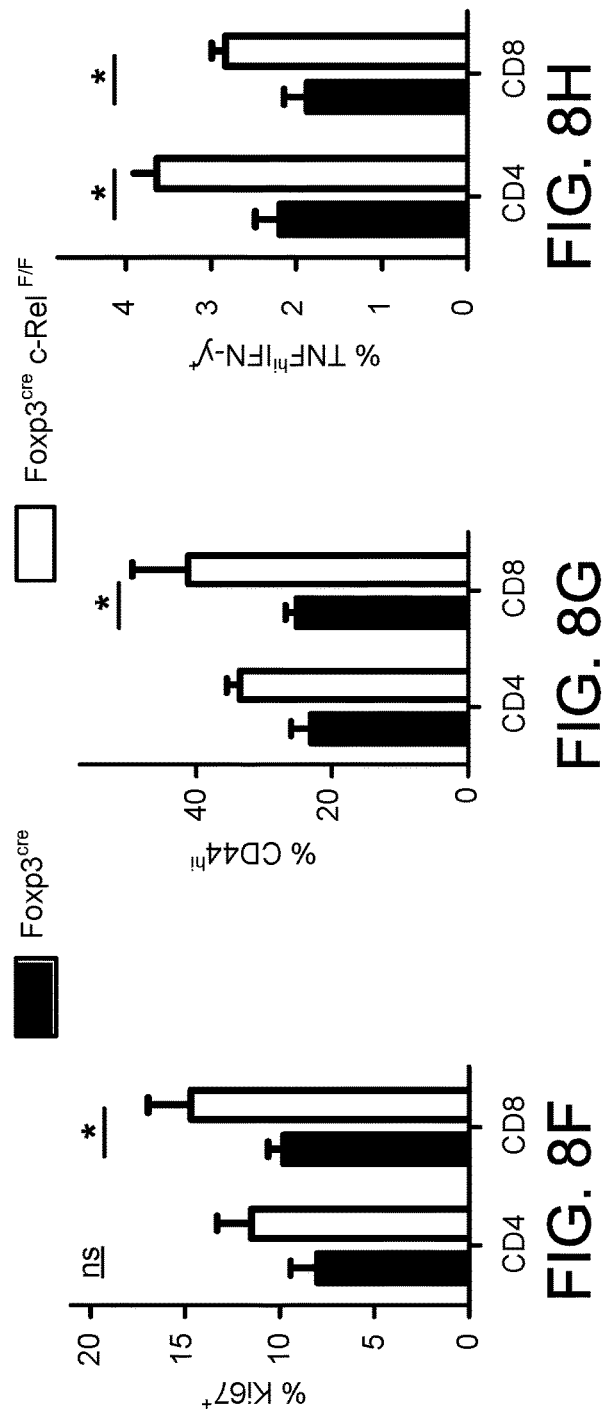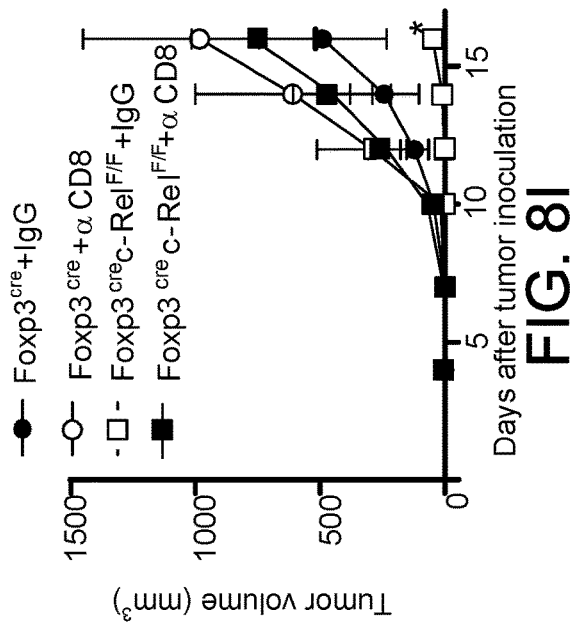

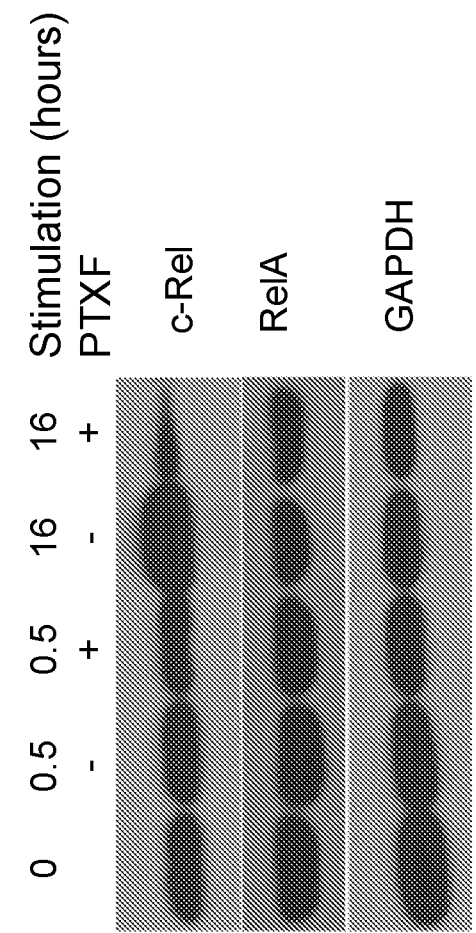
FIG. 18A
FIG. 18B
FIG. 18C
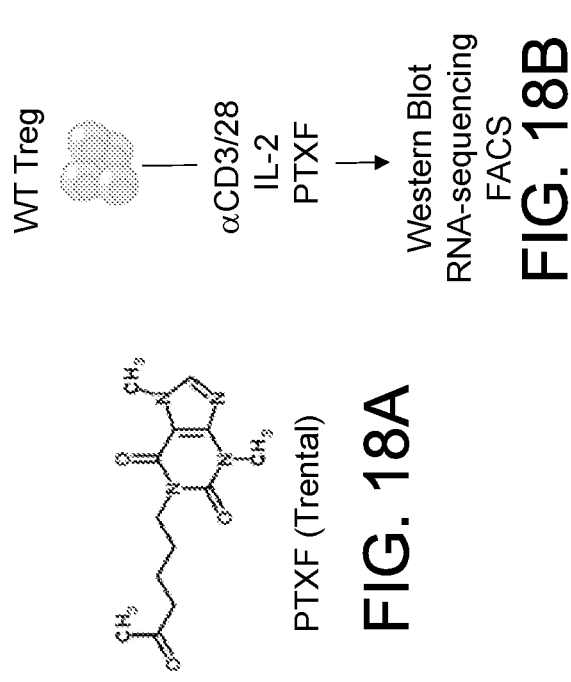
FIG. 18D
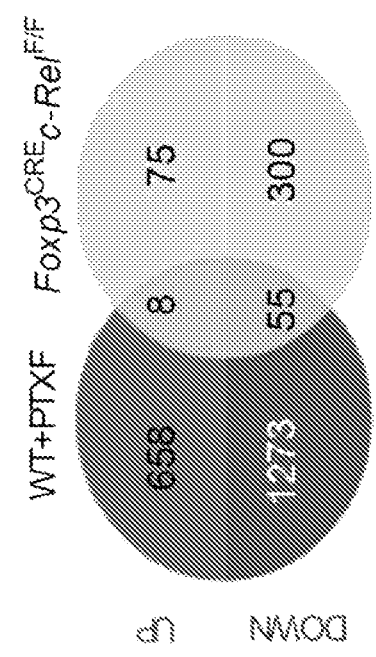
FIG. 18E
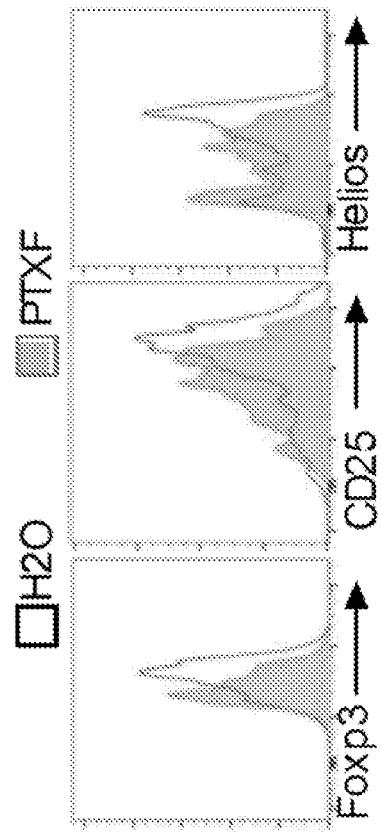

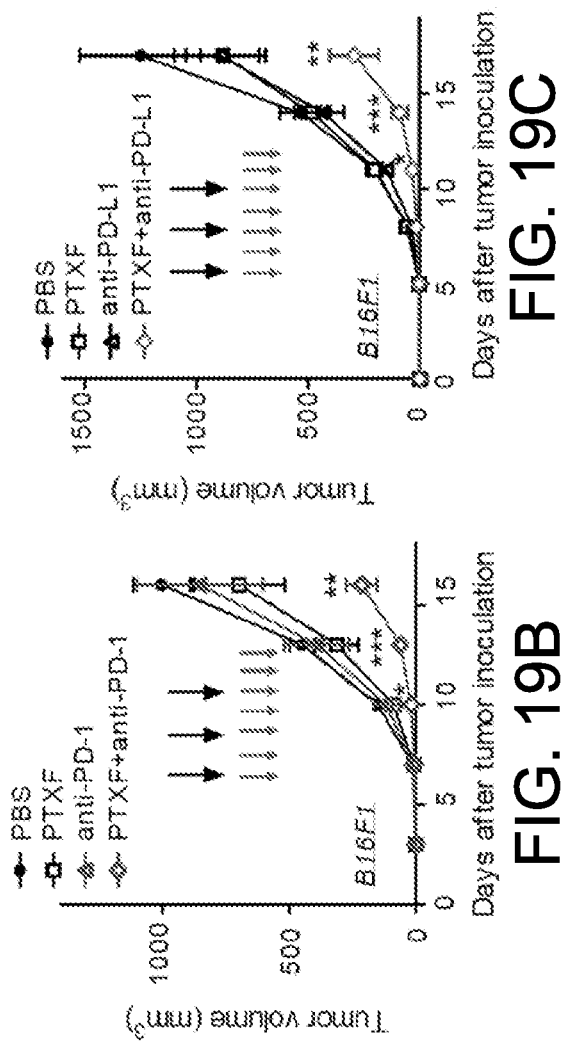
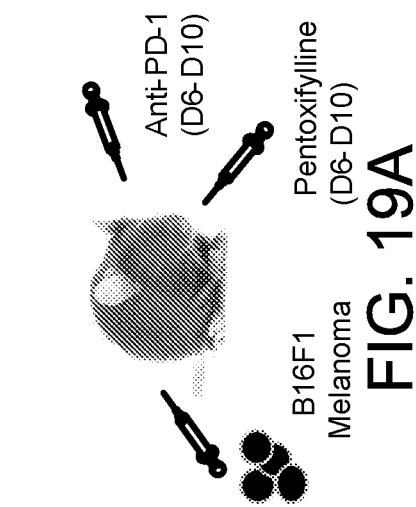
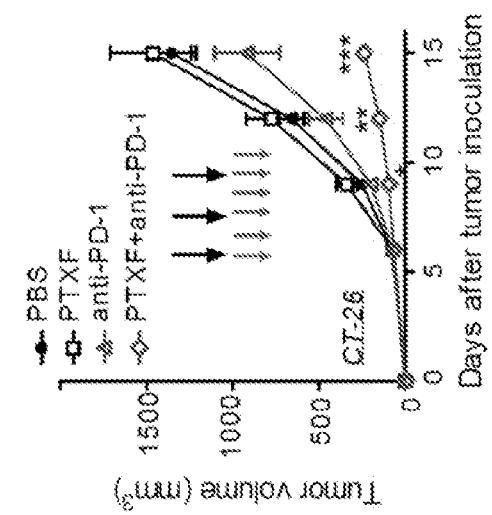
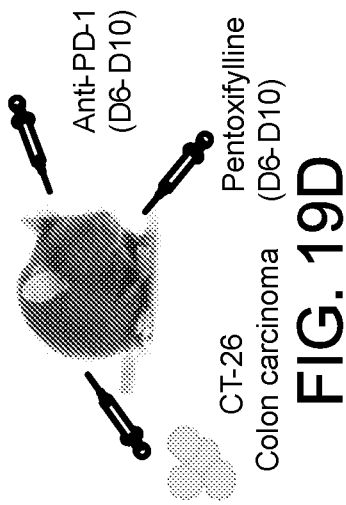
FIG. 19A, FIG. 19B, FIG. 19C, FIG. 19D, FIG. 19E

USE OF PENTOXIFYLLINE WITH IMMUNE CHECKPOINT-BLOCKADE THERAPIES FOR THE TREATMENT OF MELANOMA

CROSS-REFERENCE TO RELATED APPLICATION

The present application is a 371 national stage application of PCT Application No. PCT/US16/54127 filed Sep. 28, 2016, which claims the benefit of priority to U.S. Provisional Application No. 62/233,574, filed Sep. 28, 2015, the entire contents of which are hereby incorporated by reference in their entireties as if fully set forth herein, under 35 U.S.C. § 119(e).

STATEMENT OF GOVERNMENT INTEREST

This invention was made with government support under AI068977 a contract awarded by the National Institutes of Health. The government has certain rights in the invention.

BACKGROUND

Skin cancer is the most commonly diagnosed cancer in the United States; melanoma is the most dangerous type of skin cancer, and accounts for less than 5% of skin cancer cases but causes greater than 75% deaths of skin cancer. Malignant melanoma is a highly aggressive cancer, usually characterized by a lack of therapeutic success and eventual metastasis, with lethal result. Malignant melanoma is noted for its aggressive clinical behavior, propensity for lethal metastasis and therapeutic resistance. This clinical picture, coupled with an increase in incidence, has motivated efforts to understand the genetic underpinnings of melanoma initiation and progression and translate such insights into effective preventive and therapeutic strategies.

Melanoma, also known as malignant melanoma, is a type of cancer that develops from the pigment-containing cells known as melanocytes. Melanomas typically occur in the skin but may rarely occur in the mouth, intestines, or eye. About 25% develop from a mole with concerning changes including an increase in size, irregular edges, a change in color, itchiness, or skin breakdown. The primary cause of melanoma is ultraviolet light (UV) exposure in those with low levels of skin pigment. The UV light may be from either the sun or from tanning devices. Those with many moles, a history of affected family members, and who have poor immune function are at greater risk. A number of rare genetic defects such as xeroderma pigmentosum also increase risk. Diagnosis is by biopsy of any concerning skin lesion. In those with slightly larger cancers, nearby lymph nodes may be tested for spread. Most people are cured if spread has not occurred. In those in whom melanoma has spread, immunotherapy, biologic therapy, radiation therapy, or chemotherapy may improve survival. With treatment the five-year survival rates in the United States is 98% among those with localized disease and 17% among those in whom spread has occurred. The likelihood that it will come back or spread depends how thick the melanoma is, how fast the cells are dividing, and whether or not the overlying skin has broken down.

An increased understanding of melanocyte biology and melanoma pathogenesis has led to the development of targeted therapies which have the potential for major improvements in the care of patients with advanced melanoma. One important breakthrough is the discovery that the mitogen-activated protein kinase (MAPK) pathway drives tumorigenesis. For example, metastatic melanoma containing V600E mutations in BRAF (a protein that activates the MAPK pathway), is a highly aggressive skin cancer with poor prognosis. This mutation is found in around 50% of melanomas. Targeting activated BRAF V600E with vemurafenib leads to dramatic and rapid tumor regression. However, the drawback of this treatment is the acquired resistance arising from mutations that bypass the requirement for activated BRAF V600E in MAPK signaling. Additionally, there is currently no effective therapy for the 15-20% of melanomas with activated NRAS or other commonly known mutations.

Alternative FDA-approved therapies for disseminated melanomas include immune modulators such as IL-2 and anti-CTLA-4 (Ipilimumab), which are administered at high dose, and the B-Raf enzyme inhibitor Vemurafenib (marketed as Zelboraf). Other therapies for use in melanoma treatment include Tafinlar (dabrafenib) and Mekinist (trametinib), a MEK inhibitor. The therapeutic antibody Yervoy (ipilimumab) is also described for use in stimulating a patient's immune response. The vast majority of the responses to these regimens are partial and even good responses are often followed by relapses in which the recurring tumor has acquired substantial resistance to the therapy. Thus, the reported poor response of the combination of chemotherapy and immunomodulators, or using two or more anticancer drugs to treat metastatic melanomas in patients, underscores a need to develop new compounds for treatment of melanoma. Thus there is a need for alternative therapies for this disease.

SUMMARY

Therefore, the invention provides a method of treating a PD-1-resistant cancer comprising administering to a subject in need thereof a therapeutically effective amount of a c-Rel inhibitor and a therapeutically effective amount of a PD-1 inhibitor. The c-Rel inhibitor preferably is a herein-described active agent, and most preferably is a member selected from the group consisting of pentoxifylline, a pentoxifylline analog, dehydroxymethylepoxyquinomicin (DHMEQ), pyrimidinetrione and its derivatives including IT-603, and any combination thereof. In certain embodiments, the pentoxifylline analog is selected from the group consisting of lisofylline, torbafylline, propentafylline, A81-138, IT-603, dyfylline, doxofylline, theophylline, isobutyl methylxanthine (IBMX), caffeine, and any combination thereof, and most preferably is selected from the group consisting of torbafylline, propentafylline, A81-138, and any combination thereof.

Further, preferred embodiments of the invention are those wherein the PD-1 inhibitor is an anti-PD-1 antibody or an anti-PDL-1 antibody or a biologically active fragment or variant thereof. Preferably, the anti-PD-1 antibody or the anti-PDL-1 antibody is a humanized monoclonal antibody.

In some method embodiments as described herein, the effective amounts of the c-Rel inhibitor and the PD-1 inhibitor are about 0.1 mg/day to about 5 g/day. Preferably, the effective amount of the c-Rel inhibitor is about 400 mg/day to about 1800 mg/day and the amount of the PD-1 inhibitor is about 1 mg/kg/2 weeks to about 10 mg/kg/week. In some preferred embodiments, the effective amount of the c-Rel inhibitor is about 0.5 mg/day to about 2500 mg/day, about 1 mg/day to about 750 mg/day, about 5 mg to about 500 mg/day or about 10 mg/day to about 100 mg/day. In other preferred embodiments, the effective amount of the c-Rel inhibitor is about 2500 mg/day, about 2400 mg/day, about 2000 mg/day, about 1800 mg/day, about 1600 mg/day, about 1200 mg/day, about 1000 mg/day, about 800 mg/day, about 600 mg/day, about 500 mg/day, about 400 mg/day, about 200 mg/day, about 100 mg/day, about 50 mg/day, about 25 mg/day, about 10 mg/day, about 5 mg/day, or between about 1 mg/day and 200 mg/day.

In some preferred embodiments, the effective amount of the PD-1 inhibitor is about 1 mg/kg, about 2 mg/kg, about 5 mg/kg, about 7.5 mg/kg, or about 10 mg/kg, administered every week or every two weeks. In particular embodiments, the effective amount of the PD-1 inhibitor is about 200 micrograms, given every 2-3 days by injection.

In preferred methods, the PD-1-resistant cancer is a melanoma; most preferably wherein the melanoma is a B16F1 melanoma or a B16F10 metastatic melanoma. In other preferred embodiments, PD-1-resistant cancer is selected from the group consisting of melanoma, metastatic melanoma, ovarian cancer, fibrosarcoma, breast cancer, lung cancer, non-small cell carcinoma, and colon cancer, however specific PD-1-resistant cancers preferable are selected from the group consisting of B16F1 (melanoma), B16F10 (metastatic melanoma), Id8 (ovarian cancer), Sa1N (fibrosarcoma), TUBO (mammary carcinoma), TC-1 (lung sarcoma), BRaf$^{CA}$, Pten$^{loxP}$, Tyr::CreER$^{T2}$ (melanoma), MC38 (colon carcinoma), and CT-26 (colon carcinoma).

In other embodiments, the invention comprises a pharmaceutical combination comprising a therapeutically effective amount of a c-Rel inhibitor, and a therapeutically effective amount of a PD-1 inhibitor. Preferably, the c-Rel inhibitor is a herein described active agent, for example a member selected from the group consisting of pentoxifylline, a pentoxifylline analog, IT-603, and any combination thereof. In preferred embodiments, the pentoxifylline analog is selected from the group consisting of lisofylline, torbafylline, propentafylline, A81-138, IT-603, dyfylline, doxofylline, theophylline, isobutyl methylxanthine (IBMX), caffeine, and any combination thereof, or more preferably the pentoxifylline analog is selected from the group consisting of torbafylline, propentafylline, A81-138, and any combination thereof.

In suitable pharmaceutical combinations, the therapeutically effective amount of the c-Rel inhibitor and the therapeutically effective amount PD-1 inhibitor each are about 0.1 mg to about 5 g. Preferably, the therapeutically effective amount of the c-Rel inhibitor and the therapeutically effective amount PD-1 inhibitor each are about 400 mg to about 1800 mg.

In certain embodiments, the PD-1 inhibitor is an anti-PD-1 antibody, an anti-PDL-1 antibody or a biologically active fragment or variant thereof. Preferably, the anti-PD-1 antibody or anti-PDL-1 antibody is a monoclonal antibody, most preferably a humanized anti-PD-1 monoclonal antibody.

Other embodiments of the invention include a method of treating a cancer selected from the group consisting of a CTLA-4-resistant cancer, a CD137-resistant cancer, and an OX-4-resistant cancer comprising administering to a subject in need thereof a therapeutically effective amount of a c-Rel inhibitor and a therapeutically effective amount of a CLTA-4, CD137 or OX-4 inhibitor, respectively. Preferably, in such embodiments, the CLTA-4 inhibitor is anti-CTLA-4 monoclonal antibody, the CD137 inhibitor is anti-CD137 monoclonal antibody and the OX-4 inhibitor is anti-OX-40 monoclonal antibody.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 7A-7B. Thymuses from 5-7 weeks-old CD4cre mice crossed to mice bearing floxed alleles of p65 and c-Rel, were analyzed by flow cytometry. (FIG. 7A) Representative dot plots of gated live CD4+CD8− Foxp3− (top) and live CD4+CD8− cells (bottom). Numbers (inset) indicate the percentage of cells in each gate. (FIG. 7B) Absolute numbers of CD4+CD8−Foxp3−CD25+GITR+ Treg precursors (left) and CD4+CD8−Foxp3+ Treg cells. (FIG. 7C) CD4+CD8−Foxp3RFP−CD25+GITR+ cells were FACS-sorted from Foxp3RFP ("WT") and Foxp3RFPp65F/Fc−Rel$^{F/F}$ thymuses, treated with TAT-CRE and cultured with IL-2 for 2 days before analysis. Graph shows the % of Foxp3+CD25+ Treg in gated live cells. (FIG. 7D-7F) FACS analysis of lymphoid tissues of mice described in (FIG. 7A). (FIG. 7D) Representative Foxp3 expression in gated live TCR-b+CD4+CD8−. Numbers indicate the percentage in the gate. (FIG. 7E, FIG. 7F) percentage (FIG. 7E) and absolute numbers of TCR-b+CD4+CD8−Foxp3+ Treg cells (FIG. 7F). (FIG. 7G) CD4+CD25−CD44 low naïve T cells were sorted from the LN of indicated mice and stimulated with grading doses of hTGF-b. Graph shows the percentage of Foxp3+ among CD4+ cells after 4 days. In FIGS. 7B, 7C, 7E and 7F, data are represented as mean+/−SEM of at least 3 experiments (n=4-10 mice/group). *$p<0.05$, $p<0.01$, *$p<0.001$, n.s. non-significant.

FIG. 8A-FIG. 8I are graphs illustrating how Rel expression in Treg cells restricts anti-tumor immune responses. (FIG. 8A-FIG. 8B, FIG. 8D, FIG. 8F-FIG. 8H) 5-7 weeks-old Foxp3cre, Foxp3crep65F/F, and Foxp3crec-RelF/F were transplanted subcutaneously with B16F1 cells. (FIG. 8A) Tumor growth over time. Numbers indicate the number of mice with detectable tumors at the end of the experiment. (FIG. 8B) Representative expression of Foxp3 and % of Foxp3+ Treg cells in gated CD45+TCR-b+CD4+ cells at D16. (FIG. 8C, FIG. 8E) Splenic CD4+ Foxp3YFP+ Treg cells of each genotype were isolated, stimulated or not for 3 hours, and submitted to RNA-seq analysis. (FIG. 8C) Fold Change in the expression of selected genes is shown. (FIG. 8F) The log 2 fold change expression values for genes that were differentially expressed (p-value 27<0.01) in both c-RelF/F vs WT Treg cells and CD62LlowCD44hi (activated) vs CD62LhiCD44low (resting) WT Treg cells (public data, from (Luo et al., 2016)). (FIG. 8D, FIG. 8F-FIG. 8H) Splenocytes were restimulated ex-vivo with PMA and ionomycin 16 (D) or 4 (FIG. 8F-FIG. 8H) days after tumor inoculation. (FIG. 8D) Representative expression and cumulative % of Helios+ and IFN-γ+ in gated Treg cells (FIG. 8F-FIG. 8H). Proportion of Ki67+ (F), CD44high (FIG. 8G) and $TNF^{high}IFN-\gamma$ (FIG. 8H) cells in CD45+TCRα+CD4+ Foxp3− and CD8+ cells is shown (n=4 mice/group). (FIG. 8I) The indicated mice were transplanted as in (FIG. 8A) and were injected at D0 and D3 with anti-CD8 or IgG isotype control. Tumor growth over time is shown (n=3-8 mice/group). All data are represented as mean+/−SEM of at least 3 experiments. $*p<0.05$, $p<0.01$, $*p<0.001$, n.s. non-significant.

FIG. 9A-FIG. 9B. CD4+ GFP+ Treg cells were sorted form Foxp3eGFP spleens, and stimulated with anti-CD3/CD28 and mIL-2 in the presence of 500 □g/ml PTXF or H2O as a control. (FIG. 9A) Western Blot on total cell lysates at the indicated times (B) Flow cytometry after 16 h stimulation. Data are representative histograms on gated live CD4+ cells. (FIG. 9C, 9D) CD4+ YFP+Treg cells were sorted from Foxp3cre (WT) and Foxp3crerelF/F were activated as in FIG. 9B and submitted to RNA-Seq analysis. (FIG. 9C) Summary of gene expression changes. Numbers indicate the genes with a fold-change>2 and a p-value<0.05. Up: up-regulated expression when compared to the WT control cells; down: down-regulated expression. (FIG. 9D) Heatmap showing the fold-changes of selected genes in each condition. (FIG. 9E-FIG. 9G) CD4+GFP+ Treg cells were stimulated as in FIG. 9B and subsequently tested for in vitro suppression (FIG. 9E) and in vivo colitis assays (FIG. 9F, FIG. 9G). (FIG. 9E) Suppression of responder T cells proliferation. (FIG. 9F) Weight changes upon cell transfer, shown as % of the initial weight at D0 (n=5 mice/group). (FIG. 9G) Total colon length at D35 after transfer. In FIG. 9A and FIG. 9B, data are from one out of 4 experiments with similar results. In D, values are the mean of 2 samples/group. In FIG. 9E-FIG. 9G, data are represented as mean+/−SEM of at least 2 experiments. $*p<0.05$, $p<0.01$, $*p<0.001$, n.s. non-significant.

FIG. 10A-FIG. 10D. WT C57Bl/6J mice were transplanted sub-cutaneously with B16F1 cells and treated from D-1 to D7 with PTXF or PBS as a control. (FIG. 10A) Tumor growth over time (n=9 mice/group). Arrows indicate the days of PTXF or PBS injection. (FIG. 10B-FIG. 10F) TILS were restimulated ex-vivo with PMA and ionomycin 16 days after tumor inoculation. (FIG. 10B) % of Foxp3+ Treg cells in gated CD45+TCR-β+CD4+ cells at D16. (FIG. 10C) Phenotype of gated Treg cells at D16. (FIG. 10D) Representative IFN-expression in CD8+ T cells. (FIG. 10E) Cumulative % of IFN-+ T cells (3-4 mice/group).

(FIG. 10F) qPCR analysis on total tumor RNA at D16 (n=5 mice/group). (FIG. 10G) RAG1−/− mice were transplanted and treated as in FIG. 10A. Tumor growth over time is shown (n=7/group). (FIG. 10H) WT C57Bl/6J mice were injected intravenously with B16F10 cells and with PTXF or PBS from D-1 to D7. The number of macroscopic tumor foci is showed. Data are represented as mean+/−SEM of 3 (FIG. 10A-FIG. 10G) or 2 (FIG. 10H) experiments. $*p<0.05$, $***p<0.001$.

(FIG. 11A-FIG. 11B) WT C57Bl/6J mice were transplanted sub-cutaneously with B16F1 cells and treated from D6 with PTXF or anti-PD-1 mAb or PBS. (FIG. 11A) Tumor growth over time (n=6-10 mice/group); red arrows: PTXF injections, black: anti-PD-1 injections. (FIG. 11B-FIG. 11C) TILS were restimulated ex-vivo with PMA and ionomycin 16 days after tumor inoculation. (FIG. 11B) Representative IFN-expression in CD8+ T cells. (FIG. 11C) Cumulative % of IFN-©+ T cells (3-5 mice/group). The statistics compare the PBS vs PCTF+anti-PD-1 groups; others are non-significant. (FIG. 9D) qPCR analysis on total tumor RNA at D16 (4 mice/group). (FIG. 9E) Mice were treated as in A and were injected with anti-CD8 mAb or IgG at D7 and 9 (blue arrows). Tumor growth over time is shown (n=8 mice/group). (FIG. 9F) Mice were treated as in A but with anti-PD-L1 mAb instead of anti-PD-1. Tumor growth over time is shown (n=6-8 mice/group). (FIG. 9G) WT Balb/C mice were transplanted sub-cutaneously with CT-26 cells 29 and treated from D6 with PTXF or anti-PD-1 mAb (500 □g) or PBS. Tumor growth over time is shown (n=6-10 mice/group); red arrows: PTXF injections, black: anti-PD-1 injections. Data are represented as mean+/−SEM of 3 to 4 experiments. $*p<0.05$, $***p<0.001$.

(FIG. 12A). Western blot on purified splenic CD4+ cells. (FIG. 12A-FIG. 12D) Thymuses (FIG. 12B-FIG. 12C) and tissues (FIG. 12D) from 6-8 weeks old. CD4cre, CD4crep65F/F, CD4crec-RelF/F and CD4crep65F/Fc-RelF/F F were analyzed by flow cytometry. (FIG. 12C-FIG. 12D) % of Foxp3+ Treg cells in gated TCR-b+CD4+CD8− in the indicated tissues. Data are represented as mean+/−SEM of at least 2 experiments (n=2-10 mice/group). $*p<0.05$, $p<0.01$, $*p<0.001$, n.s. non-significant.

(FIG. 13A) Splenic CD4+Foxp3YFP+ Treg cells of each genotype were isolated, stimulated or not for 3 hours, and submitted to RNA-seq analysis. The set of 688 genes changed solely in Rel-deficient Treg was submitted to GSEA analysis (C7 ImmunoSigDB). A representative enrichment plot is shown, demonstrating the loss of Treg-associated molecules. (FIG. 13B) 5-7 weeks-old Foxp3cre and Foxp3crerelF/F were transplanted sub-cutaneously with B16F1 cells. Splenocytes were restimulated ex-vivo with gp100/pmel peptide, 4 days after tumor inoculation. Representative dot plot of IFN-expression in gated TCR-b+CD8+ cells. Numbers indicate the percentage in the gate; MFI: Mean Fluorescence Intensity of IFN-in IFN-cells. (FIG. 13C) Foxp3cre and Foxp3crerelF/F were injected intravenously with B16F10 cells. Left: representative picture of lungs at D14; right: Number of detectable tumor foci/lung at D14. Each dot represents an individual mouse form 2 independent experiments. (FIG. 13D) Foxp3cre and Foxp3crerelF/F were transplanted sub-cutaneously with $BRAF^{CA}Pten^{-/-}$ cells. The mean+/−SEM of tumor growth over time is shown (n=7-8 mice from 2 3 independent experiments). Numbers indicate the number of mice with detectable tumors at the end of the experiment. ***p<0.001.

(FIG. 14A) Summary of gene expression changes in WT Treg treated with PTXF and Foxp3crep65F/F, compared to WT+H2O Treg cells. Numbers indicate the genes with a fold-change>2 and a p-value<0.05. Up: up-regulated expression when compared to the WT control cells; down: down-regulated expression. (FIG. 14B-(FIG. 14D) CD4+GFP+ Treg cells were stimulated as in FIG. 14A and subsequently tested for in vitro suppression (FIG. 14B) and in vivo colitis assays (FIG. 14C, FIG. 14D). (FIG. 14B) Percentage of donor CD45.2+ Treg cells in each well. (FIG. 14C) Colon histology (H/E) 40 days after cell transfer; bars: 100 µm, original magnification 100x. (FIG. 14D) Tissues were analyzed by flow cytometry 40 days after cell transfer. The proportion of Foxp3+ Treg cells in live CD45+TCR-β+CD4+ is shown. In FIG. 14B and FIG. 14D, data represent the mean of 2 experiments; values were non-significantly changed between groups.

(FIG. 15C) % of CD44high in T cells. (FIG. 15D) % of Ki67+ in T cells. Data are represented as mean+/-SEM of 3 mice/group in one out of 2 experiments with similar results.

(FIG. 16A) CD4/CD8 ratio in TCR-β+ live cells. (FIG. 16B) % of CD44 high in T cells. Data are represented as mean+/-SEM of 2 experiments (3-6 mice/group). *p<0.05, n.s. non-significant.

FIG. 17A is a schematic illustrating Foxp3$^{CRE}$ rel and p65-flox mice injected with B16F1 melanoma cells. FIG. 17B is a graph showing melanoma tumor volume changes under the listed conditions where 8/8 WT mice Foxp3$^{cre}$ and 6/6 Foxp3$^{cre}$p65$^{F/F}$ mice had detectable tumor burden, whereas only 3/7 Foxp3$^{cre}$crel$^{F/F}$ mice had detectable tumor burden. Melanoma growth was reduced in mice having ablated c-Rel. FIG. 17C is a graph illustrating CD4+Foxp3$^-$ in LN and Spleen and CD8+ in LN and Spleen. FIG. 17D is a schematic showing WT Treg cells exhibit exponential growth from CD4, CD8 T cells to B16 melanoma cells and Crel-KO Treg cells showing reduced growth.

FIG. 18A-18E are schematics representing how pentoxifylline impairs c-Rel-mediated Treg homeostasis. FIG. 18A is a chemical structure of PTXF (Trental). FIG. 18B is a schematic representing experimental protocol from WT Treg cells to alpha CD3/28 IL-2 PTXF to Western Blot, RNA sequence and FACS. FIG. 18C is an image of a Western Blot showing PTXF stimulation at 0.5, and 16 hours. FIG. 18D is a schematic illustrating WT+PTXF and Foxp3$^{Cre}$c-Rel$^{F/F}$. FIG. 18E are spectra graphs illustrating Foxp3, CD25 and Helios with H$_2$O control and PTXF.

FIG. 19A-19E are schematics and graphs illustrating how pentoxifylline cooperates with checkpoint-blockade therapies to reduce tumor growth. FIG. 19A is a schematic illustrating administration of PTXF or anti-PD-1 reduced growth of melanoma.in mice subcutaneously injected with B16F1 melanoma and then injected with either control vehicle or with PTXF or anti-PD-1. FIG. 19B and FIG. 19C are graphs showing melanoma tumor volume changes under the listed conditions. FIG. 19D is a schematic illustrating administration of PTXF and anti-PD-1 reduced growth of melanoma in mice that were subcutaneously injected with CT-26 colon carcinoma cells and then injected with either anti-PD-1 or PTXF. FIG. 19E is a graph showing colon tumor changes under the listed conditions.

DETAILED DESCRIPTION

Figure 1:
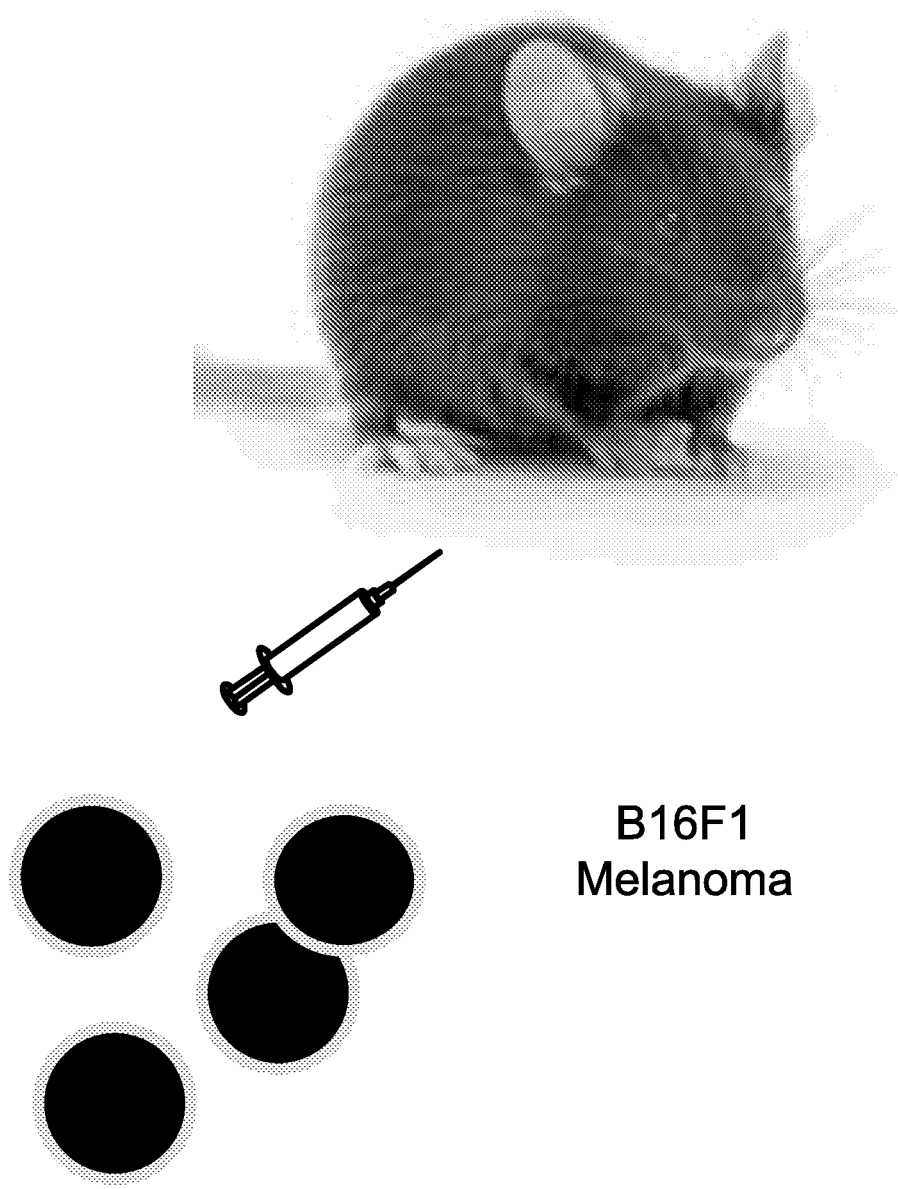
FIG. 1 is a schematic showing how ablation of c-Rel in mice drastically reduced B16F1 melanoma growth in vivo while ablation of p65 did not.

The role of NF-κB in Tregs and its effect on tumor growth was tested here. The present invention is based on the discovery that administering the FDA-approved drug pentoxifylline (PTXF), which targets the c-Rel subunit of NF-κB, together with anti-PD-1 (Programmed Death 1 protein) monoclonal antibodies (mAb) almost completely suppressed B16F1 melanoma tumor growth in an in vivo mouse model. Both drugs show low toxicity in clinical trials. Alternatively, an anti-PDL-1 antibody can be used in place of the anti-PD-1 antibody.

Tumors employ a wide variety of strategies to grow, metastasize, and avoid recognition and elimination by the immune system (Dunn et al., 2002). One of the major mechanisms of tumor immune evasion is the engagement of immunosuppressive receptors on effector T-cells such as PD-1 and CTLA-4 by their ligands expressed within tumors. The common goal of emerging cancer immunotherapies is to break tumor tolerance and promote a productive anti-tumor immune response. While the use of immune checkpoint blockade therapies is revolutionizing cancer care (Sharma and Allison, 2015), there are a significant number of tumors that do not benefit from such approaches alone. One possible mechanism to explain resistance to existing checkpoint blockade is that other immunosuppressive mechanisms are engaged in such tumors e.g. through influx of immune inhibitory cells. CD4$^+$Foxp3$^{+regulatory}$ T cells (Treg cells) have been shown to play an essential role in the suppression of anti-tumor responses (Nishikawa and Sakaguchi, 2010; Onizuka et al., 1999; Tang and Bluestone, 2008). Treg cells are known to be highly enriched in lesions of patients with melanoma (Jandus et al., 2008; Ouyang et al., 2016) and their presence correlates with poor prognosis (Baumgartner et al., 2009).

Accordingly, one embodiment provided herein is a method of treating a PD-1-resistant cancer comprising administering to a subject in need thereof a therapeutically effective amount of a c-Rel inhibitor and a therapeutically effective amount of a PD-1 inhibitor. The c-Rel inhibitor preferably is a herein-described active agent, and most preferably is a member selected from the group consisting of pentoxifylline, a pentoxifylline analog, dehydroxymethyl-epoxyquinomicin (DHMEQ), pyrimidinetrione and its derivatives including IT-603, and any combination thereof. In certain embodiments, the pentoxifylline analog is selected from the group consisting of lisofylline, torbafylline, propentafylline, A81-138, IT-603, dyfylline, doxofylline, theophylline, isobutyl methylxanthine (IBMX), caffeine, and any combination thereof, and most preferably is selected from the group consisting of torbafylline, propentafylline, A81-138, and any combination thereof.

Further, in specific embodiments, the PD-1 inhibitor is an anti-PD-1 antibody or an anti-PDL-1 antibody or a biologically active fragment or variant thereof. In more specific embodiments, the anti-PD-1 antibody or the anti-PDL-1 antibody is a humanized monoclonal antibody.

1. Definitions

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques of the present invention generally are performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Immunoscience, 4th ed., Eric R. Kandel, James H. Schwartz, Thomas M. Jessell editors. McGraw-Hill/Appleton & Lange: New York, N. Y. (2000). Unless defined otherwise, all technical and scientific terms used herein have the same meaning as commonly understood by one of ordinary skill in the art.

"NF-κB (nuclear factor kappa-light-chain-enhancer of activated B cells)" refers to a protein complex that controls transcription of DNA, cytokine production and cell survival. NF-κB is found in almost all animal cell types and plays a key role in regulating the immune response to infection. Incorrect regulation of NF-κB has been linked to numerous diseases, including cancer. NF-κB belongs to the category of "rapid-acting" primary transcription factors, i.e., transcription factors that are present in cells in an inactive state and do not require new protein synthesis in order to become activated. All proteins of the NF-κB family share a Rel homology domain in their N-terminus. A subfamily of NF-κB proteins, including RelA, RelB, and c-Rel, has a transactivation domain in their C-termini.

"c-Rel" refers to the proto-oncogene protein member of the NF-κB family of transcription factors that in humans is encoded by the REL gene. The c-Rel protein contains a Rel homology domain (RHD) at its N-terminus and two C-terminal transactivation domains. C-Rel has an important role in B-cell survival and proliferation. The REL gene is amplified or mutated in several human B-cell lymphomas, including diffuse large B-cell lymphoma and Hodgkin's lymphoma.

"Pentoxifylline (PTXF)" refers to the phosphodiesterase inhibitor which is methylxanthine derivative 1-(5-oxohexyl)-3,7-dimethylxanthine. PTXF is a specific c-Rel inhibitor that reduces the levels of c-Rel activation in T cells in vitro, while leaving the levels of p65 unchanged. PTXF also raises intracellular cAMP, activates PKA, and reduces inflammation. Pentoxifylline is also known under the brand names Trental®, Pentox®, Pentoxil® and Flexital®). PTXF has previously been described as an anti-cancer drug. The anti-cancer properties of PTXF have been attributed to reduced expression of adhesion molecules or direct induction of apoptosis in cancer cells (Bravo-Cuellar et al., 2013; Edward and MacKie, 1991). However, the role of the immune system in the anti-tumor effects of PTXF was unexplored.

"Enumerated disease" refers to a PD-1 resistant cancer, a CTLA-4-resistant cancer, a CD137-resistant cancer, or an OX-4-resistant cancer. Examples of PD-1-resistant cancers include, but are not limited to, melanoma, metastatic melanoma, ovarian cancer, fibrosarcoma, breast cancer, lung cancer, non-small cell carcinoma, and colon cancer. More specific examples of PD-1-resistant cancers pertain to B16F1 (melanoma), B16F10 (metastatic melanoma), Id8 (ovarian cancer), Sa1N (fibrosarcoma), TUBO (mammary carcinoma), TC-1 (lung sarcoma), $BRaf^{CA}$, $Pten^{loxP}$, Tyr::$CreER^{T2}$ (melanoma), MC38 (colon carcinoma), and CT-26 (colon carcinoma).

"Programmed cell death protein 1 (PD-1)" refers to a protein that in humans is encoded by the PDCD1 gene. PD-1 is a cell surface receptor that belongs to the immunoglobulin superfamily and is expressed on T cells and pro-B cells bearing two ligands, PD-L1 and PD-L2. PD-1 functions as an immune checkpoint, playing an important role in down-regulating the immune system by preventing the activation of T-cells, which in turn reduces autoimmunity and promotes self-tolerance. The inhibitory effect of PD-1 is accomplished through a dual mechanism of promoting apoptosis (programmed cell death) in antigen-specific T-cells in lymph nodes while simultaneously reducing apoptosis in regulatory T cells (suppressor T cells). PD-1 is a type I membrane protein of 268 amino acids that is a member of the extended CD28/CTLA-4 family of T cell regulators.

"PD-1 inhibitors" refers to a class of drugs that activate the immune system to attack tumors by blocking or reducing the activity of PD-1 protein.

"PD-L1 and PD-L2" refers to two protein ligands of PD-1, which are members of the B7 family. PD-L1 protein is upregulated on macrophages and dendritic cells (DC) in response to LPS and GM-CSF treatment, and on T cells and B cells upon TCR and B cell receptor signaling. PD-1 negatively regulates T cell responses is expressed on almost all murine tumor cell lines, including PA1 myeloma, P815 mastocytoma, and B16 melanoma upon treatment with IFN-γ. PD-L2 expression is more restricted and is expressed mainly by dendritic cells and a few tumor lines.

"Regulatory T cells (Tregs)" refers to cells, formerly known as suppressor T cells, that are a subpopulation of T cells which modulate the immune system, maintain tolerance to self-antigens, and abrogate autoimmune disease. These cells generally suppress or downregulate induction and proliferation of effector T cells.

2. Overview

The immune system is a carefully balanced system with tight regulation of immune cell function. When the balance is disrupted, it can lead to disease. CD4+ T cells recognize peptide-major histocompatibility complex (MHC) class II complexes presented by antigen-presenting presenting cells (APCs) and differentiate into different effector T-cell subtypes or regulatory T cells upon activation. Among CD4+ T-helper cells, Th1 cells are responsible for immunity against intracellular pathogens primarily through secretion of interferon-γ (IFN-γ), whereas Th2 cells promote the humoral immune response against extracellular pathogens through secretion of interleukin-4 (IL-4) and other cytokines.

Cancers use a wide variety of mechanisms to dampen immune responses. Among them, CD4+Foxp3+ regulatory T cells (Tregs) play a major role in inhibiting the function of effector cells. In several models of cancer, Treg depletion suppresses tumor growth. Therefore, understanding the mechanisms governing Treg homeostasis is a valuable strategy to enhance immune responses against cancer.

Treg cells help maintain immune homeostasis in various settings including in response to commensal microbiota or food allergens at mucosal surfaces. Treg cells also suppress experimental graft-versus-host disease (GvHD) in mice, leading to the exploration of Treg modulation as a potential therapeutic targeting strategy. On the other hand, altered Treg function in some cancers facilitates immune evasion, thereby promoting the exploration of alternative approaches toward cancer immunotherapies. Because Treg cells are important in many immune disorders, it has been a major interest to study how Treg cells differentiate and function.

In the thymus, CD4+ and CD8+ T cells develop from thymocytes. Naive CD4+ T cells from the thymus migrate to the periphery, where they can differentiate into various subsets of effector cells upon encountering specific antigens. A small population of thymocytes differentiates into regulatory T cells (nTreg) in the thymus. In addition, some naive CD4+ T cells differentiate into regulatory T cells (iTreg) in specific microenvironments.

Treg cells are classified into two major classes based on their developmental origin. Treg cells can be generated in the thymus through the natural selection process: natural Treg (nTreg) or thymic Treg (tTreg) cells. Alternatively, conventional naive T cells can differentiate into FoxP3+ Treg cells in the periphery upon exposure to non-self-antigens such as commensal microbiota, food, or allergens. These Treg cells generated in the periphery are generally referred to as inducible Treg (iTreg) cells.

NF-kB

T cells function both as regulators and effectors of the immune response. The transcription factor NF-κB plays a major role in Treg development, activation, differentiation, and survival. Using conditional knockout mice, the role of different NF-kB subunits in Tregs during the anti-tumor immune response has been demonstrated. Both p65 (RelA) and c-Rel subunits of NF-kB are required for both development and function of Tregs. NF-κB imprints a specific molecular signature in Tregs that confers their suppressive capacity and is a key determinant in maintaining Treg identity in vivo.

The NF-κB family comprises five subunits: RelA (p65), RelB, c-Rel, NF-kB1 (p105), and NF-kB2 (p100). Each has an N-terminal Rel-homology domain that is responsible for DNA binding and homo- and hetero-dimerization. The p65, c-Rel, and RelB subunits contain a transcription activation domain and are hence capable of driving transcription. NF-kB makes distinct heterodimeric complexes, the most common of which is p50:p65, which regulates the broadest range of NF-kB target genes, including genes involved in developmental and inflammatory processes. Unfortunately, p65 inhibition is associated with high toxicity (a p65 knock-out mouse is an embryonic mortal), however, little toxicity is associated with inhibition of c-Rel, because it is more selectively expressed, in particular by adaptive immune cells.

In general, NF-κB activation occurs through two major pathways: the canonical and non-canonical pathways. In the canonical pathway, IKKbeta phosphorylation of ikbalpha leads to its degradation and the subsequent liberation of the NF-κB dimers. p65:p50 heterodimers are the major targets of the canonical pathway, but other combinations of dimers, including c-Rel containing dimers, can be involved in the pathway. In the non-canonical pathway, the NF-κB inducing kinase (NIK) (2) directly phosphorylates and activates IKKalpha. Activated IKKalpha phosphorylates p100, which results in proteosomal processing of p100 to p52. p52 forms a heterodimer with RelB and translocates to the nucleus to bind to kb-binding sites. Activation of the NF-κB pathway regulates expression of a plethora of immunomodulatory factors, including cytokines, chemokines, adhesion molecules, antimicrobial factors, cell cycle regulators, and cell survival factors.

Within the canonical pathway, NF-κB complexes containing p65 or c-Rel perform different biological roles. While p65 containing NF-κB is mainly responsible for most cellular activation responses, c-Rel containing NF-κB complexes play more specialized roles in the immune response, typically in lymphoid development. This difference is starkly illustrated in the phenotypes of mice lacking p65 or c-Rel. Deletion of p65 leads to embryonic lethality due to a dramatic defect in cell survival of hepatocytes, and cells lacking p65 show broad defects in survival, proliferation and response to different stimuli (Beg et al., 1995). In contrast c-Rel knock-outs are viable and, despite strong c-Rel expression in lymphocytes, show limited in vivo immunological defects (Kontgen et al., 1995). Hence availability of inhibitors that could target only NF-κB c-Rel would likely avoid the undesirable side-effects that have halted advancement of NF-κμ-inhibitors, e.g. IKK inhibitors, for clinical use in inflammatory diseases and cancer (DiDonato et al., 2012).

The NF-κB signaling cascade is a major transducer of external signals which controls the expression of a broad range of genes involved in survival, growth, stress response, and inflammation. See s. Ghosh et al., Immunological Reviews, Vol. 252, Page 41-52, 2013. This signaling is tightly regulated. Aberrant activation of the pathway is associated with the pathogenesis of solid tumors, leading to a rationale for the development of antitumor therapies that inhibit NF-kB signaling. However, the role of NF-κB may be more complex, and some studies indicate that inhibition of NF-kB signaling would reduce chemosensitivity rather than promoting cell death in tumors with a certain genetic make-up. Therefore, it is important to determine the context of NF-κB-mediated functions when contemplating using NF-κB inhibitors. Both p65 (RelA) and c-Rel subunits of NF-κB are required for development and function of Tregs. NF-kB imprints a specific molecular signature in Tregs that confers their suppressive capacity and is a key determinant in maintaining Treg identity in vivo.

Treg cells, that either develop in the thymus (nTreg), or are induced in the periphery (iTreg), normally represent 5-15% of the CD4+ T cell population. They can inhibit multiple aspects of the immune response through diverse mechanisms that include secretion of inhibitory cytokines, direct cytotoxicity, disruption of metabolic pathways in target cells, or by inhibiting the function of antigen-presenting cells (Tang and Bluestone, 2008; Vignali et al., 2008). The expression of the forkhead-box transcription factor Foxp3, a hallmark of Treg cells, is crucial for the acquisition of the suppression program and for the maintenance of Treg identity, and hence immune tolerance (Gavin et al., 2007; Samstein et al., 2012). Thus, understanding the molecular signals that drive Treg development and homeostasis is of the highest interest. Several studies have shown that the transcription factor NF-κB, in particular the c-Rel subunit, is crucial for the expression of FoxP3 and the thymic development of Tregs (Isomura et al., 2009; Long et al., 2009; Ruan et al., 2009). In fact mice lacking key intermediates in the TCR-induced NF-κB pathway, e.g. CARMA-1, Bcl-10 or Malt-1 also demonstrate dramatically reduced numbers of Treg cells (Isomura et al., 2009; Molinero et al., 2009).

Mice lacking any member of the CARMA-1/Bcl-10/ Malt1 complex exhibit a profound lack of Foxp3$^+$ thymocytes (Molinero et al., 2009). On the other hand, constitutive activation of NF-κB through an IKK-EE transgene in T cells increases thymic Treg cells (Long et al., 2009). Furthermore, germline deletion of c-Rel leads to reduced transition into the Treg progenitor step, and subsequent maturation into Foxp3$^+$ Treg cells (Grigoriadis et al., 2011; Isomura et al., 2009). However, deletion of c-Rel does not fully eliminate Treg cells, leaving unclear the extent of the requirement for the canonical NF-κB pathway. Furthermore, it was found that Nfkb1$^{-/-}$ mice, which lack the p50 subunit that typically heterodimerizes with c-Rel and p65, did not show any defect in Treg development (Deenick et al., 2010). The study of p65$^{-/-}$ mice was complicated by the embryonic lethality of these mice, although indirect evidence pointed towards a role for p65 in Foxp3 expression (Deenick et al., 2010; Isomura et al., 2009; Soligo et al., 2011). As presented herein, using conditional deletion of p65 and/or c-Rel in T cells, a crucial requirement was demonstrated for both canonical NF-κB subunits in the generation of Foxp3$^+$ Treg precursors.

Canonical NF-κB signaling, along with IL-2/STAT-5 and IκB-NS signals (Lio and Hsieh, 2008; Schuster et al., 2012), is crucial for the subsequent expression of Foxp3, and for mature Treg cell homeostasis in secondary lymphoid organs. This was in agreement with the observation that Foxp3 expression is driven by the formation of an "enhanceosome" at the Foxp3 locus (Ruan et al., 2009). We also showed a partial redundancy between both subunits, as absence of both p65 and c-Rel led to nearly complete abolishment of Treg cells in the thymus and the periphery.

Treg cells can also be differentiated from naïve T cells in the periphery or in vitro (iTreg cells). Although the TCR signal is required for Foxp3 expression in iTregs, only a moderate role for NF-κB was previously described in this process (Jana et al., 2009; Visekruna et al.). Moreover, in contrast to what is observed in thymocytes, aberrant NF-κB activation restricted differentiation into iTreg cells (Molinero et al., 2011). In contrast to these previous reports, naïve T cells fully lacking canonical NF-κB were shown here to be unable to give rise to iTreg, even in the presence of exogenous IL-2, while deletion of only p65 or c-Rel had nearly no effect. Thus, these studies demonstrate a redundant but crucial role for canonical NF-κB activity in iTreg development and highlight a specific role for each NF-κB subunit in Treg development in vivo and in vitro.

NF-κB inhibition may be contraindicated in genetically defined cancer subtypes in which NF-κB activation has no primary role in pro-survival, but that instead require a functional NF-κB pathway for enhancing chemosensitivity. In a mouse lymphoma model, tumors constitutively expressing Myc and Mcl2 oncogenes underwent senescence in response to cytotoxic drug therapy that activated NF-κB, and included senescence in p65-proficient but not p65-deficient lymphomas. Therefore, silencing NF-κB activity impaired the response to chemotherapy in this model, indicating that, in this context, NF-κB inhibition has an unwanted effect.

The opposing roles of NF-κB in oncogenesis, promoting tumorigenesis on the one hand and mediating therapy-induced senescence on the other hand, have significant therapeutic implications. Therefore, it is important to take into account the complexity of NF-κB signaling in cancer cells to develop specific and more effective cancer therapies.

Here, melanoma growth was drastically reduced in mice lacking c-Rel, but not p65, specifically in Treg cells. Moreover, chemical inhibition of c-Rel delayed melanoma growth and potentiated anti-PD-1 immunotherapy by impairing the Treg transcriptional program. As c-Rel inhibition has a mild effect on in vivo CD8+ T-cell responses, the studies establish inhibition of NF-κB c-Rel as a viable therapeutic approach for enhancing checkpoint targeting immunotherapy protocols.

3. Summary of Results

The specific c-Rel inhibitor pentoxifylline (PTXF), a drug widely used in the past to treat patients with claudication, reduces the levels of c-Rel activation in T cells in vitro, while leaving the levels of p65 unchanged. Wang et al., "c-Rel is a target of pentoxifylline-mediated inhibition of T lymphocyte activation." Immunity 6(2):165-174; 1997. Our results confirmed these previous results (data not shown). Ablation of c-Rel in mice drastically reduced B16F1 melanoma growth in vivo while ablation of p65 did not. See FIG. 1. Foxp3$^{CRE-YFP}$ p65, crel$^{F/F}$ mice and WT littermates were transplanted with B16F1 melanoma cells. See FIG. 1. Eight out of eight WT mice and five out of five Foxp3$^{cre}$p65$^{F/F}$ mice had detectable tumor burden, whereas only three out of seven Foxp3$^{cre}$crel$^{F/F}$ mice had detectable tumor burden. (See FIG. 2.) Thus, melanoma growth was reduced in mice having ablated c-Rel.

Figure 3:
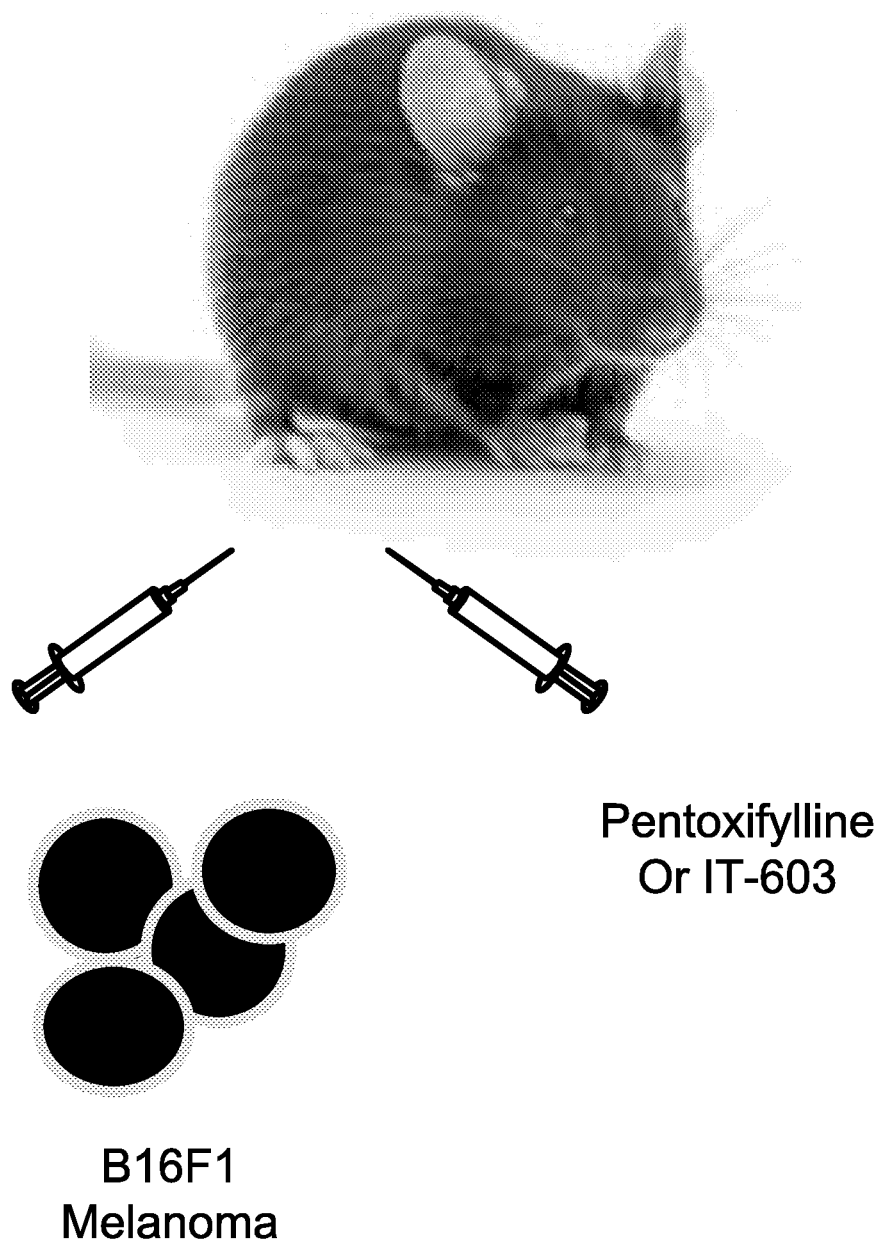
FIG. 3 is a schematic showing administration of PTXF or IT-603 reduced growth of melanoma. C57Bl/6 WT mice were subcutaneously injected with B16F1 melanoma and then injected with either control vehicle or with PTXF (50 mg/kg) or IT-603 (10 mg/kg) on days 0, 2, 3, 4, 6 and 8.

Administration of PTXF or IT-603 reduced growth of melanoma. C57Bl/6 WT mice were subcutaneously injected with B16F1 melanoma and then injected with either control vehicle or with PTXF (50 mg/kg) or IT-603 (10 mg/kg) on days 0, 2, 3, 4, 6 and 8. See FIGS. 3-4. Daily monitoring of tumor volume indicated that PTXF significantly reduced growth of the tumors (p<0.001). IT-603 reduced tumor growth (p<0.08). See FIG. 4.

It was next tested whether PTXF could potentiate the anti-tumor effect of immune-checkpoint blockade therapies given that blockade of CTLA-4 and/or PD-1 by monoclonal antibodies (mAbs) has been shown to exert beneficial effects in several mouse models of cancer such as the SalN fibrosarcoma, or the colon carcinoma 51Blim10 (Leach et al., Science 271(5256):1734-1736, 1996; Pardoll, Nat. Rev. Cancer 12(4):252, 2012), and in humans with solid tumors, especially melanoma and non-small cell lung cancer patients (reviewed in Grosso et al., Cancer Immunity, 13:5, 2013).

Figure 5:
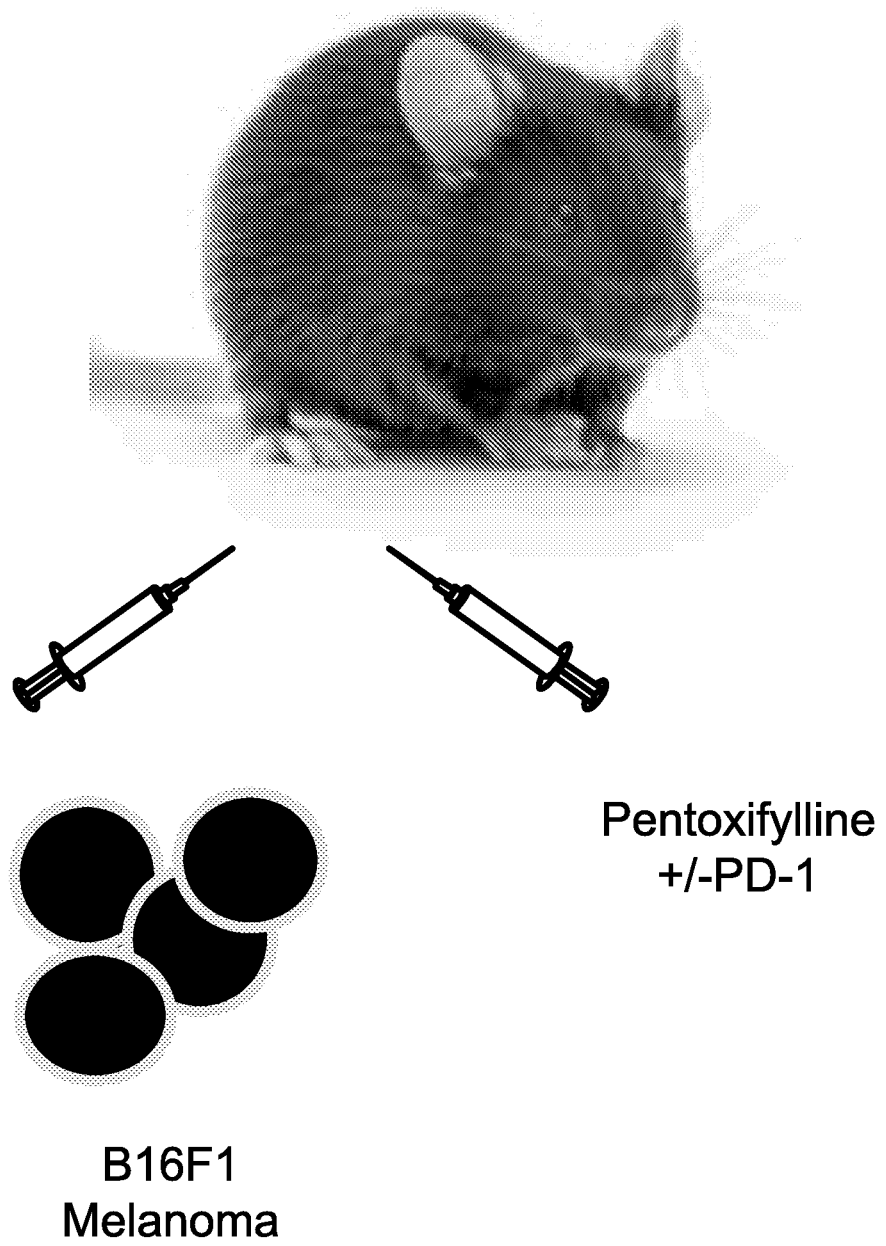
FIG. 5 is schematic showing Use of a combination of anti-PD-1 therapy with PTXF where WT C57Bl/6 mice transplanted with B16F1 cells were treated with PTXF with or without anti-PD-1 mAb (250 micrograms/injection).

In the B16F1 melanoma model, blockade of the PD-1/ PD-L1 pathway had only a minor effect, if any, on tumor growth. See FIG. 6. Thus, the combination of anti-PD-1 therapy with PTXF was tested. WT C57Bl/6 mice transplanted with B16F1 cells were treated with PTXF with or without antiPD-1 mAb (250 micrograms/injection; clone RMP1-14, purchased from BioXCell). See FIG. 5. Other antPD-1 mAbs include OPDIVO® (nivolumab). The mice were injected with PTXF, anti-PD-1 or both. PTXF injections (50 mg/kg)) were given on days 6, 7, 8, 9, and 10, and anti-PD-1 injections (250 μg per injection) were given on days 6, 8, and 10. While PTXF injections alone and anti-PD-1 injections alone did not significantly reduce tumor size the combination of PTXF and antiPD-1 reduced tumor growth by more than 75%. See FIG. 6. These results show that treatment of melanoma by administering PTXF in combination with antiPD-1 mAb synergistically inhibited tumor growth in vivo in human melanoma cells, even when the melanoma has already been established. See FIG. 6.

A dramatic decrease in the proportion and number of CD4+Cd8−Foxp3−CD25+GITR+ Treg precursors was observed in mice lacking canonical NF-κB subunits. See FIG. 7A, 7B, and FIGS. 12B and 12C. As expected, mice lacking c-Rel exhibited a dramatic decrease in Treg cells in all tissues. Although canonical NF-κB subunits p65 and c-Rel can partially compensate for one another, they also play discrete roles in multiple steps of both nTreg and iTreg development. Therefore, canonical NF-κB signaling is crucial for Treg development.

Figures 9A, 9B, 9C, 9D, 9E, 9F, 9G:
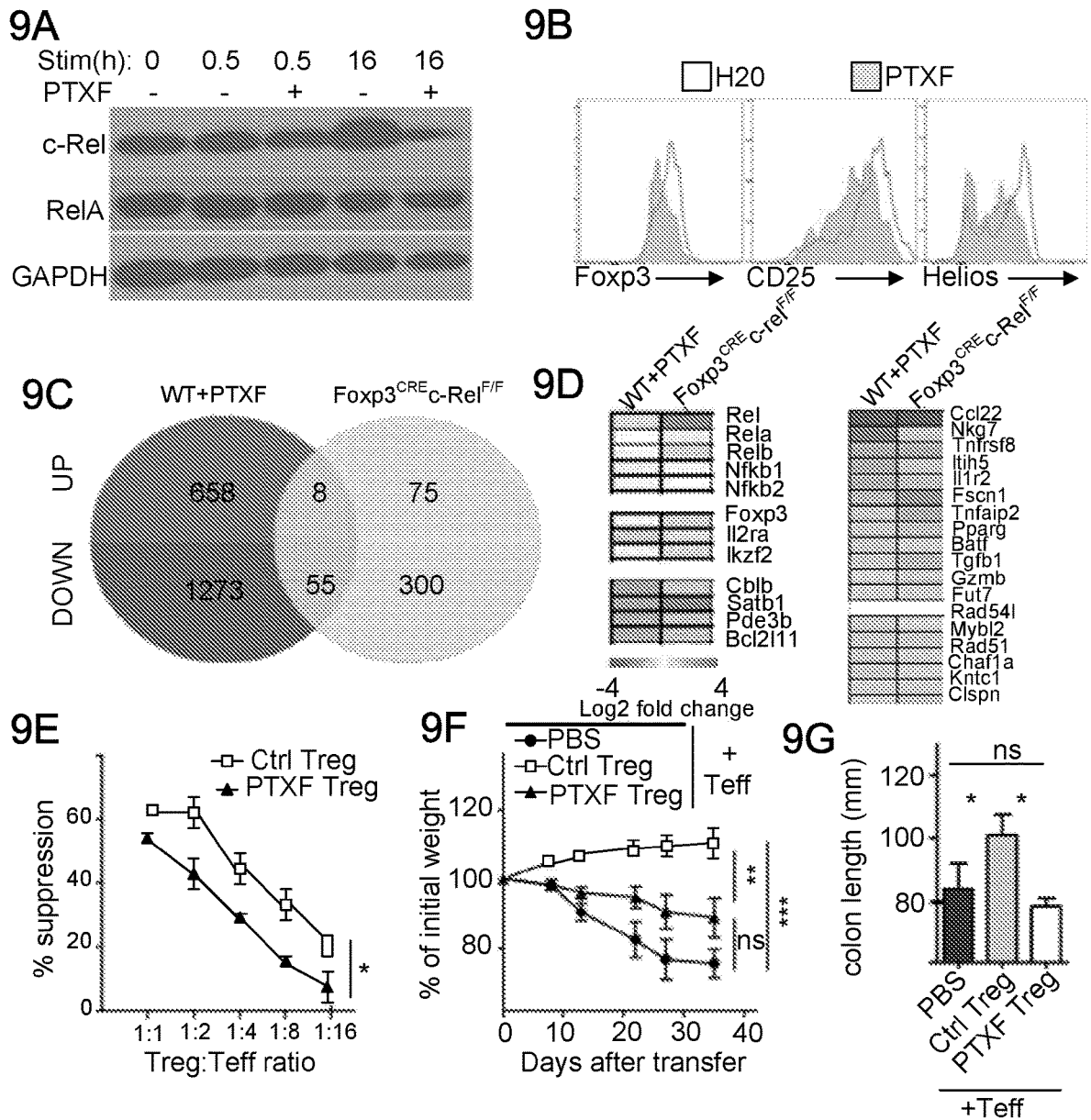
FIG. 9A-9G are graphs illustrating how chemical c-Rel inhibition impairs Treg identity.

It was hypothesized that p65 and c-Rel might have different contributions to treg-mediated tumor tolerance. The growth of B16F1 melanoma cells in mice was measured. Exponential melanoma growth in control Foxp3$^{CRE}$ transgenic animals (FIG. 9A). C-Rel controls a specific genetic program in Treg cells that is required for inhibition of the anti-melanoma protective immune response mediated by CD8 T cells. Treg cells specifically require c-Rel to inhibit anti-tumor effector responses.

Figure 14B:
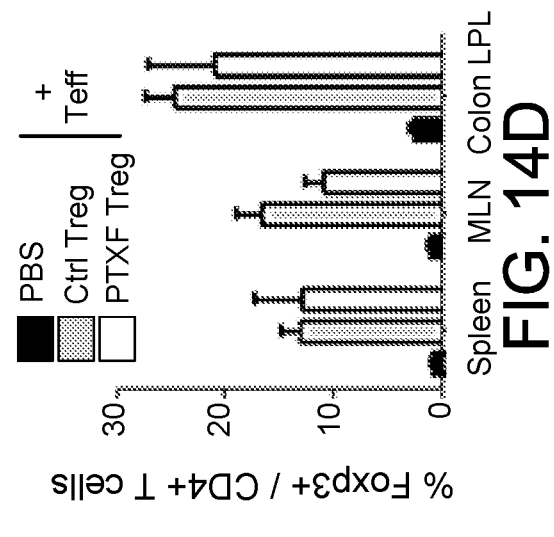
FIG. 14A-14D are graphs illustrating how chemical c-Rel inhibition impairs Treg identity.
Figure 14D:
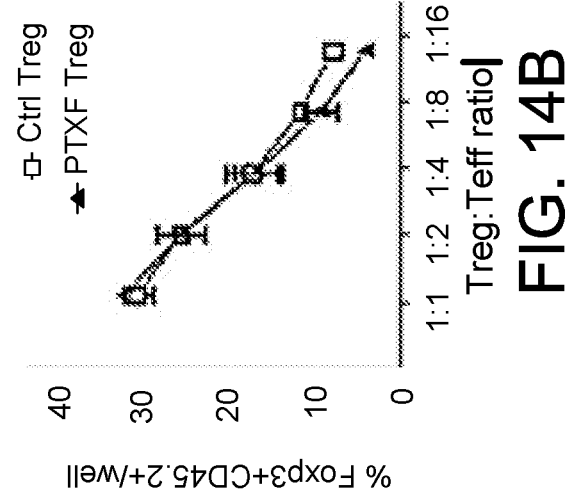

PTXF induced a substantial shift in Treg transcriptional identify that is consistent with loss of c-Rel activity and suggests a loss of suppressive function in the treated Tregs. In an in vitro suppression assay, PTXF-treated Treg cells exhibited only a modest, but significant, reduction in suppression of effector T-cell proliferation when compared to mock-treated Treg cells (FIG. 9E). PTXF did not affect Treg survival but rather impaired their intrinsic function (FIG. 14B, FIG. 14D). PTXF treatment impacts the homeostasis and function of Tregs similar to that seen upon deletion of c-Rel. In sum, c-Rel inhibition impairs Treg identity and tumor growth.

Figure 14A:
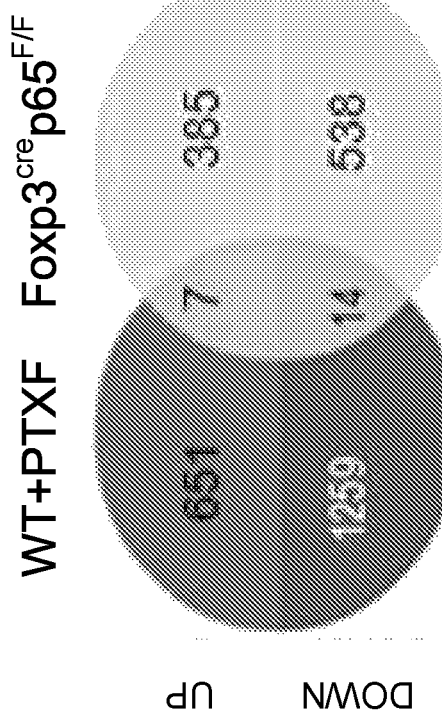
Figure 14C:
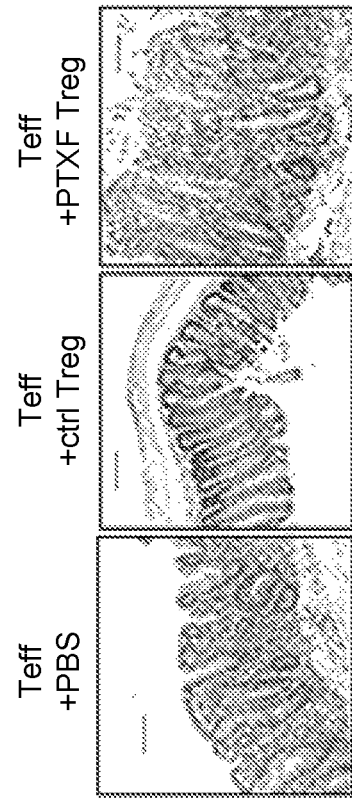

Co-administration of PTXF and anti-PD-1 drove increased expression of IFN-γ by CD4 and CD8 T cells. See FIG. 11B-11C. Monotherapy with PTXF or anti-PD-L1 did not affect tumor growth, but the combination of both PTXF and anti-PDL1 had a synergistic effect by decreasing and delaying melanoma growth (FIG. 14C). PTXF treatment synergizes with checkpoint blockade therapies to inhibit melanoma growth.

The studies presented herein show that the beneficial effects of PTXF require an intact adaptive immune system as the effects of PTXF were abolished in RAG1− deficient animals. Furthermore, decreased fitness of Treg cells in the TILs of PTXF− treated mice was observed, while CD4 and CD8 effector cell infiltration in the tumor microenvironment was enhanced. Thus, PTXF exerted its anti-cancer properties by improving the activity of effector T cells, likely through inhibiting Treg function. PTXF was first proposed to exert anti-inflammatory effects through the down-regulation of cytokine production by macrophages and neutrophils (Hecht et al., 1995). However, the effects of PTXF on T cells is still debated, as the drug seems to down-regulate T-cell effector functions in vitro but has an opposite effect in vivo (Jimenez et al., 2001; Laurat et al., 2001; Suresh et al., 2002). Provided herein is the first demonstration that inhibition of c-Rel by PTXF in vivo provides protection against cancer by targeting Treg cells. No adverse effects of treatment were observed, as the analyses showed the effect of PTXF was restricted to the tumor microenvironment. Thus, it is proposed that this multi-therapy could be used as a safe novel treatment for solid cancers.

4. Embodiments of the Invention

Broad-spectrum inhibition of NF-kB as a therapy for cancer has been proposed for many years. However, blocking the entire NF-kB pathway, especially the p65 subunit, leads to multiple undesired side effects. These observed side-effects have discouraged the development and use of pan-NF-kB inhibitors in the treatment of patients with inflammatory diseases and cancer. The new discovery that specifically inhibiting c-Rel in combination with antiPD-1 mAb had a dramatic effect on reducing tumor growth in melanoma in vitro and in vivo provides a new drug regimen not only for melanoma, including human B16F1 melanoma and B16F10 metastatic melanoma, but also for treating other PD-1-resistant tumors.

Based on the results described here, certain embodiments of the invention are directed to methods of treating melanoma or indeed any PD-1-resistant cancer by administering combination therapy with a c-REL inhibitor such as PTXF and antiPD-1 mAb. Therapeutic doses and methods or schedules of administration are discussed below.

Other checkpoint blockades that have been shown to be therapeutic in cancer include anti-CTLA-4 mAb, anti-CD137 mAb and anti-OX-40 mAb.

PD-1-resistant mouse tumors include, but are not limited to, B16F1 (melanoma), B16F10 (metastatic melanoma), Id8 (ovarian cancer), Sa1N (fibrosarcoma), TUBO (mammary carcinoma), TC-1 (lung sarcoma), BRaf$^{CA}$, Pten$^{loxP}$, Tyr:: CreER$^{T2}$ (spontaneous model of melanoma), MC38 (colon carcinoma) and CT-26 (colon carcinomas). Embodiments of the invention are directed to treatment of any PD-1-resistant tumors, including any similar PD-1-resistant tumors in human patients, known in the art by persons of skill, by administering a therapeutically effective amount of a c-REL inhibitor and an inhibitor of PD-1. In addition, the methods and compositions described here are contemplated for use in any cancer that would benefit from increasing the effector immune response, including but not limited to, for example, non-small cell lung cancer, and for use in inflammatory diseases.

C-Rel Controls Treg Cell Function During Anti-Tumor Responses

Canonical NF-κB is crucial for the normal genetic program in mature Treg cells and for the maintenance of immune tolerance (Oh et al.). The different transcriptional functions performed by p65 and c-Rel suggested that Tregs lacking c-Rel might be deficient in regulating tumor tolerance. Strikingly, the ablation of c-Rel, but not p65, in mature Treg cells strongly impaired melanoma growth in a CD8 T-cell-dependent manner. This might be due to c-Rel−regulated genes that are crucial for Treg homeostasis and function, and are specifically associated with an activated Treg transcriptional program (Luo et al., 2016).

Ablation of c-Rel, but not p65, destabilized Treg-associated gene expression while driving the expression of inflammatory cytokines, thereby shifting the cells towards a more effector-like phenotype. In particular, the expression of Helios, which was recently implicated in the maintenance of Treg cell homeostasis and the suppression of tumor immunity, was reduced in the absence of c-Rel (Nakagawa et al., 2016). Thus, c-Rel appears to specifically enable Tregs to inhibit protective T cell responses, including anti-tumor responses. In WT mice, Tregs efficiently inhibited effector CD8 T cells, thereby allowing uncontrolled cancer cell proliferation. In Foxp3$^{CRE}$c-Rel$^{F/F}$ animals however, the impaired function of Treg cells led to increased activation of effector cells, thus enhancing the killing of tumor cells. This, combined with the lack of evidence of a role for c-Rel in prevention of autoimmunity (Oh et al.), and in effector CD8 responses, suggested that the therapeutic targeting of c-Rel could selectively ablate Treg mediated tumor tolerance.

C-Rel Inhibition as a Cancer Immunotherapy

An extensive body of literature describes the roles of NF-κB in the initiation, proliferation and propagation of tumors. This has led multiple groups to test whether global inhibition of NF-κB could have an effect on tumor growth (DiDonato et al., 2012). For instance, inhibition of IKK activity by thalidomide, by chemicals such as BAY11-7082, or by the small inhibitory peptide NBD (for Nemo-Binding Domain), decrease severity of lymphomas (reviewed in (Kim et al., 2006)). Downstream of IKK, proteasome inhibitors such as Bortezomib, that prevent the degradation of the NF-κB inhibitor IκBα, reduced tumor growth in pre-clinical models of lung and ovarian cancer, and lymphoma (Chang et al., 2012; Xue et al., 2011). Bortezomib (Velcade) is now a FDA-approved drug and is used for the treatment of multiple myeloma, and has significant positive outcome (Mulligan et al., 2007; Orlowski and Kuhn, 2008). Despite these promising results, the use of such non-specific NF-κB inhibitors has been complicated by the observation of multiple adverse effects, such as systemic inflammation through IL-1β overexpression, or non-immune-related complications (Greten et al., 2007; Moreau et al., 2012). This could be a consequence of (i) the inhibition of non-NF-κB related pathways upon inhibition of IKK (Chariot, 2009; Oeckinghaus et al., 2011), or (ii) the inhibition of the p65 subunit of NF-κB, that is well known to exert central roles in organogenesis and inflammation.

Results using conditional mutant mice suggested that c-Rel, whose biological function is mainly restricted to the adaptive immune system, could be a specific target for the treatment of cancer through its role in Treg cells. In vitro, we observed that PTXF reduced the level of c-Rel protein in Treg cells, while impairing the molecular identity of Tregs, including decreased Foxp3 expression, and Treg suppressive function. In agreement with previously published results, PTXF affected c-Rel but not other NF-κB subunits (Wang et al., 1997). RNAseq revealed a profound effect of PTXF on Treg-associated gene expression that was partially overlapping with changes observed in c-Rel-deficient Treg cells. Interestingly, the expression of c-Rel mRNA itself was unchanged, suggesting a post-translational effect of PTXF on c-Rel expression. Moreover, Foxp3 mRNA was unaffected by PTXF. This might be explained by the enhanced expression of Cbl/b, a ubiquitin ligase involved in the targeting of Foxp3 to the proteasome (Zhao et al., 2015). On the other hand, genes required for optimal Treg function and immunosuppression in the tumor microenvironment, such as Tgfb1 or Gzmb (Boissonnas et al., 2010; Donkor et al., 2011), were directly repressed by PTXF treatment, similar to that seen upon genetic deletion of c-Rel. Profound effects of c-Rel deletion and PTXF treatment were observed on the gene expression signature of activated Treg cells (aTreg), suggesting c-Rel is selectively required for the function of this subset of Treg cells that are essential for tumor tolerance (Luo et al., 2016). Thus, PTXF affects Treg identity both directly by modifying c-Rel-dependent transcription, and indirectly by forcing the expression of genes that promote anti-tumor responses.

Certain other embodiments are directed to pharmaceutical formulations comprising a c-Rel inhibitor and a PD-1 inhibitor as described below.

Pharmacological Formulations

Certain embodiments of the present invention are directed to pharmaceutical compositions and formulations of the active agents/therapeutic agents (used interchangeably) as described herein for treatment of melanoma and any other PD-1-resistant cancer including those that are listed above herein, the "enumerated diseases."

For the purpose of embodiments of the invention, active agents/therapeutic agents broadly include any agent that can inhibit c-REL including the methylxanthine derivative, pentoxifylline (PTXF; also known under the brand names Trental®, Pentox®, Pentoxil® and Flexital®), with the chemical structure 1-(5-oxohexyl)-3,7-dimethylxanthine, and the herein-described antibodies against PD-1 and PDL-1, including monoclonal antibodies, preferably humanized antibodies and biologically active fragments or variants thereof. The pharmaceutical formulations are combinations of one or more C-Rel inhibitors and one or more of the Anti-PD-1 or anti-PDL-1 antibodies. PTFX is a phosphodiesterase inhibitor, and also inhibits NF-κB, c-Rel, TNF, and leukotriene, and raises intracellular cAMP, activates PKA, and reduces inflammation. Active agents contemplated for use with this invention further include any analogs or derivatives of PTXF such as lisofylline, torbafylline, propentofylline, and A81-3138. All of these analogs are believed to exert their pharmaceutical effects by inhibiting phosphodiesterase and elevating intracellular cAMP, for example in certain cell types, including neutrophils. Due to their effects on neutrophils and effects on the action of tumor necrosis factor, pentoxifylline and its analogs have been studied for effects on the immune system and treatment for severe bacterial infection. Pentoxifylline has been used or suggested for use in conditions such as intermittent claudication and diabetic neuropathy, due to its ability to increase blood flow, and in particular microcirculation, to enhance oxygenation of tissues. See also U.S. Pat. No. 9,035,050 for more substituted xanthine derivatives that can be used in embodiments of the invention.

Methylxanthine derivatives and analogs of pentoxifylline are expected to share some or all of these effects. Therefore, persons of skill in the art can select any of these chemically related analogous compounds, or any other related methylxanthine compounds known in the art. For example, U.S. Pat. Nos. 8,952,016 and 9,035,050, the disclosures of which are incorporated here by reference in their entirety, describe such compounds and methods for their synthesis. Any pentoxifylline, lisofylline and theophylline analogs are contemplated for use with the invention herein described, for example, theophylline, dyfylline, doxofylline, lisofylline, pentoxifylline, torbafylline, propentafylline, A81-138, isobutyl methylxanthine (IBMX), caffeine, and the like.

Some natural compounds and their synthetic derivatives inhibit Rel or NF-κB via specific interaction with the cysteine residues critical for binding to the specific κB-DNA sequence (Ouk S, Liou M L, Liou H C. Direct Rel/NFκB inhibitors: structural basis for mechanism of action. Future Med Chem. 2009; 1:1683-70720). For example, dehydroxymethylepoxyquinomicin (DHMEQ) was shown to inhibit NF-κB binding activity. The hydrophobic small molecule pyrimidinetrione and its derivatives were identified as potent and highly specific inhibitors of c-Rel activity, having a 20-200 fold higher inhibitory effect on c-Rel and NF-κB than on other transcription factors such as Oct1 and AP1. These compounds bind c-Rel directly and change the conformation of the protein, inhibiting DNA binding and transcriptional activity. Several generations of pyrimidinetrione derivatives have been developed and one of those compounds is IT-603 that resulted in most efficient inhibition of c-Rel activity without altering cell viability after 24 hours of incubation (Y. Shono et al., Cancer Discov. 2014 May; 4(5): 578-591. doi:10.1158/2159-8290.CD-13-0585. All of these c-Rel inhibitors including IT-603, and the newer compound IT-901, are active agents for the purpose of embodiments of the invention. IT-603 is available commercially and is a cell-permeable compound that directly and reversibly binds to c-Rel to change its conformation and blocks its DNA binding and transcriptional activity ($IC_{50}=3$ µM).

Lisofylline (1-(5-hydroxyhexyl)-3-methylxanthine) is an active metabolite of pentoxifylline which acts to inhibit phosphodiesterase. It has been reported to protect against septic shock and to inhibit inflammation via inhibition of tumor necrosis factor. In addition, lisofylline may be useful in diabetes (type 1 and type 2) and in heart disease because of its reputed effects on these systems and generally on inflammation and immune damage. Methods for synthesizing lisofylline and certain lisofylline analogs are available in U.S. Patent Publication No. 2013-0137693, the disclosures of which are hereby incorporated by reference.

Torbafylline (7-(ethoxymethyl)-1-(5-hydroxy-5-methylhexyl)-3-methylxanthine; sometimes referred to as HWA-448) also is a phosphodiesterase inhibitor operating via cAMP effects. See Joshi et al., "Phosphodiesterase (PDE) Inhibitor torbafylline (HWA 448) attenuates burn-induced rat skeletal muscle proteolysis through the PDE4/cAMP/EPAC/PI3vK/Akt pathway," Mol. Cell. Endocrinol. 393(1-2):153-162, 2014.

Propentofylline (3-methyl-1-(5-oxohexyl)-7-propylxanthine; sometimes referred to as HWA-285) is a phosphodiesterase inhibitor with purported neuroprotective effects, which acts as a vasodilator and an anti-inflammatory. It is being studied for use in treatment of Alzheimer's disease and vascular dementia.

A81-138 (1-(5-hydroxy-5-methylhexyl)-3-methylxanthine; sometimes referred to as HWA-138) is a newer pentoxifylline analog which is reported to have properties and actions similar to pentoxifylline.

IMBX (3-isobutyl-1-methylxanthine) is less specific phosphodiesterase inhibitor compound which acts in the same manner as pentoxifylline.

Theophylline (1,3-dimethylxanthine), dyfylline (7-(2,3-dihydroxypropyl)-theophylline; also known as diprofylline) and doxofylline (7-(1.3-dioxolan-2-ylmethyl)-1.3-dimethylpurine-2,6-dione) are phosphodiesterase inhibitor compounds with vasodilating and bronchodilating effects. These methylxanthine derivatives also are contemplated for use in the invention, in addition to any theophylline or caffeine derivatives known in the art.

The therapeutic agents are generally administered in an amount sufficient to treat or prevent an enumerated disease or any PD-1 disease. The pharmaceutical compositions of the invention provide a therapeutic amount of the active agents effective to treat or prevent an enumerated disease or disorder. In certain embodiments, the pharmaceutical compositions of the present invention comprise about 0.1 mg to 5 g of each active agent.

In certain embodiments, the therapeutically effective amounts of the c-Rel inhibitors ranges from about 0.1 mg to 5 g of each active agent. The therapeutic dose can vary widely for example from about 1-25 mg/day, 25-50 mg/day, 50-100 mg/day, 100-200 mg/day, 200-300 mg/day, 400-500 mg/day and 500-1000 mg/day, 0.5 mg to about 1 g, about 1 mg to about 750 mg, about 5 mg to about 500 mg, or about 10 mg to about 100 mg of therapeutic agent. For the FDA-approved use in treating intermittent claudication, pentoxifylline is prescribed at 400 mg orally 3 times a day. If adverse effects develop, reducing the dose to 400 mg twice a day is recommended. The person of skill in the art, or any physician, is able to adjust the dose as needed and depending upon the patient's weight, general health, kidney and liver function, and the degree of disease being treated. Pentoxifylline has low toxicity, therefore considerably higher doses can be administered if necessary. The drug preferably is given orally, but also can be administered intravenously, subcutaneously, intramuscularly, intraperitoneally, intrathecally, transdermally, topically or by any other convenient means known in the art.

The therapeutic doses of anti-PD-1 and anti-PDL-1 antibodies in clinical trials is between 1 to 10 mg/kg every week or every 2 weeks. This dose range can vary widely depending on the factors described here. A range of antibodies for use in embodiments of the invention is therefor from about 0.1 mg to 5 g and can be administered as needed multiple times per day, or per week, or per month. The usual dose used in mice is 200 µg/injections every 2 or 3 days.

It is understood that the appropriate dose of an active agent depends upon a number of factors within the ken of the ordinarily skilled physician, veterinarian, or researcher for example, the identity, size, and condition of the subject or sample being treated, further depending upon the route by which the composition is to be administered, the type and strength of the formulation, the pharmacokinetics of the formulation, the frequency of administration, the severity of the disease, and the effect which the practitioner desires the an active agent to have. It is furthermore understood that appropriate doses of an active agent depend upon the potency with respect to the expression or activity to be modulated. Such appropriate doses may be determined using the assays described herein. When one or more of these active agents are to be administered to an animal (e.g., a human), a relatively low dose may be prescribed at first, with the dose subsequently increased until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Active agents can be administered as a single treatment or, preferably, can include a series of treatments that continue at a frequency and for duration of time that causes one or more symptoms of the enumerated disease to be reduced or ameliorated, or that achieves the desired effect including reducing tumor burden or metastasis. Typical frequencies of administration of therapeutic agents in embodiments of the invention include once per day, multiple times per day, every few days, every week or every few weeks, as needed and as determined by the physician. Active agents administered "together" can be administered at the same time in the same or different formulations, or at different times.

Active agents of the invention may be chemically modified to facilitate uptake by the skin, for basal cell carcinoma (BCC), or by the brain or pancreas or other target organ using methods known in the art.

The term "administer" is used in its broadest sense and includes any method of introducing the compositions of the present invention into a subject. Administration of an agent "in combination with" includes parallel administration of two agents to the patient over a period of time, co-administration (in which the agents are administered at approximately the same time, e.g., within about a few minutes to a few hours of one another), and co-formulation (in which the agents are combined or compounded into a single dosage form suitable for oral, topical, subcutaneous or parenteral administration).

The pharmaceutical compositions of the present invention may be administered in a number of ways depending upon whether local (to the skin or tumors) or systemic treatment is desired and upon the area to be treated. For BCC, topical administration may be preferred, which also means that higher doses can be applied that might be administered systemically. Topical and systemic administrations are not mutually exclusive.

Administration can also be intravenous, parenteral, intraarterial, subcutaneous, intraperitoneal or intramuscular injection or infusion, intraopthalmic; or intracranial, e.g., intrathecal or intraventricular, administration. In recent years there has been a tendency towards the development of controlled release dosage forms that will provide therapy over an extended period of time. Normally this would be once a day, and it is believed that such a change in dosage regimen will reduce adverse reactions and side effects and also improve patient compliance. The use of synthetic polymers that may have muco- or bio-adhesive properties has been investigated and is disclosed in WO 85/02092.

In some embodiments, a slow-release preparation comprising the active agents is formulated. It is desirable to prolong delivery with these slow release preparations so that the drug may be released at a desired rate over this prolonged period. By extending the period, the drug can if required be released more slowly, which may lead to less-severe adverse reactions and side effects. The preparation of sustained, controlled, delayed or anyhow modified release form can be carried out according to different known techniques: 1. The use of inert matrices, in which the main component of the matrix structure opposes some resistance to the penetration of the solvent due to the poor affinity towards aqueous fluids; such property being known as lipophilia; 2. The use of hydrophilic matrices, in which the main component of the matrix structure opposes high resistance to the progress of the solvent, in that the presence of strongly hydrophilic groups in its chain, mainly branched, remarkably increases viscosity inside the hydrated layer; and 3. The use of bioerodible matrices, which are capable of being degraded by the enzymes of some biological compartment. See U.S. Pat. No. 7,431,943.

The term "slow release" refers to the release of a drug from a polymeric drug delivery system over a period of time that is more than one day wherein the active agent is formulated in a polymeric drug delivery system that releases effective concentrations of the drug. Drug delivery systems may include a plurality of polymer particles containing active drug material, each of the particles preferably having a size of 20 microns or less, and incorporating on the outer surface of at least some of the particles a bioadhesive material derived from a bacterium. Such drug delivery systems have been described in U.S. Pat. No. 6,355,276. The use of these microorganisms in the design allow for a controlled release dosage form with extended gastrointestinal residence.

In certain embodiments, dosage forms of the compositions of the present invention include, but are not limited to, implantable depot systems.

Self-emulsifying microemulsion drug delivery systems (SMEDDS) are known in the art See U.S. Patent Application 2001/00273803. The term SMEDDS is defined as isotropic mixtures of oil, surfactant, cosurfactant and drug that rapidly form an oil-in-water microemulsion when exposed to aqueous media or gastrointestinal fluid under conditions of gentle agitation or digestive motility that would be encountered in the gastrointestinal tract.

Thermostable nanoparticles may be contained in a drug delivery system targeted for the GI tract. See U.S. Patent Application No. 2000/60193787. These drug delivery systems may include at least one type of biodegradable and/or bioresorbable nanoparticle and at least one drug that possesses at least one of the following properties: emulsifier or mucoadhesion. The drug may substantially cover the surface of the nanoparticle.

The therapeutic agent can be formulated with an acceptable carrier using methods well known in the art. The actual amount of therapeutic agent will necessarily vary according to the particular formulation, route of administration, and dosage of the pharmaceutical composition, the specific nature of the condition to be treated, and possibly the individual subject. The dosage for the pharmaceutical compositions of the present invention can range broadly depending upon the desired effects, the therapeutic indication, and the route of administration, regime, and purity and activity of the composition.

A suitable subject, preferably a human, can be an individual or animal that is suspected of having, has been diagnosed as having, or is at risk of developing an enumerated disease, and like conditions as can be determined by one knowledgeable in the art.

Techniques for formulation and administration can be found in "Remington: The Science and Practice of Pharmacy" (20th edition, Gennaro (ed.) and Gennaro, Lippincott, Williams & Wilkins, 2000), incorporated herein by reference.

The pharmaceutical compositions of the present invention may be administered in a number of ways depending upon whether local or systemic treatment is desired and upon the area to be treated. Administration may be-oral, intraopthalmic, or parenteral. Parenteral administration includes intravenous, intraarterial, subcutaneous, intraperitoneal, or intramuscular injection or infusion; or intracranial, e.g., intrathecal or intraventricular, administration.

Active agents may be admixed, encapsulated, conjugated or otherwise associated with other molecules, molecule structures or mixtures of compounds, such as for example, liposomes, receptor targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Solutions or suspensions used for parenteral, intradermal, intraopthalmic, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diamine tetra acetic acid (EDTA); buffers such as acetates, citrates or phosphates; and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where the therapeutic agents are water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.) or phosphate buffered saline (PBS). In all cases, the composition must be sterile and should be fluid to the extent that easy syringability exists. It should be stable under the conditions of manufacture and storage and should be preserved against the contaminating action of microorganisms such as bacteria and fungi.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active agent in the required amount in an appropriate solvent with one or a combination of the ingredients enumerated above, as required, followed by filter sterilization. Generally, dispersions are prepared by incorporating the active agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. Depending on the specific conditions being treated, pharmaceutical compositions of the present invention for treatment of atherosclerosis or the other elements of metabolic syndrome can be formulated and administered systemically or locally. Techniques for formulation and administration can be found in "Remington: The Science and Practice of Pharmacy" (20th edition, Gennaro (ed.) and Gennaro, Lippincott, Williams & Wilkins, 2000). For oral administration, the agent can be contained in enteric forms to survive the stomach or further coated or mixed to be released in a particular region of the GI tract by known methods. For the purpose of oral therapeutic administration, the active agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL® or corn starch; a lubricant such as magnesium stearate or STEROTES® a glidant such as colloidal silicon dioxide; a sweetening agent such as sucrose or saccharin; or a flavoring agent such as peppermint, methyl salicylate, or orange flavoring.

Systemic administration can also be by transmucosal means to the buccal membrane, gums, intestine or colon. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active agents are formulated into ointments, salves, gels, or creams as generally known in the art.

In one embodiment, the active agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to particular cells with, e.g., monoclonal antibodies) also can be used as pharmaceutically acceptable carriers. These can be prepared according to methods known to those skilled in the art.

Antibodies

The term "antibody" herein is used in the broadest sense and specifically covers all antibodies for use in embodiments of the invention including anti-PD-1, anti-PDL-1, anti-CTLA-4, anti-CD137 and anti-OX-40 antibodies, and further includes monoclonal antibodies, polyclonal antibodies, multispecific antibodies (e.g., bispecific antibodies) formed from at least two intact antibodies, and antibody fragments or variants so long as they exhibit the desired biological activity against PD-1 or anti-PDL-1 antibodies. The anti- PD-1 and anti-PDL-1 antibodies are preferably humanized antibodies. In one embodiment of the methods described herein, the antibodies are fully human antibodies, mono- or polyclonal.

Antibodies for use in the embodiments disclosed herein can be produced using any of the methods known in the art. These methods of producing antibodies include immunizing a mammal (e.g., mouse, rat, rabbit, horse, goat, sheep or monkey) with the protein or other antigen or hapten. Antibodies may be obtained from immunized animals using any of a variety of techniques known in the art, and screened, preferably using the binding of the antibody to the antigen of interest.

Various procedures known within the be used for the production of antibodies for use in embodiments of the invention, including mono- and polyclonal antibodies directed against a polypeptide of the invention (e.g., any checkpoint protein), or against derivatives, fragments, variants, analogs homologs or orthologs thereof. See, for example, ANTIBODIES: A LABORATORY MANUAL, Harlow and Lane (1988) Cold Spring Harbor Laboratory Press, Cold Spring Harbor, N.Y. Some of these antibodies are discussed below. Methods for making fully human monoclonal antibodies are described in CURRENT PROTOCOLS IN IMMUNOLOGY, ed. John E Coligan, Barbara E Bierer, David H Margulies, Ethan Shevach, Warren Strober, 1994-2006 John Wiley & Sons, Inc. These methods are well-known in the art.

1. MONOCLONAL ANTIBODIES

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarily determining regions (CDRs) of the monoclonal antibody are identical in all the molecules of the population. MAbs thus contain unique antigen-binding site capable of binding specifically with a particular epitope of the antigen. Thus, "monoclonal" antibodies are distinguished from "polyclonal" antibodies, which are a mixture of discrete antibodies that have multiple binding specificities.

Monoclonal antibodies can be prepared using hybridoma methods, such as those described by Kohler and Milstein (1975) Nature, 256:495; and by Coding, Monoclonal Antibodies: Principles and Practice, pp. 59-103 (Academic Press, 1986), the disclosures of which are hereby incorporated by reference.

Monoclonal antibody-producing hybridoma cells can be seeded and grown in a suitable culture medium that preferably contains one or more substances that inhibit the growth or survival of the unfused, parental myeloma cells. Preferred myeloma cells are those that fuse efficiently, support stable high level expression of antibody by the selected antibody producing cells, and are sensitive to a medium such as HAT medium. Culture medium in which the hybridoma cells are growing is assayed for the presence of monoclonal antibodies directed against the epitope of interest, i.e., PD-1. Preferably, the binding specificity is determined by enzyme-linked immunoabsorbance assay (ELISA) or any similar assay known in the art. The monoclonal antibodies of the current invention are those that specifically bind to PD-1

In a preferred embodiment, the monoclonal antibody has an affinity greater than micromolar (i.e. an affinity greater than $10^{-6}$ mol), which can be determined easily by those of skill in the art, for example, by Scatchard analysis, see Munson & Pollard, Anal. Biochem. 107:220, 1980.

2. ANTIBODY FRAGMENTS

In certain circumstances there are advantages to using antibody fragments, rather than whole antibodies. The smaller size of the fragments allows for rapid clearance, and may lead to improved access to tissues. For a review of certain antibody fragments, see Hudson et al. (2003) Nat. Med. 9:129-134. Therefore, antibodies suitable for use with the methods described herein can also include fragments, variants, or derivatives thereof that have substantially the same antigen specificity. Examples of antibody fragments capable of binding an antigen or other binding partner are known to persons of skin in the art and include, for example, the Fab fragment consisting of the VL, VH, Cl and CH domains; the Fd fragment consisting of the VH and CH1 domains; the Fv fragment consisting of the VL and VH domains of a single arm of an antibody; the dAb fragment which consists of a VH domain; isolated CDR regions and Fab'2 fragments, a bivalent fragment including two Fab fragments linked by a disulphide bridge at the hinge region. Single chain Fv fragments are also included. Any fragment or partial antibody or antibody variant may be used so long as it is able to bind the epitope of interest sufficiently strongly.

Fragments of antibodies that are suitable for use with the methods described herein may be generated by traditional means, or known techniques, such as enzymatic digestion, or by recombinant techniques. Traditionally, these fragments have been derived via proteolytic digestion of intact antibodies (see, e.g., Morimoto et al., Journal of Biochemical and Biophysical Methods 24:107-117 (1992); and Brennan et al., Science, 229:81 (1985)). However, these fragments now can be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above.

Alternatively, Fab'-SH fragments can be directly recovered from E. coli and chemically coupled to form F(ab')2 fragments (Carter et al., Bio/Technology 10: 163-167 (1992)). According to another approach, F(ab')2 fragments can be isolated directly from recombinant host cell culture. Fab and F(ab')2 fragments with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. ScFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

3. ANTIBODY VARIANTS

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired binding characteristics. The amino acid alterations may be introduced in the subject antibody amino acid sequence at the time that sequence is made. A useful method for identification of certain residues or regions of the antibody that are preferred locations for mutagenesis is called "alanine scanning mutagenesis" as described by Cunningham and Wells (1989) Science, 244: 1081-1085.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. (1997) TIBTECH 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

Other antibody variants having one or more amino acid substitutions are provided. Sites of interest for substitutional mutagenesis include the hypervariable regions, but 1-K alterations are also contemplated.

Modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain Amino acids may be grouped according to similarities in the properties of their side chains (in A. L. Lehninger, Biochemistry, 2nd ed., pp. 73-75, Worth Publishers, New York (1975)).

Non-conservative substitutions will entail exchanging a member of one of these classes for another class. Such substituted residues also may be introduced into the conservative substitution sites or, into the remaining (non-conserved) sites.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions including that of a hinge cysteine.

4. EXAMPLES

This invention is not limited to the particular processes, compositions, or methodologies described, as these may vary. The terminology used in the description is for the purpose of describing the particular versions or embodiments only, and is not intended to limit the scope of the present invention which will be limited only by the appended claims. Unless defined, otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are described. All publications mentioned herein, are incorporated by reference in their entirety. Nothing herein is to be construed as an admission that the invention is not entitled to antedate such disclosure by virtue of prior invention.

Example 1

Materials and Methods

A. Animals, Cell Lines, Antibodies and Drugs

Foxp3$^{CRE-YFP}$ mice and mice carrying floxed alleles of NF-kB subunits (p65 and c-Rel floxed) were gifts. P65-floxed mice were obtained from R. Schmid (Munich, Germany)(Algul et al., 2007) and c-Rel– floxed mice from U. Klein (Columbia University, New York)(Heise et al., 2014). CD4$^{cre}$ (Tg(CD4– cre)$^{1Cw1}$), Foxp3$^{CRE-YFP}$ (Foxp3$^{tm-4(YFP/cre)Ayr}$), Foxp3$^{EGFP}$ (Foxp3$^{tm2Tch}$), Foxp3$^{RFP}$ (Foxp3$^{tm1Flv}$), CD45.1 (Ptprc$^a$ Pepc$^b$/BoyJ) and RAG1$^{-/-}$ were originally purchased from the Jackson Laboratory and maintained in our animal facility. WT C57BI/6J mice were purchased from the Jackson Laboratory. Mice were housed under SPF conditions, according to IACUC guidelines. All animals used for experiments were 5-9 weeks old.

B16F1, B16F10 and CT-26 cells were obtained from the ATCC and grown in DMEM+10% FBS medium. BRAF$^{CA}$Pten$^{-/-}$ cells were originally derived from an in vivo melanoma induced by topical tamoxifen treatment of Ubc$^{cre-ERT2}$ BRAF$^{CA}$ Pten$^{F/F}$, as described. All cell lines were periodically tested for murine pathogens. Cells were grown in DMEM supplemented with 10% FBS. When confluence reached 60-70%, cells were detached and washed in PBS1X. Fifty thousand cells diluted in 50 μL PBS1X were injected subcutaneously in the shaved abdomen of each mouse. Tumor growth was measured daily using a caliper.

Pentoxifylline (Sigma) powder was dissolved in PBS1X and sterile filtered prior to each injection. For the early regimen of pentoxifylline treatment, mice were injected intra-peritoneally with 50 mg/kg pentoxifylline diluted in 100 μL PBS1X at days 0, 1, 2, 3, 5, 7, and 9. For the "curative" regimen, mice were treated daily from day 5-6 (when the tumor was visible and palpable) to day 11, following the same methods. IT-603 was reconstituted in DMSO and stored at −80° C. It then was diluted in PBS1X and sterile-filtered prior to each injection. Mice were injected intra-peritoneally with 10 mg/kg pentoxifylline diluted in 100 µL PBS1X at days 0, 1, 2, 3, 5, 7 and 9.

Anti-PD-1 antibody (clone RMP1-14, BioXCell®) or isotype control (polyclonal IgG, BioXCell®) is available commercially. The antibodies were aliquoted in sterile PBS1X and stored at −80° C. until use. Mice are injected intra-peritoneally with 200µ of anti-PD-1 or isotype antibody, diluted in 100 µL sterile PBS1X at days 6, 8 and 10. All injections are performed using a 27.5 gauge needle, following the standard precautions.

B. Tumor Transfer and Treatments $5\times10^4$ B16F1 or $5\times10^5$ CT-26 or BRAF$^{CA}$Pten$^{-/-}$ cells diluted in sterile PBS1X were injected subcutaneously into the shaved flank of each mouse. For metastasis experiments, $2.5\times10^4$ B16F10 cells were injected intravenously in the tail vein. PTXF (Sigma) was diluted in PBS1X and sterile filtered prior to each injection. Anti-PD-1 (RMP1-14), anti-PD-L1 (10F.9G2) and anti-CD8 (YTS.169-4) mAbs were obtained from BioXCell. Rat IgG isotype control was from R&D Systems. Mice received intraperitoneal injections of 50 mg/kg PTXF or 200 µg of the given mAb. In FIG. 11A-11G, Balb/c mice harboring CT-26 tumors received a suboptimal dose of 100 µg of anti-PD-1.

C. Flow Cytometry

Cells were isolated from thymus, spleen and lymph nodes by mechanical desegregation in PBS+ FBS 3%. For tumor-infiltrating cell suspensions, total tumors were digested in DMEM (Gibco) supplemented with 1 mg/ml collagenase type IV (Sigma) and 1 mg/ml DNase I (Sigma) for 40 minutes at 37° C., followed by centrifugation in a 36% Percoll solution. For intracellular cytokines analyses, cell suspensions were incubated 3 hours with PMA (Sigma, 50 ng/mL), ionoymycin (Sigma, 1 µg/mL) in the presence of Golgi Plug (BD), or incubated 4 hours with mitomycin C-treated WT splenocytes loaded with 10 mg/mL gp100/pmel 17 peptide (Neo Biolab) in the presence of Golgi Plug. Cells were then stained with mAbs purchased by eBioscience or Tonbo Bioscience. Foxp3 and cytokine staining were performed using the eBioscience kit and protocol. Cells were acquired on a LSR II (BD Biosciences) and analyzed with FlowJo (Tree Star) software.

D. In Vitro Treg Differentiation

CD4$^+$CD44$^{low}$CD25$^-$ naïve T cells were FACS-sorted from splenocyte suspensions. $10^5$ T cells were cultured in complete RPMI (Gibco) with $10^5$ T-cell depleted, mitomycin C-treated WT splenocytes and 2.5 µg/mL anti-mCD3 (BioXCell), in the presence of 10 ng/mL mIL-2 (Peprotech) and grading doses of human TGF-β1 (Peprotech), for 4 days at 37° C. Cells were then stained for flow cytometry analysis.

E. In Vitro PTXF Treatment

CD4$^+$YFP$^+$ Treg cells were FACS-sorted and pre-incubated with 500 µg/mL PTXF or H$_2$O for 15 minutes at 37° C. Total cells suspensions were then activated with 5 µg/mL plate-coated anti-mCD3, 1 µg/ml soluble anti-mCD28 (BioLegend) and 10 ng/mL mIL-2, overnight at 37 C. Treg cells were then washed for further use.

F. Suppression Assays

For in vitro assays, CD45.1$^+$ naïve conventional CD4+ T cells were magnetically isolated (Miltenyi) and labelled with CellTrace Violet Proliferation Tracker (Life Technologies). They were cultured with T-cell depleted, mitomycin C-treated WT splenocytes and 2.5 µg/mL anti-mCD3, in the presence or not of treated Treg cells as described above. Proliferation of CD45.1$^+$ T cells was assessed by FACS at D4. The % of suppression was calculated as described. For in vivo assays, $4.10^5$ naïve Tconv cells were isolated as above and transferred with or without $1.10^5$ Treg cells, to the retro-orbital sinus of 6-9 week-old RAG1$^{-/-}$ mice. Recipients were then weighed every week and euthanized when weight loss was >30%.

G. Western Blotting

Total lysates were extracted using RIPA buffer and protease inhibitors with SDS. 20 µg (micrograms) protein extracts were ran in polyacrylamide gels and transferred onto PVDF membranes. Membranes were incubated with anti-p65, c-Rel (Santa-Cruz) and GAPDH (Fitzgerald) Abs, followed HRP-coupled secondary Abs.

H. RT-qPCR and RNA-Sequencing

Total RNA was extracted using a Qiagen Rneasy Mini Kit with DNase treatment. For qPCR, RNA was reverse transcribed by Superscript III (Invitrogen). cDNAs were used for PCR with SYBR Green reagents (Quanta Biosciences, Gaithersburg, Md.) on a C1000 Touch thermal cycler (Bio Rad, Hercules, Calif.). The data was normalized to GAPDH expression. Primers sequences can be sent under request. For RNA-sequencing, libraries were prepared using an Illumina TruSeq Library Kit and sequenced by an Illumina 2500 instrument. Upon sequencing, raw FASTQ files were aligned on the mm10 genome using STAR aligner with default parameters (Dobin et al., 2013). Aligned fragments were then counted and annotated using Rsamtools v3.2 and the TxDb.Mmusculus.UCSC.mm10.knownGene' version 3.1.2 transcript database respectively. Normalized FPKM (fragments per kilobase per million mapped reads) were obtained using the robust FPKM estimate function of DeSeq2 v1.10.1 after removing the batch effect using the ComBat function of the sva package v3.18.0. Differentially expressed genes were obtained using the DESeqResults function of the same package. All p-values were adjusted for multiple comparison using the Benjamini & Hochberg FDR algorithm. For gene set enrichment analysis, the GSEA software was used, and Molecular Signature Database (MSigDB) including the ImmuneSigDB (C7 collection) (Godec et al., 2016; Subramanian et al., 2005).

I. Statistical Analyses

Experimental groups were compared statistically using the nonparametric Mann-Whitney test, or the unpaired, two-tailed Student's t-test.

Example 2

Ablation of c-Rel in Treg Cells Reduces Melanoma Growth

Figure 2:
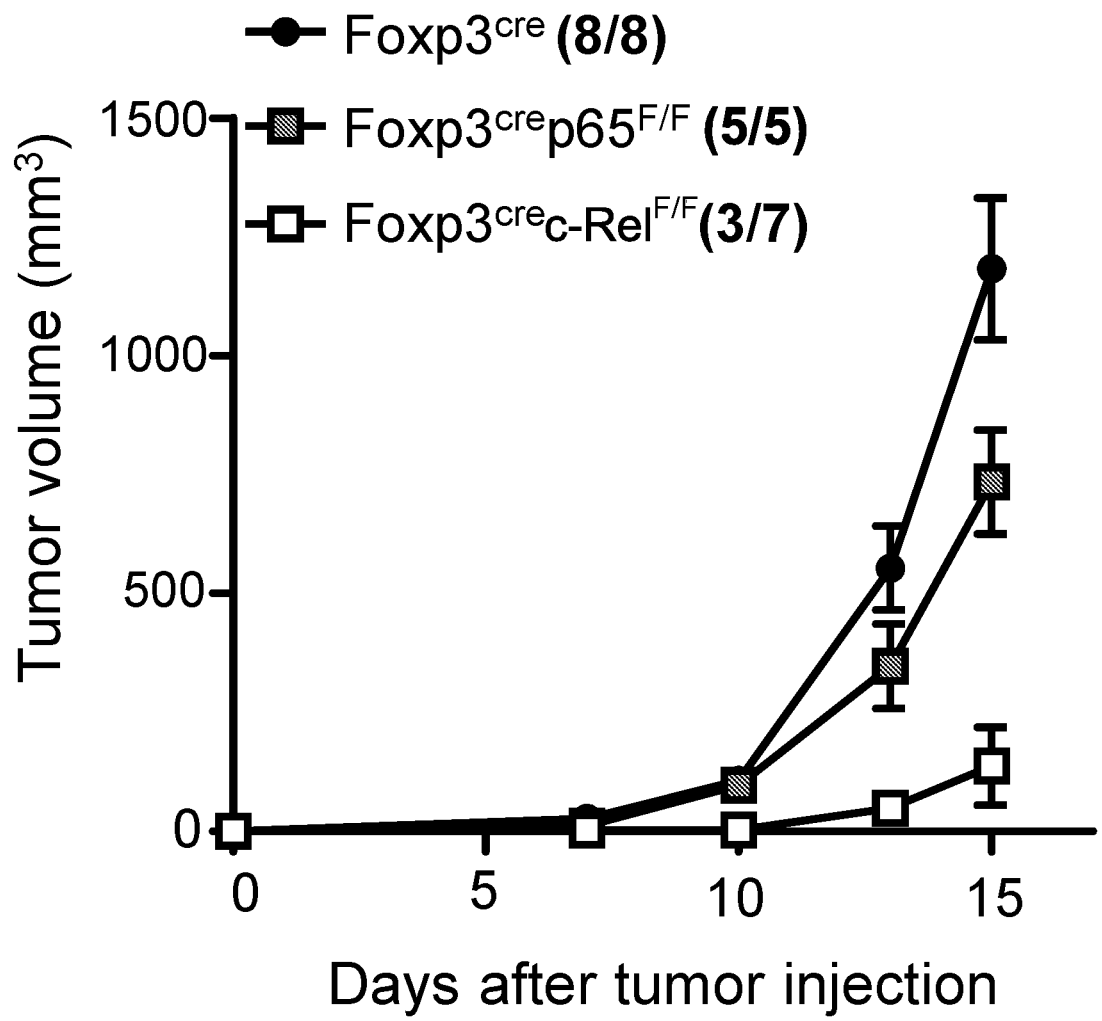
FIG. 2 is a graph showing melanoma tumor volume changes under the listed conditions where 8/8 WT mice Foxp3$^{cre}$ and 5/5 Foxp3$^{cre}$p65$^{F/F}$ mice had detectable tumor burden, whereas only 3/7 Foxp3$^{cre}$crel$^{F/F}$ mice had detectable tumor burden. Melanoma growth was reduced in mice having ablated c-Rel.

Foxp3CRE-$^{gammaFP}$p65$^{F/F}$, crel$^{FT}$ and WT littermates were injected subcutaneously with $5\times10^4$ B16F1 melanoma cells and tumor growth was monitored. See FIG. 1. A summary of 4 experiments is shown in FIG. 2. Numbers in red indicate the number of mice with detectable tumor burden at D15.

Example 3

Early Chemical Inhibition of c-Rel Reduces Melanoma Growth

Figure 4:
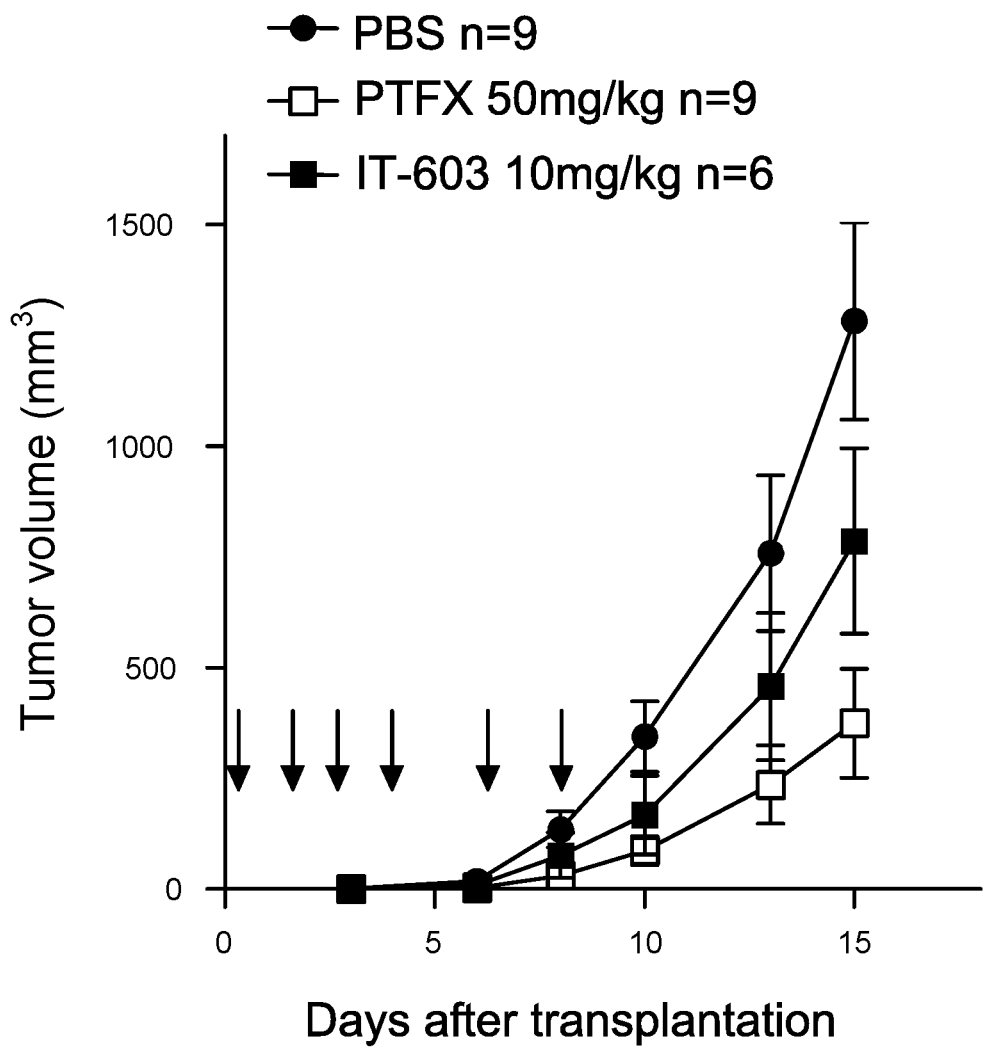
FIG. 4 is a graph showing melanoma tumor volume changes after treatment with PTXF or IT-603 where daily monitoring of tumor volume indicated that PTXF (50 mg/kg) significantly reduced growth of the tumors ($p<0.001$). IT-603 (10 mg/kg) reduced tumor growth ($p<0.08$).

C57Bl/6 WT mice were injected subcutaneously with $5\times10^4$ B16F1 melanoma cells, and then injected with either PBS (control), pentoxifylline, or IT-603 (red arrows). See FIG. 3. Tumor growth was monitored daily. A summary of the results of 3 experiments is shown in FIG. 4. ***p<0.0001.

Example 4

Figure 6:
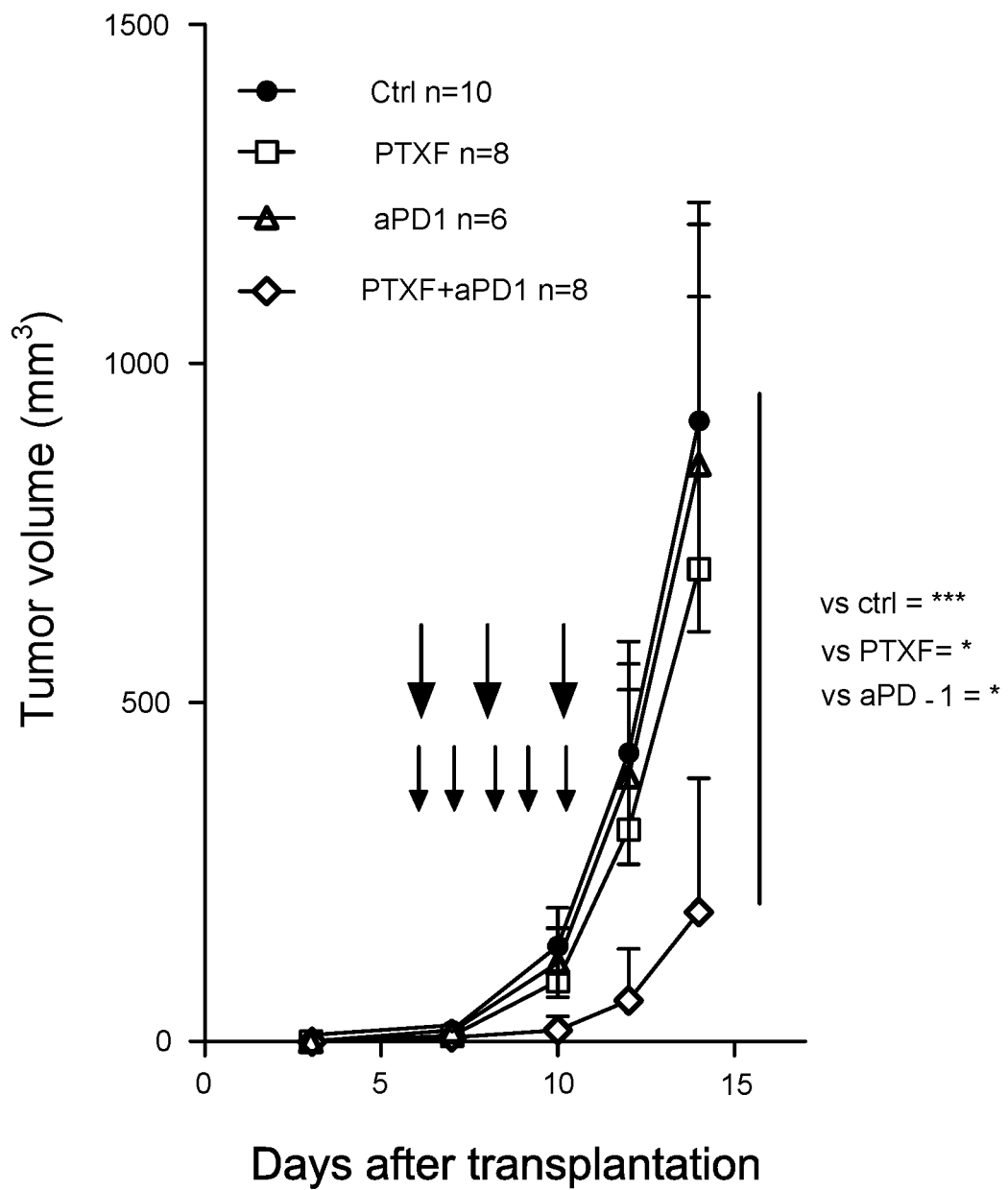
FIG. 6 is a graph showing melanoma tumor volume changes after treatment with PTXF, Apd-1, or both where mice were injected with PTXF, anti-PD1 or both. PTXF injections (50 mg/kg)) were given on days 6, 7, 8, 9, and 10, and anti-PD1 injections (250 μg per injection) were given on days 6, 8, and 10. While PTXF injections alone and anti-PD1 injections alone did not significantly reduce tumor size the combination of PTXF and antiPD-1 reduced tumor growth by more than 75%.

Synergistic Effect of PTXF and Anti-PD-1 Therapies on the Growth of Established Melanoma C57BI/6 WT mice were subcutaneously injected with $5 \times 10^4$ B16F1 melanoma cells and then injected with control IgG, PTXF (red arrows), with or without anti-PD-1 (black arrows) when the tumors were visible and palpable. See FIG. 5. Tumor growth was monitored daily. A summary of the results of 4 experiments is shown in FIG. 6. *p<0.05, ***p<0.001. While pentoxifylline injections alone did not significantly reduce tumor size in this schedule of treatment, the combination of pentoxifylline and anti-PD-1 drastically reduced tumor growth. See FIG. 6.

Example 5

Canonical NF-κB Signaling is Crucial for Treg Development

The specific roles of the canonical NF-κB subunits c-Rel and p65 in nTreg and iTreg development were explored by crossing mice with floxed c-Rel and p65 alleles with a $CD4^{cre}$ deleter strain (see FIG. 12A) and assessing the proportion and number of T cells in adult animals. Significant changes were not observed in developing CD4 and CD8 T cells in the thymus (data not shown), however, a dramatic decrease was seen in the proportion and number of $CD4^+$ $CD8^-Foxp3^-$ $CD25^+GITR^+$ Treg precursors in mice lacking canonical NF-κB subunits (FIG. 7A, FIG. 7B and FIG. 12B, FIG. 12C). There was a graded reduction of $Foxp3^+$ Treg cells upon deletion of c-Rel, p65, or both. This demonstrates both unique and partially redundant functions for canonical NF-κB subunits in the development of Treg progenitors.

Figure 7A:
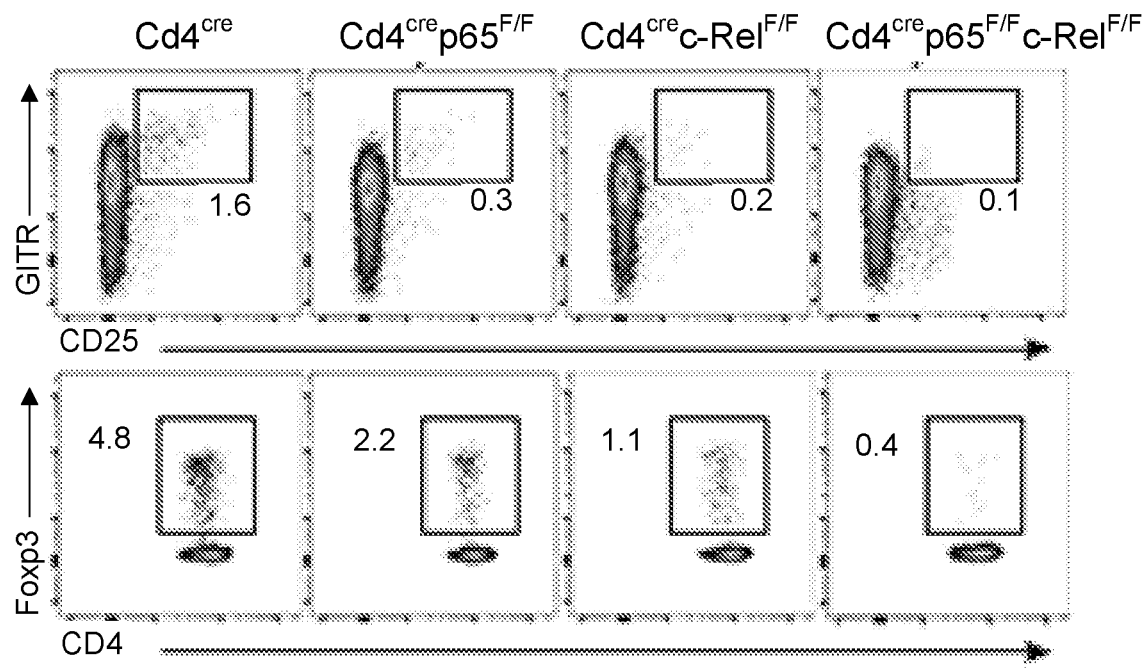
FIG. 7A-7G are graphs that illustrate discrete NF-κB subunits that control sequential steps of Treg cell development.
Figure 7B:
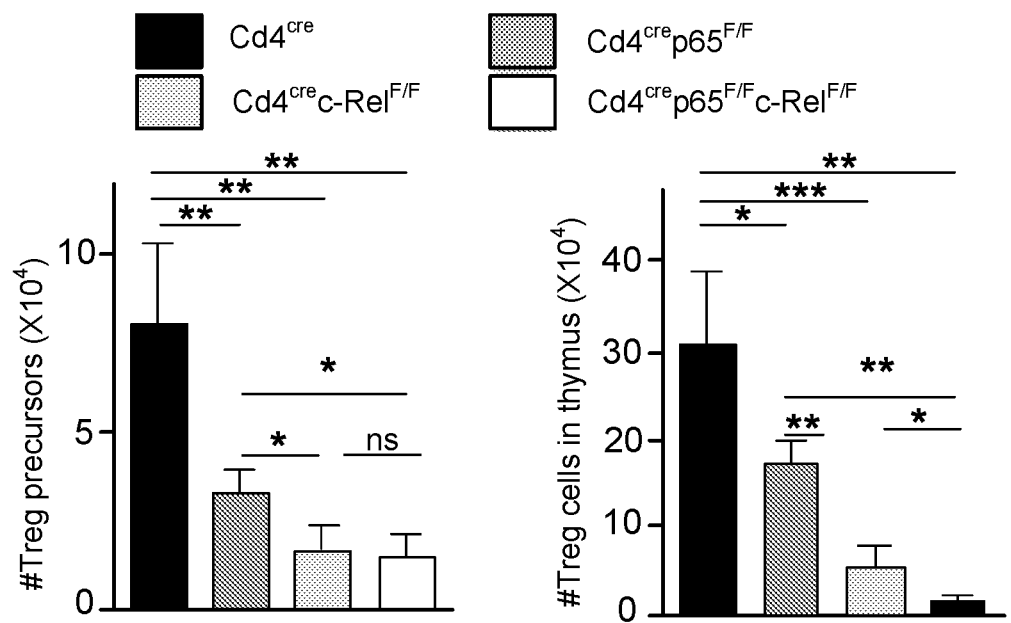
Figure 7C:
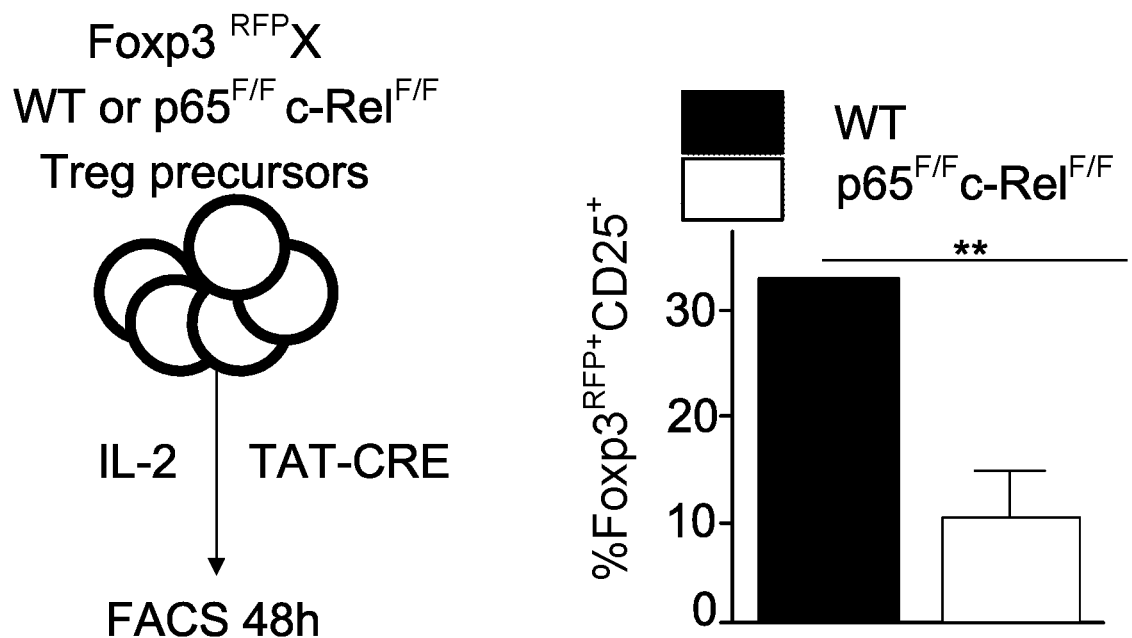
Figure 7D:
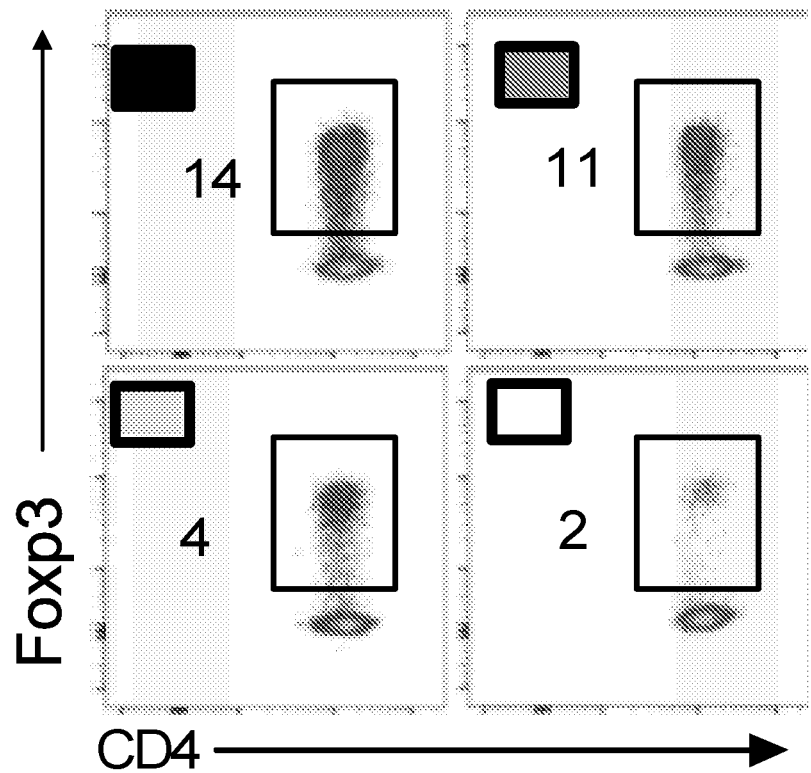
Figure 7E:
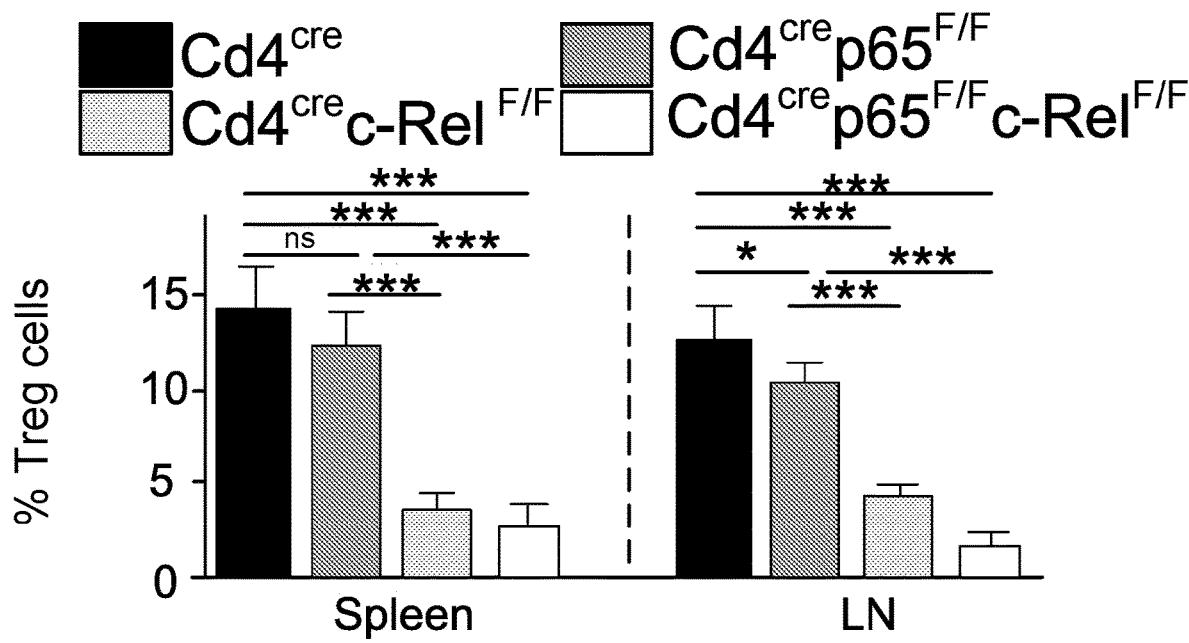
Figure 7F:
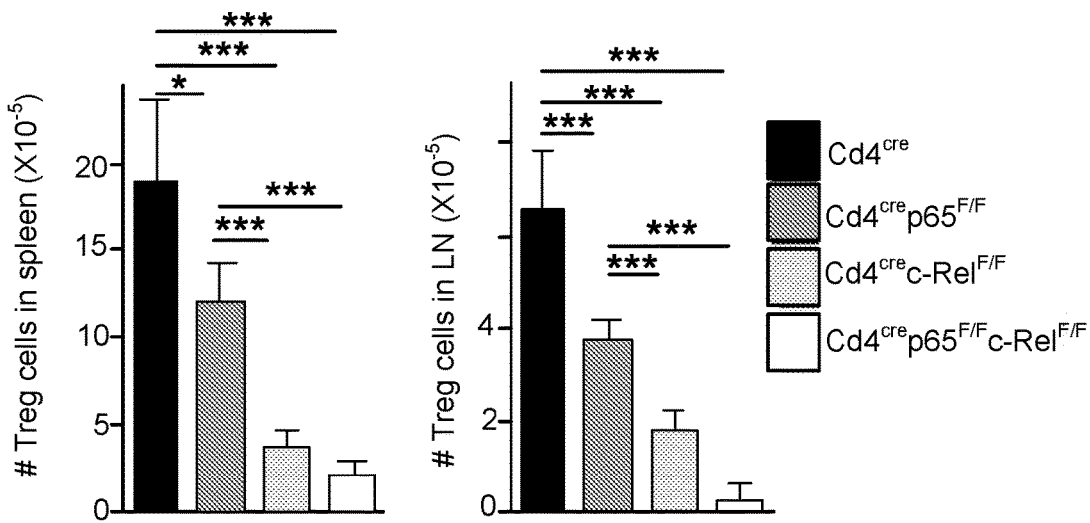

To assess whether NF-κB activation was also required for the transition from Treg progenitors to $Foxp3^+$ Treg cells, mice carrying c-Rel and p65 floxed alleles that were crossed with $Foxp3^{RFP}$ reporter mice were used. Treg progenitors were sorted using flow-cytometry, and induced the deletion of the NF-κB subunits in vitro using TAT-CRE protein (Joshi et al., 2002). Upon exposure to IL-2, wild-type (WT) progenitors gave rise to >30% $Foxp3^+$ cells (Lio and Hsieh, 2008), while a 3-fold reduction of Treg induction in cells lacking both p65 and c-Rel was observed (FIG. 7C). Hence these results suggested an intrinsic, specific and non-redundant role for canonical NF-κB subunits in consecutive steps of Treg development, in the specification of Foxp3 Treg precursors, and in the expression of Foxp3 per se. Then, the homeostasis of Treg cells in secondary lymphoid organs of all NF-κB conditional knock-out (KO) mice were examined by flow cytometry. Deletion of p65 alone led to a modest, but statistically significant, decrease in the proportion and numbers of Treg cells in both spleen and lymph nodes (LN), but not in other tissues (colon (lamina propria lymphocytes (LPL), lungs, skin, bone marrow) (FIGS. 7D-7F and FIG. 12D). As expected, mice lacking c-Rel exhibited a dramatic decrease in Treg cells in all tissues. Strikingly, this was further amplified by the deletion of both p65 and c-Rel, demonstrating a partially redundant contribution of canonical NF-κB subunits to homeostasis of peripheral Treg cells.

Figure 7G:
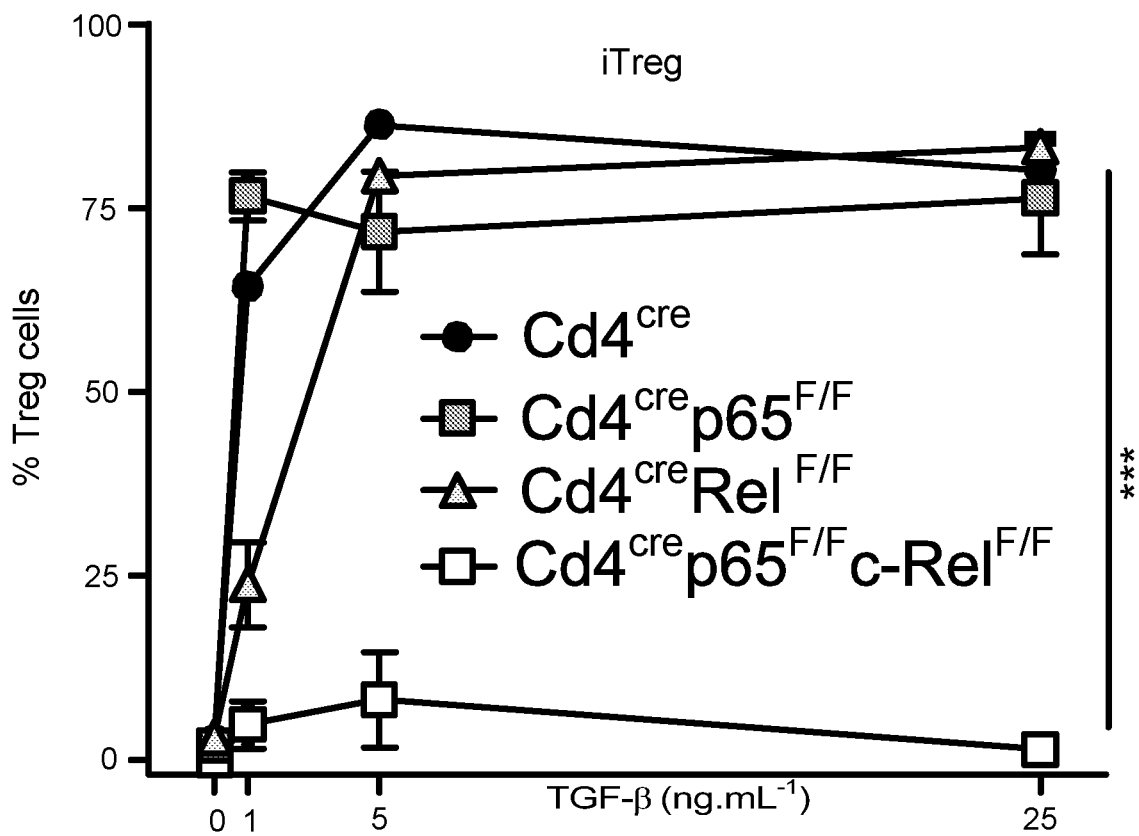

Finally, the potential role was assessed of each NF-κB subunit in iTreg induction in vitro. Upon stimulation with IL-2 and TGF-β, cells lacking p65 gave rise to normal proportions of $Foxp3^+$ cells (FIG. 7G). Naïve T cells lacking c-Rel exhibited a partial defect in iTreg induction that was rescued by increasing doses of TGF-β. However, full ablation of the NF-κB canonical pathway almost completely abolished the in vitro differentiation of naïve T cells into iTreg cells. Thus, although canonical NF-κB subunits p65 and c-Rel can partially compensate for one another, they also play discrete roles in multiple steps of both nTreg and iTreg development.

Example 6

Treg Cells Specifically Require c-Rel to Inhibit Anti-Tumor Effector Responses

Figure 8A:
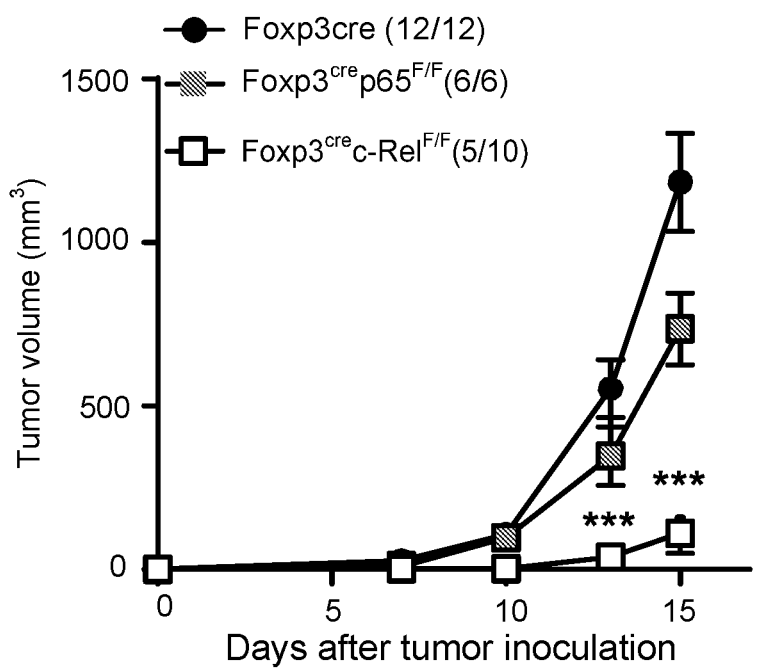

Mice lacking p65 in Treg cells developed a lethal autoimmune syndrome by the age of 6-12 weeks, while deletion of c-Rel led to mild inflammation and lymphadenopathy, but only after 20 weeks of age (see Oh et al. 2016). This was associated with distinct transcriptional programs governed by p65 and c-Rel, and suggested a more prominent role for p65 in Tregs for the maintenance of peripheral tolerance and prevention of autoimmunity. It has been proposed that prevention of tumor immunity and autoimmunity are the result of distinct Treg functions (Luo et al., 2016). However, p65 and c-Rel might also have different contributions to Treg-mediated tumor tolerance. To test this, the growth of B16F1 melanoma cells were measured in mice. As expected, exponential melanoma growth was observed in control $Foxp3^{CRE}$ transgenic animals (FIG. 8A). Surprisingly, given that the functional defects in Tregs lacking p65 (Oh et al.), melanoma tumor growth was unaltered in $Foxp3^{CRE}p65^{F/F}$ mice (FIG. 8A). In contrast, only 50% of the $Foxp3^{CRE}$c-$Rel^{F/F}$ animals exhibited detectable tumors after two weeks, and these tumors were significantly smaller than those seen in control littermates (FIG. 8A). This observation indicates that c-Rel, but not p65, is crucial for Treg homeostasis and/or function during melanoma tumor growth.

Figure 8B:
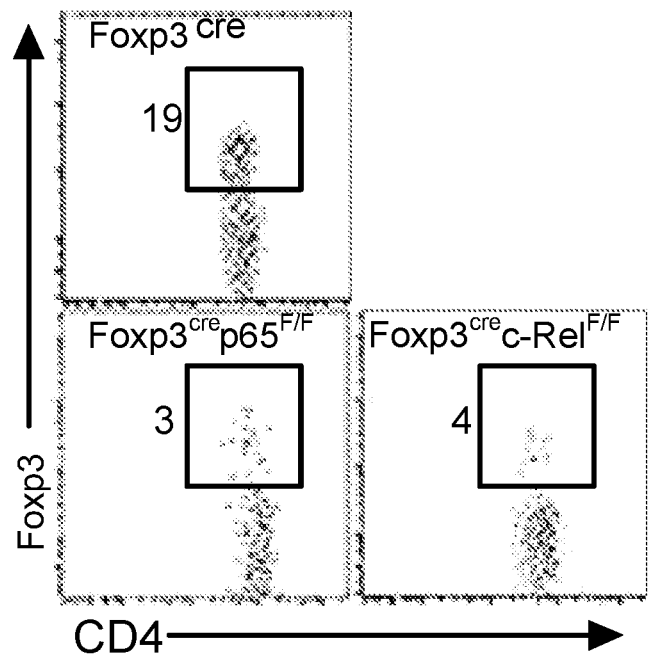
Figure 8B:
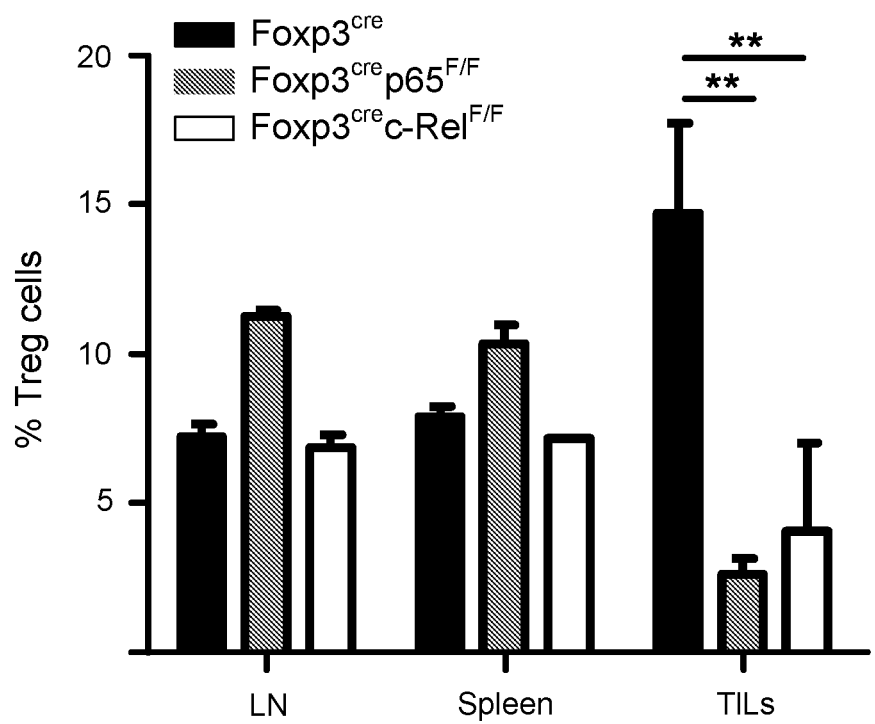

These results also provide further evidence that peripheral tolerance and tumor tolerance are mediated by separable Treg functions. To try to understand the selective role of c-Rel in response to the tumor, Treg infiltration was measured two weeks after tumor inoculation. Interestingly, an equal reduction in the proportion of Foxp3 positive tumor infiltrating lymphocytes (TILs) was observed in both c-Rel and p65 deficient animals, when compared to control littermates (FIG. 8B). Therefore, the distinct pattern of tumor growth between the two KO strains can be hypothesized to reflect functional divergence of Treg cells lacking p65 or c-Rel.

Figure 8C:
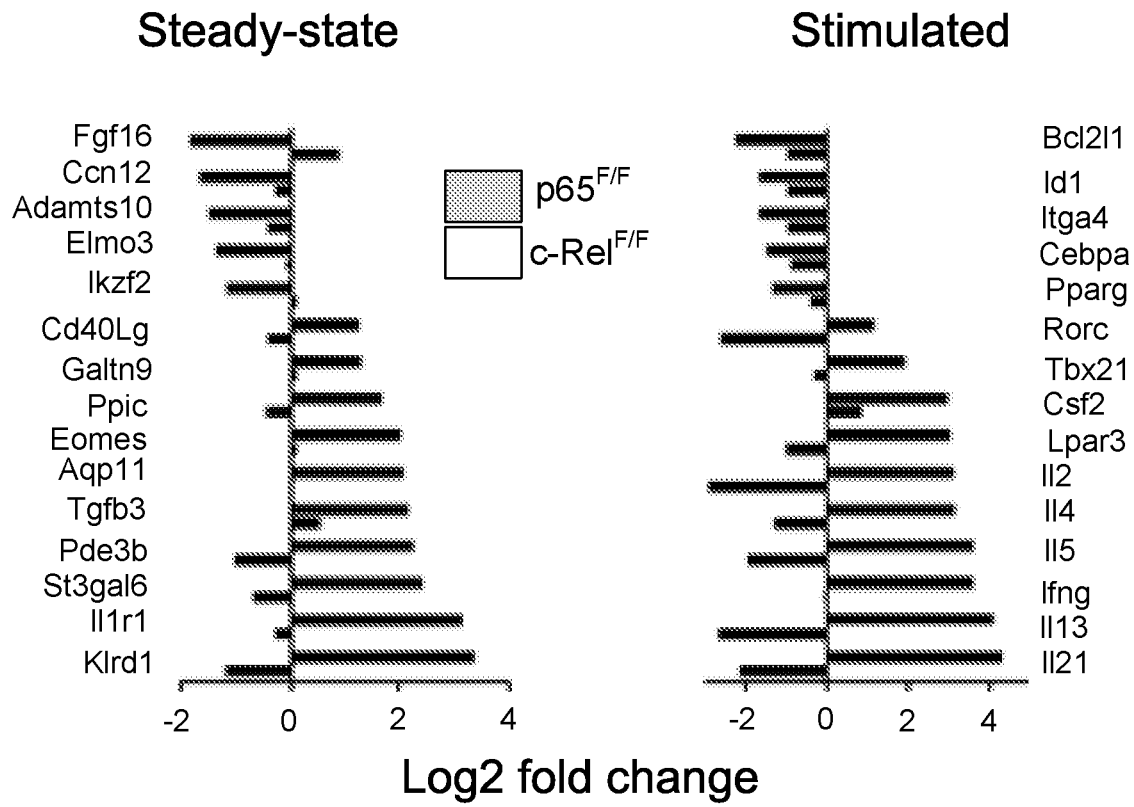
Figure 8D:
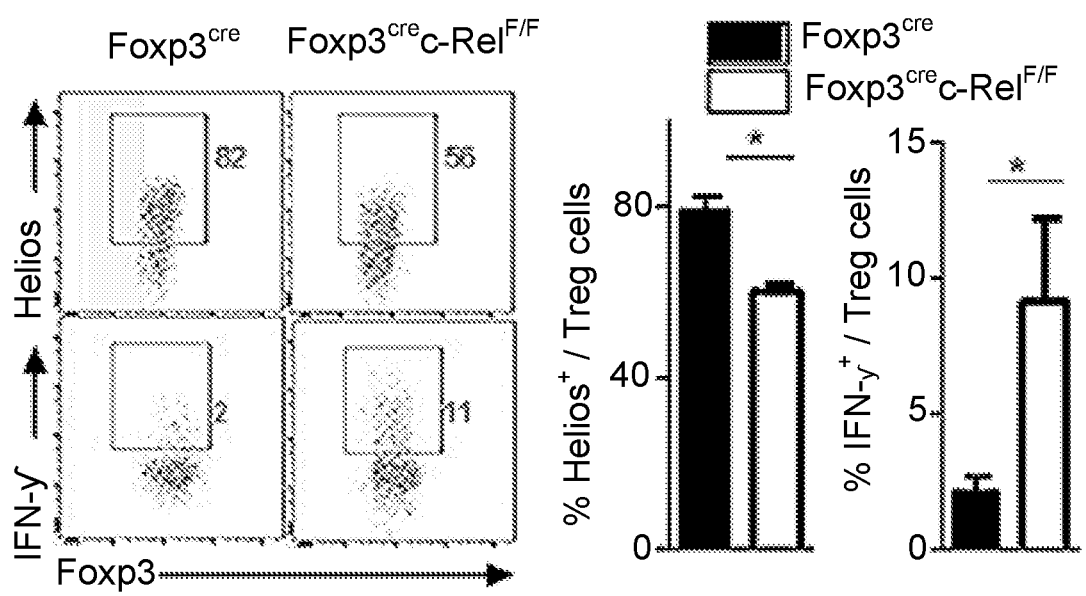
Figure 13A:
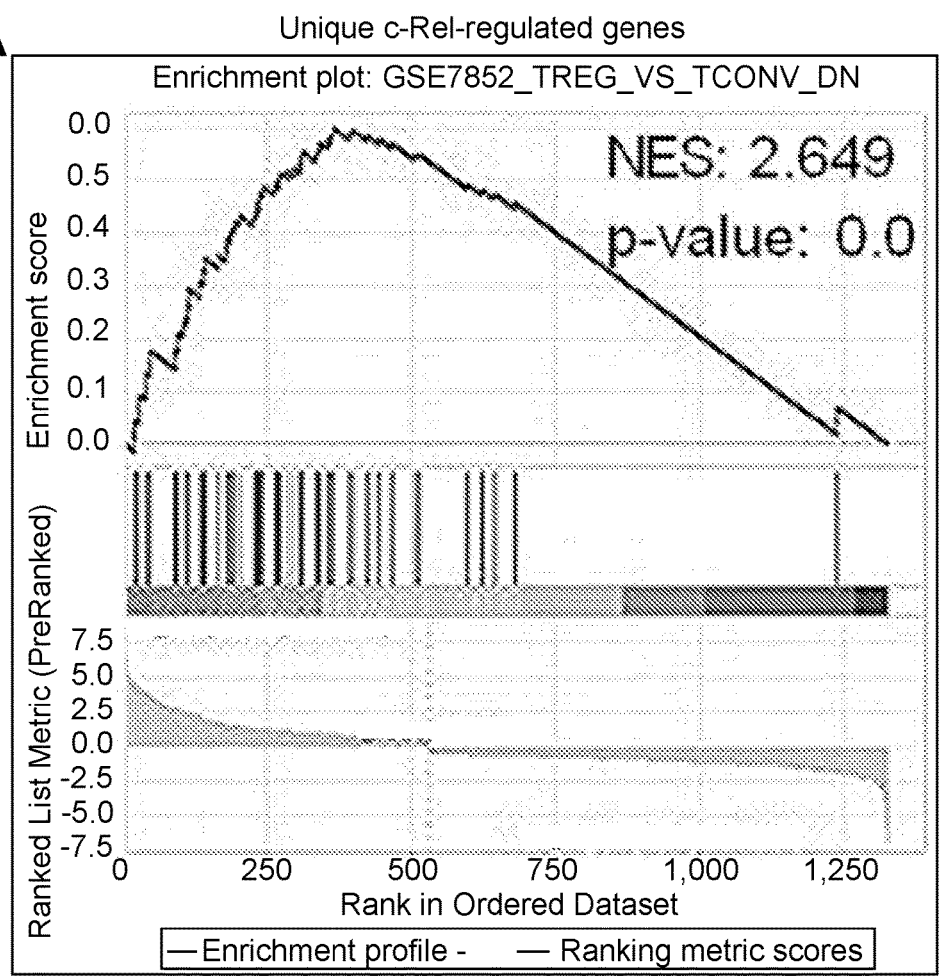
FIG. 13A-13D.

The RNA-signatures of c-Rel and p65 deficient Tregs then were analyzed compared to WT cells (see Oh et al. 2016). Strikingly, among the 688 genes whose expression was modified by the absence of c-Rel but not p65, we observed a striking loss of Treg signature genes (FIG. 13A). For example, the expression of Ikzf2 (Helios) or Ppar-γ, both of which are important regulators of Treg homeostasis, were significantly decreased; while expression of Pde3b, which is deleterious for Foxp3 stability, was increased (FIG. 8C). On the other hand, the expression of effector transcription factors and cytokines, such as Eomes, Rorc, Tbx21, Il2 or Ifng, were strongly increased in Treg lacking c-Rel (FIG. 8C). In contrast, these same effector cytokines were actually decreased in Tregs lacking p65, relative to WT Treg. The modulation of Helios and IFN-γ expression in Treg cells was also observed by flow cytometry in the spleen of Foxp3$^{CRE}$c-Rel$^{F/F}$ mice upon melanoma transplantation (FIG. 8D).

This strongly suggested that the molecular program driven by c-Rel, in contrast to p65, allowed Tregs to inhibit anti-tumor responses at early stages following tumor implantation and also suggests that Tregs lacking c-Rel can promote tumor immunity through effector cytokine production. It has been recently proposed that Treg cells displaying an activated phenotype (aTreg) were more potent inhibitors of the anti-tumor immune response, compared to resting Tregs (rTreg) (Luo et al., 2016). This differential activity could be correlated to the different genetic landscape between the two subsets. Since c-Rel is activated upon T-cell activation, c-Rel could be an essential driver of aTreg cell homeostasis and function.

Figure 8E:
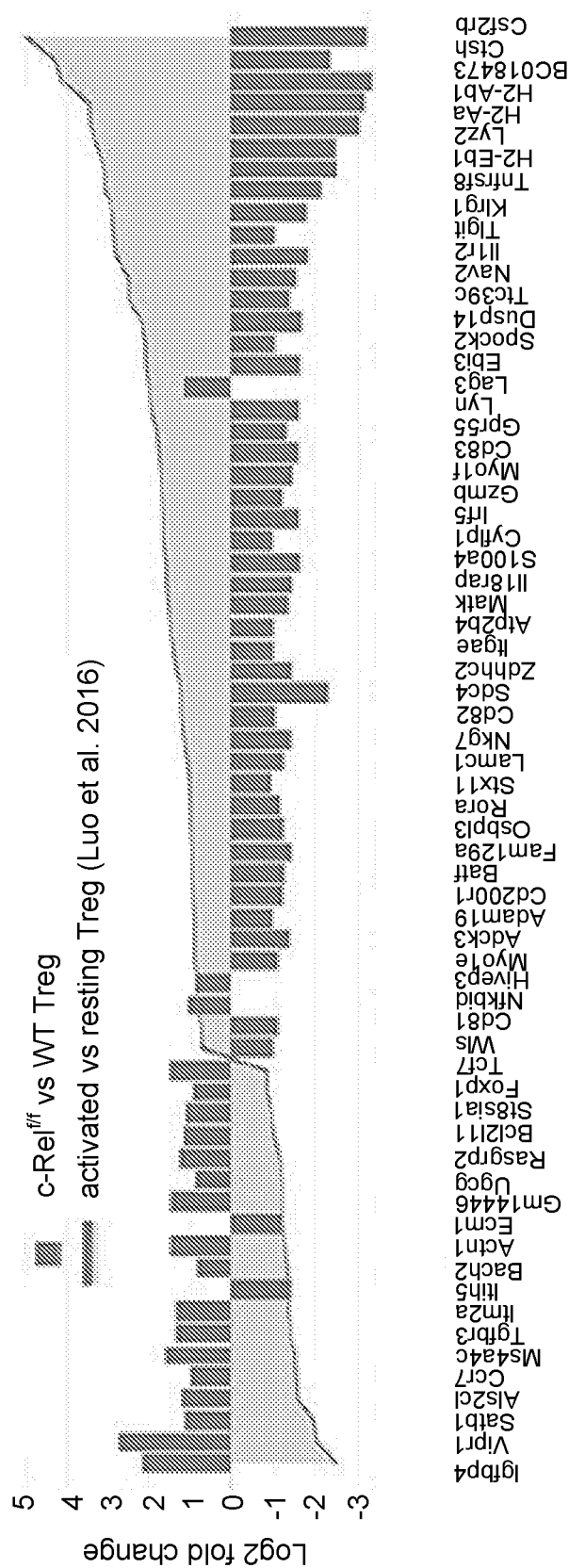

Therefore, the transcriptome of aTreg and c-Rel-deficient Treg cells were compared, particularly focusing on genes with changed expression in the c-Rel$^{-/-}$ subset. A dramatic anti-correlation was observed between the aTreg and c-Rel$^{-/-}$ Treg signatures (FIG. 8E). For example, the aTreg markers Lacm1 and Klrg1 were down-regulated in c-Rel$^{-/-}$ Treg cells, whereas the naïve T-cell-specific genes Ccr7 and Foxp1 were up-regulated. No similar correlation could be made between differential gene expression in Treg lacking p65 (Oh et al.) and aTregs (Luo et al., 2016). This suggests that NF-κB c-Rel is used specifically for the acquisition of the aTreg cell-specific transcriptome. Moreover, the loss of aTreg identity may explain the failure of Foxp3$^{CRE}$c-Rel$^{F/F}$ mice to suppress tumor immunity.

Figure 13B:
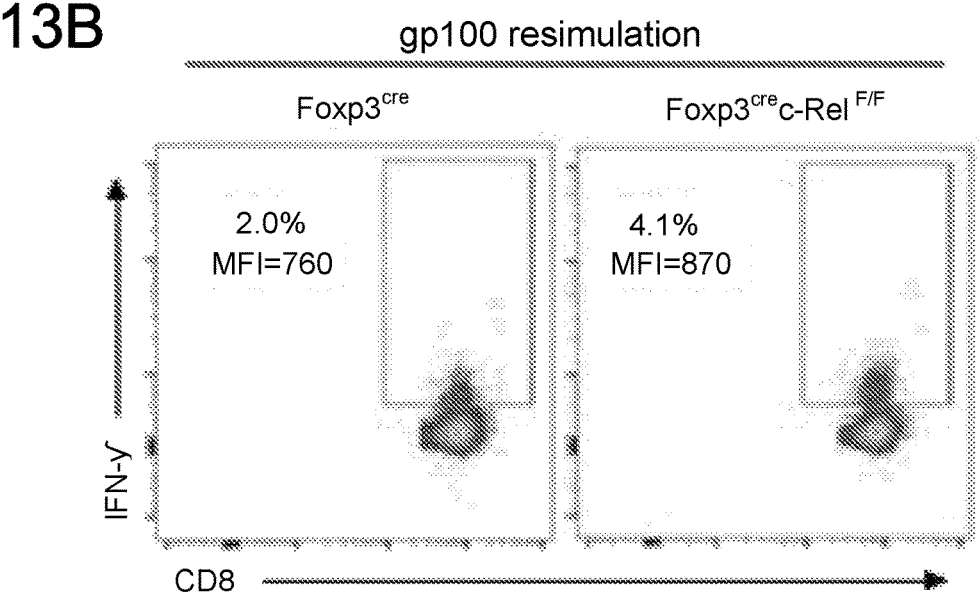
Figure 13C:
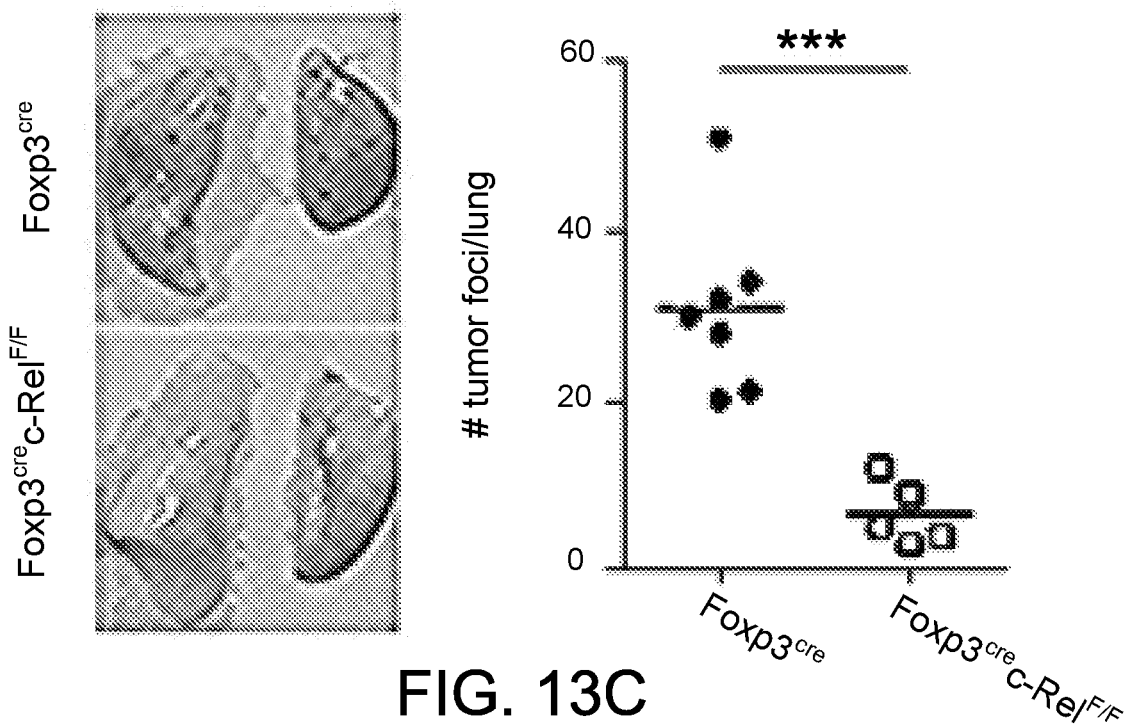
Figure 13D:
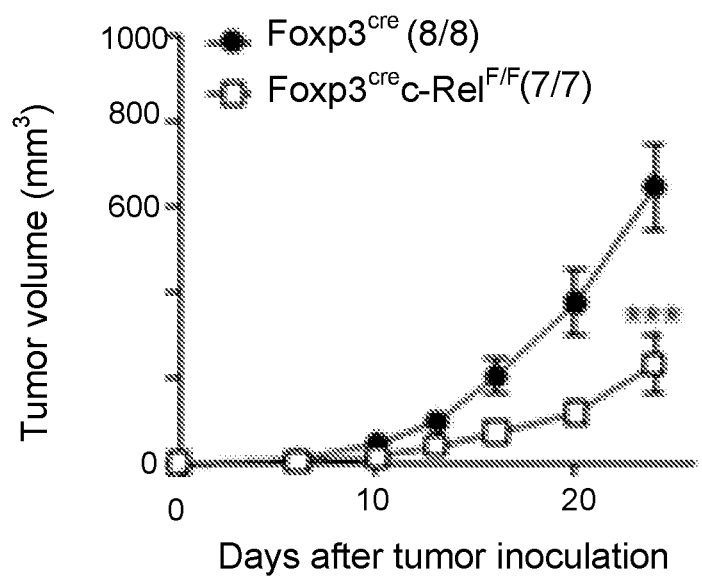

To examine anti-tumor responses in the context of Treg specific canonical NF-κB ablation, the activation status of CD4 T cells and CD8 T cells were assessed 4 days after melanoma inoculation Enhanced expression of Ki67 and CD44 was observed in splenic CD8 T cells of animals with conditional deletion of c-Rel only in Tregs compared to WT littermates (FIG. 8F, 8G). This was associated with an increased proportion of polyfunctional (IFN-γTNF$^{high}$) T cells upon polyclonal restimulation ex vivo (FIG. 8H). Similar results were obtained following gp100/p-mel tumor antigen-specific restimulation (FIG. 13B). These results suggest anti-tumor responses in mice with c-Rel deficient Tregs are due to enhanced effector T cell responses. To test the role of CD8 T cells in the impairment of melanoma growth in mice deficient for c-Rel in Tregs, CD8 T cells were depleted using a monoclonal Ab. CD8 depletion restored normal tumor growth in all the Foxp3$^{CRE}$c-Rel$^{F/F}$ animals (FIG. 8I). These findings were confirmed with 2 additional melanoma models. First, Foxp3$^{CRE}$c-Rel$^{F/F}$ and littermate control were injected intravenously with B16F10 cells. Examination of the lungs 14 days after transfer showed significantly reduced number of metastatic foci in c-Rel-deficient animals when compared to controls (FIG. 13C). Moreover, decreased growth of BRAF$^{CA}$Pten$^{-/-}$ melanomas was observed in c-Rel deficient animals (FIG. 13D). Taken together, our results demonstrate that c-Rel controls a specific genetic program in Treg cells that is required for inhibition of the anti-melanoma protective immune response mediated by CD8 T cells.

Example 7

C-Rel Inhibition Impairs Treg Identity

Although canonical NF-κB signaling is important for conventional T cell responses, the role of c-Rel in cellular immunity in vivo is not well established (Kontgen et al., 1995). Therefore, chemical inhibition of c-Rel can be hypothesized to selectively block Treg mediated tumor tolerance with minimal inhibition of anti-tumor responses. If this is the case, then such an approach would be an ideal method for targeting NF-κB signaling in the context of cancer, particularly given the lack of autoimmunity in mice lacking c-Rel in Tregs (Oh et al. 2016). Therefore, the possibility of inhibiting c-Rel chemically to impair Treg function, and promote anti-tumor responses, was investigated.

Pentoxifylline (PTXF) is a xanthine derivative that has been approved by FDA for clinical use for a wide variety of conditions over the past 30 years. PTXF has been proposed to act through multiple targets in vivo, including as a potent inhibitor of c-Rel expression and activation in T cells (Neo et al., 2014; Wang et al., 1997). Whether PTXF treatment selectively affected c-Rel in Treg cells was investigated. Stimulation of Tregs with PTXF showed a significant reduction of c-Rel protein, while levels of p65 were unchanged (FIG. 9A). Consistent with the reduction in c-Rel, significantly decreased expression of Treg markers such as Foxp3, CD25 and Helios was observed (FIG. 9B), as well as genes that were also reduced in Treg with conditional deletion of c-Rel (FIG. 2B and Oh et al.). This suggested that PTXF induced a perturbation of the Treg-associated signature that was consistent with inhibition of c-Rel.

To determine the extent to which PTXF inhibited the c-Rel-mediated transcriptional program in Tregs, the transcriptomes of control, PTXF-treated, and c-Rel deficient Tregs were compared. PTXF treatment led to a more profound alteration of the Treg transcriptome than genetic ablation of c-Rel (FIG. 9C), which was not surprising given that PTXF likely affects additional signaling pathways. The expression of c-Rel mRNA itself was unaffected by PTXF, suggesting that PTXF was affecting c-Rel through a post-translational mechanism. Gene Set Enrichment Analysis (GESA) indicated that while deletion of c-Rel mostly affected the Treg-associated gene signature, PTXF treatment also impaired the canonical T-cell activation pathway. The use of Ingenuity Pathway Analysis revealed that inhibition of the NF-κB pathway was the key feature of the PTXF-induced signature (data not shown). Moreover, a significant proportion of genes altered upon chemical and genetic inhibition of c-Rel, were shared.

Detailed examination of this set of genes highlighted a critical perturbation of Treg function and homeostasis (FIG. 9C). Indeed, we observed decreased expression of genes such as Gzmb and Tgfb1, both involved in Treg function during cancer, while Cbl-b, which directly targets Foxp3 for proteasomal degradation, was up-regulated. The genome organizer Sat1, which has been shown to promote a Tconv phenotype when expressed in Treg, also was found to be up-regulated in both c-Rel deleted, and PTXF treated, Treg cells. Moreover, known NF-κB target genes, such as Tnfrsf8, Tnaip2 or Pde3b, also displayed altered expression in both PTXF-treated and c-Rel deficient Treg cells. Interestingly, we observed only a minor overlap between the WT Treg+PTXF and Foxp3$^{CRE}$p65$^{F/F}$ transcriptomes, reinforcing the idea that PTXF affects c-Rel but not p65 (FIG. 14A). Finally, similar to the results seen when c-Rel was genetically deleted in Tregs, significant changes were observed in expression of multiple genes associated with an activated Treg cell signature, including Prdm1, Ccl20 and Il10, when Tregs were treated with PTXF (see Luo et al., 2016). Thus, PTXF induced a substantial shift in Treg transcriptional identity that is consistent with loss of c-Rel activity, and suggests a loss of suppressive function in the treated Tregs.

Treg cells lacking NF-κB c-Rel exhibit little change in function in in vitro T cell suppression assays, despite a complete inability to rescue mice in in vivo assays (Oh et al. 2016). Based on the substantial changes in the Treg transcriptome of PTXF-treated Treg cells, these cells can be hypothesized also to exhibit defects in suppressive activity. In an in vitro suppression assay, PTXF-treated Treg cells exhibited only a modest, but significant, reduction in suppression of effector T-cell proliferation when compared to mock-treated Treg cells (FIG. 9E). However, in an in vivo suppression assay, PTXF-treated Treg completely failed to prevent colitis (FIG. 9F, FIG. 9G and FIG. 14C). In both experiments, PTXF did not affect Treg survival but rather impaired their intrinsic function (FIG. 14B, FIG. 14D). Taken together, these results show that PTXF treatment impacts the homeostasis and function of Tregs similar to that seen upon deletion of c-Rel.

Example 8

C-Rel Inhibition Suppresses Tumor Growth

Figures 10A, 10B, 10C, 10D, 10E, 10F, 10G, 10H:
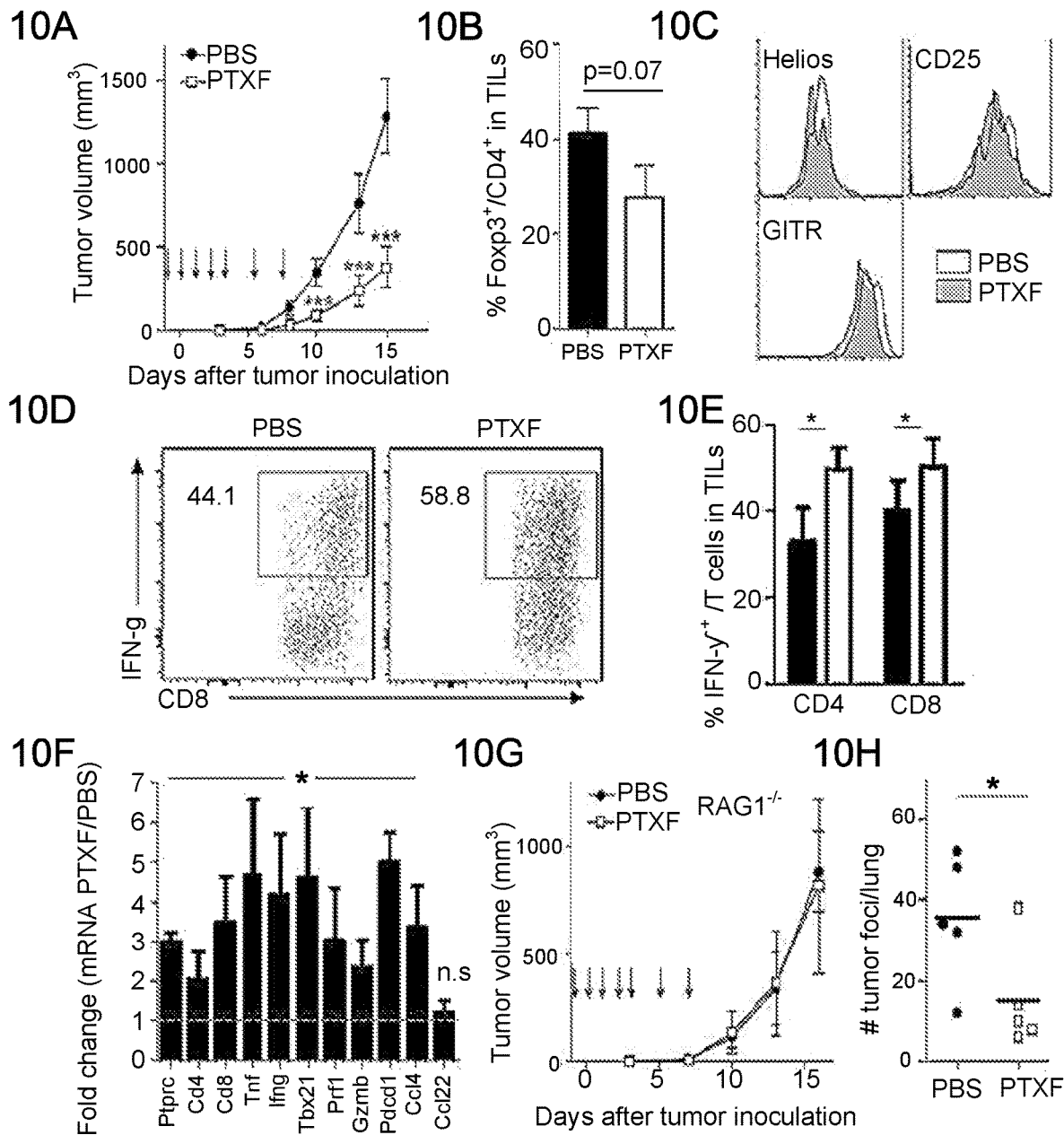
FIG. 10A-10H. illustrates c-Rel inhibition by PTXF suppresses melanoma growth.

Under the hypothesis that c-Rel, in contrast to NF-κB p65, is selectively required for Treg mediated tumor tolerance and that c-Rel is expendable for CD8-mediated anti-tumor responses, it could be predicted that administration of a c-Rel inhibiting compound like PTXF would augment anti-tumor responses similar to deletion of c-Rel in Tregs. Therefore whether PTXF administration affected tumor growth in vivo was tested. WT mice were transplanted with B16F1 melanoma cells and received daily injections of 50 mg/kg PTXF or PBS starting from day 1 after tumor cell inoculation. Consistent with previous reports (Dua et al., 2007), a significant reduction in the pace of tumor growth was observed in PTXF-treated animals compared to control animals (FIG. 10A). No observable differences in the size or composition of lymphoid tissues were detected, and no apparent adverse events were observed.

Figure 15A:
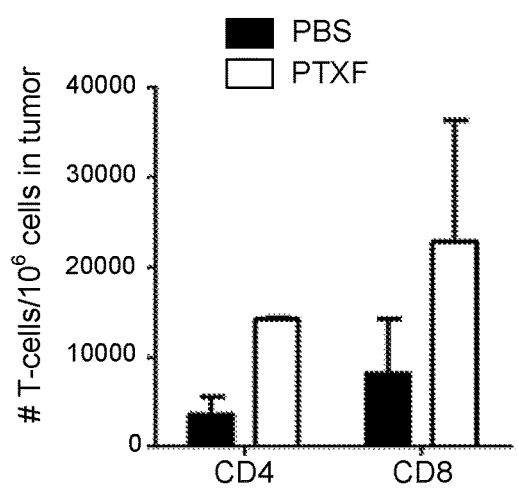
FIG. 15A-15D are graphs illustrating c-Rel inhibition by PTXF suppresses melanoma growth WT C57Bl/6J mice were transplanted sub-cutaneously with B16F1 cells and treated from D-1 to D7 with PTXF or PBS as a control. At D16, TILs were restimulated ex-vivo with PMA and ionomycin and stained for FACS. Number of TCR-α+ cells (FIG. 15A) and TCR-IFN- (FIG. 15B) cells in 1 million live cells.
Figure 15B:
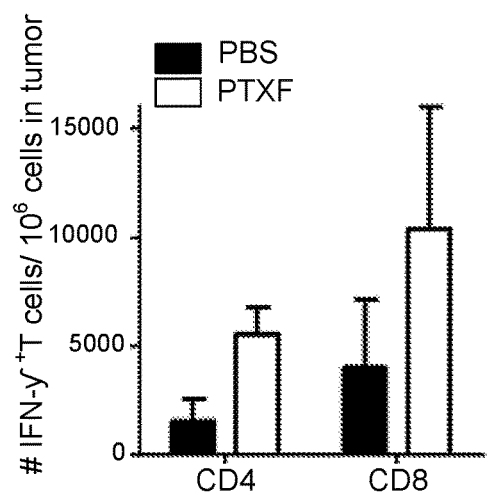
Figure 15C:
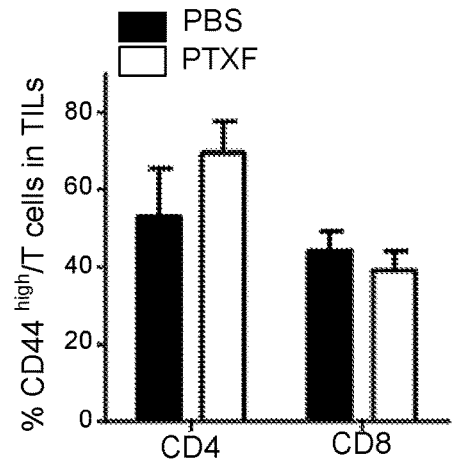
Figure 15D:
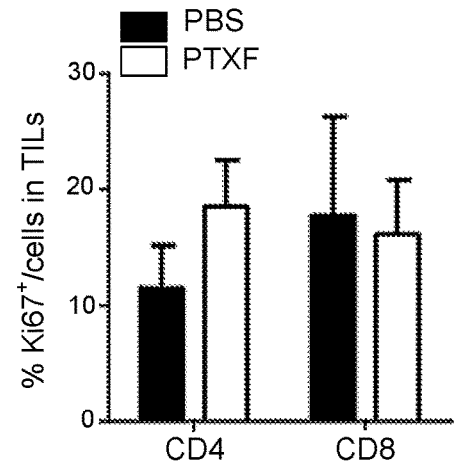

PTXF can induce tumor cell apoptosis in vitro, and inhibit the expression of adhesion molecules (Edward and MacKie, 1991; Ratheesh et al., 2007). Therefore, whether the effects of PTXF on tumor growth were tumor intrinsic or related to improved anti-tumor immune responses was studied. Analysis of tumor infiltrates at D16 revealed a decrease in the proportion of Treg cells, as well as an altered phenotype of these cells (FIG. 10B, FIG. 10C). Additionally, there was an increase in infiltration of total T cells, as well as IFN-γ-producing CD4 and CD8 T-cells into the tumors (TILs) (see FIG. 10D, FIG. 10E, FIG. 15A and FIG. 15B). CD44 and Ki67 expression also were increased on CD4+ Tconv TILs of PTXF-treated animals (FIG. 15C and FIG. 15D). Moreover, qPCR analysis of total tumors revealed a dramatic enhancement of the inflammatory response, including increased expression of activated T-cell markers and cytokines (FIG. 10F). Only a minor and non-significant increase (1.2x) was observed of the Ccl22 mRNA, that codes for a chemokine involved in the recruitment of Treg cells to the tumor micro-environment through CCR4 (Nishikawa and Sakaguchi, 2010). This suggests that immune cells, especially T cells, can mediate the protective effect of PTXF on melanoma growth.

To test whether there were direct effects on tumor growth independent of the changes in T cell responses, immunodeficient RAG1$^{-/-}$ mice were transplanted with B16F1 cells and the mice were treated with PBS or PTXF. In this immunodeficient background, PTXF had no effect on tumor growth (FIG. 10G). Therefore, lymphocytes are required for the anti-tumor effects of PTXF. Finally, these results were confirmed in the settings of B16F10 metastatic melanoma. Again, in immunocompetent mice, early PTXF treatment significantly decreased the total number of metastatic foci in lungs (FIG. 10H). These results demonstrate that either genetic deletion of c-Rel in Tregs, or administration of a c-Rel inhibitor, can inhibit Treg function and prevent Treg-mediated tumor tolerance.

Example 9

PTXF Treatment Synergizes with Checkpoint Blockade Therapies to Inhibit Melanoma Growth The emergence of checkpoint-blockade as curative therapies for cancer is a major step forward in the field of oncology. For example, antibody-mediated blockade of the PD-1/PD-L1 pathway is emerged as an important new therapy for melanomas and other solid tumors Immunotherapy targeting checkpoints are believed to work by relieving exhaustion of CD8 T– cells, thereby allowing the re-activation of anti-tumor effector cells (Francisco et al., 2010). However anti-PD-1 monotherapy is ineffective for treatment of many tumors including in animal models, e.g. in B16-induced melanoma in mice (Chen et al., 2015). Regulatory T cells promote tumor tolerance, and inhibition of Treg activity can, in part, account for the improved efficacy of the combined blockade of PD-1 and CTLA-4 (Curran et al., 2010). Whether targeting of Treg cells with PTXF could potentiate the beneficial effect of PD-1-blockade was investigated.

Figures 11A, 11B, 11C, 11D, 11E, 11F, 11G:
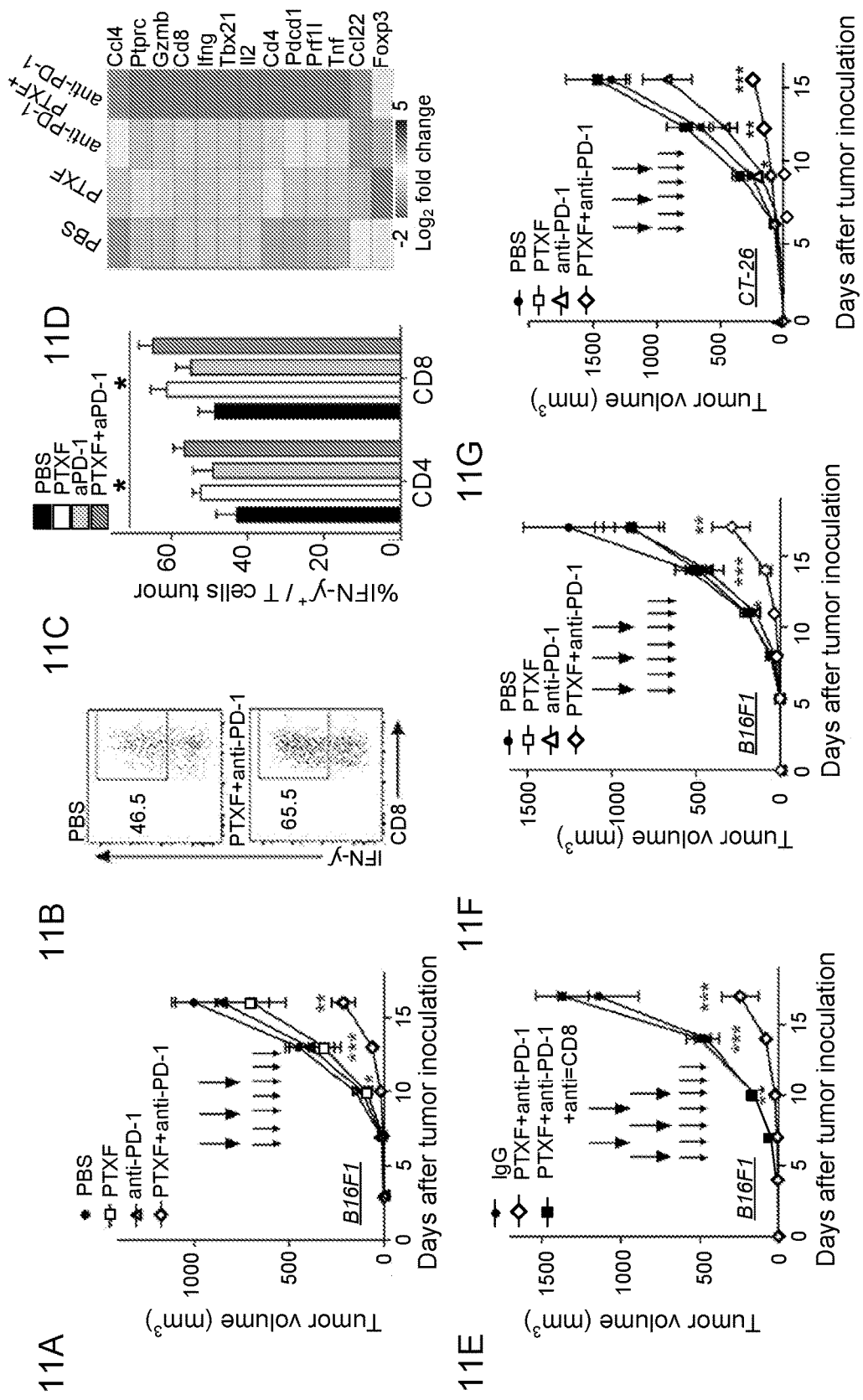
FIG. 11A-11G are graphs illustrating PTXF and PD-1-blockade synergize to reduce growth of established melanoma.
Figures 12A, 12B, 12C, 12D:
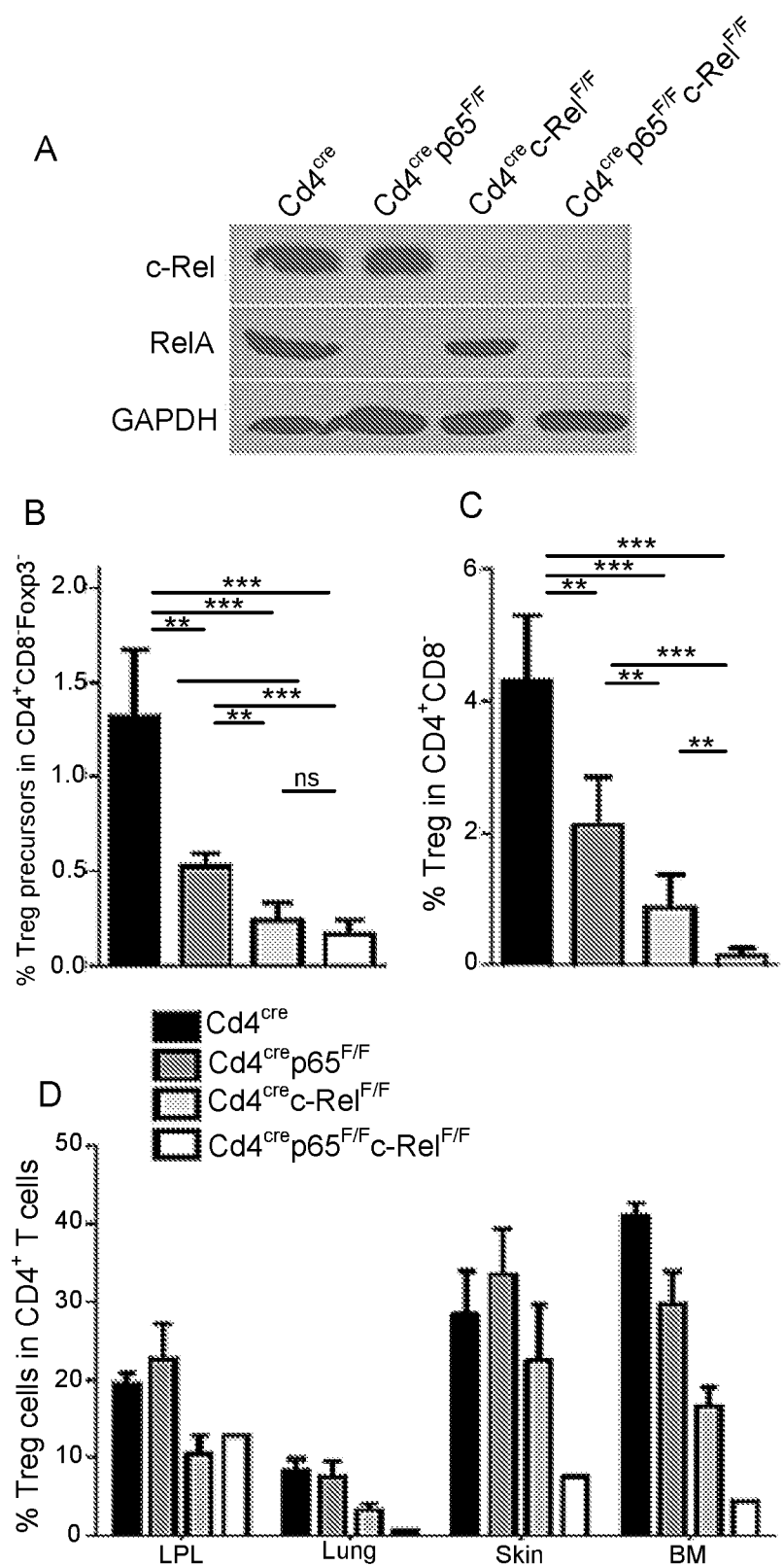
FIG. 12A-12D illustrate discrete NF-B subunits control sequential steps of Treg cell development.
Figure 16A:
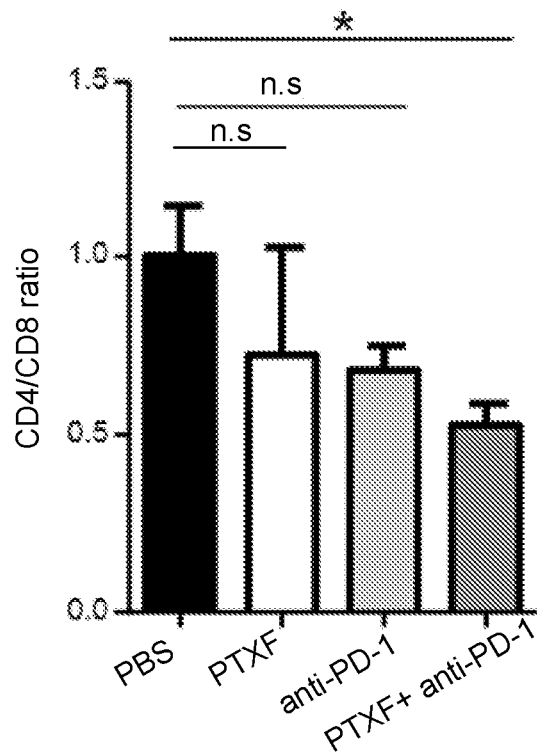
FIG. 16A and 16B illustrate PTXF and PD-1-blockade synergize to reduce growth of established melanoma WT C57Bl/6J mice were transplanted subcutaneously with B16F1 cells and treated from D6 with PTXF or anti-PD-1 mAb or PBS. At D16, TILs were stained for FACS.
Figure 16B:
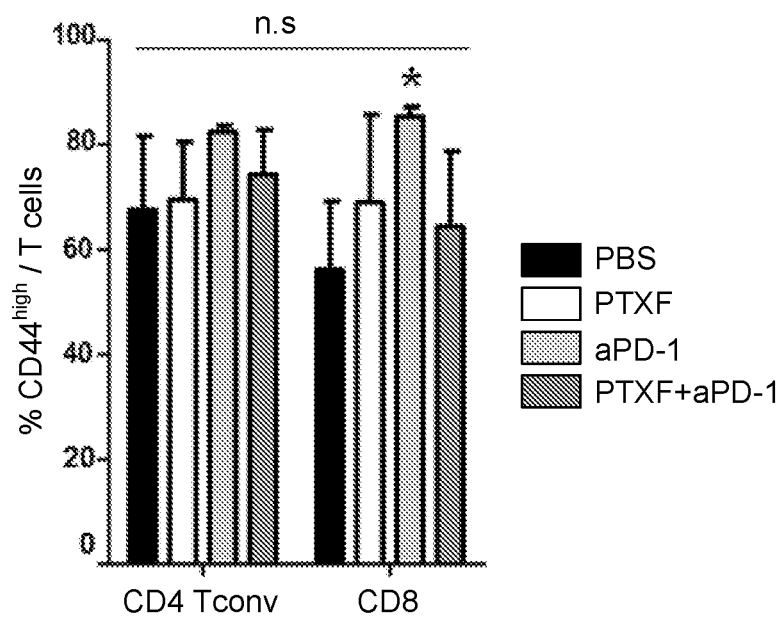
Figure 17A:
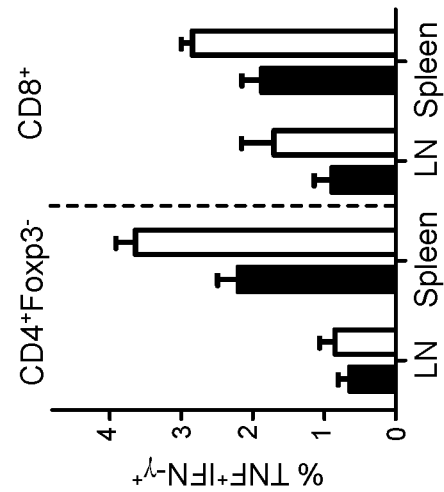
FIG. 17A-17D are schematics illustrating the role of NF-κB in Treg during melanoma development.
Figure 17B:
Figure 17C:
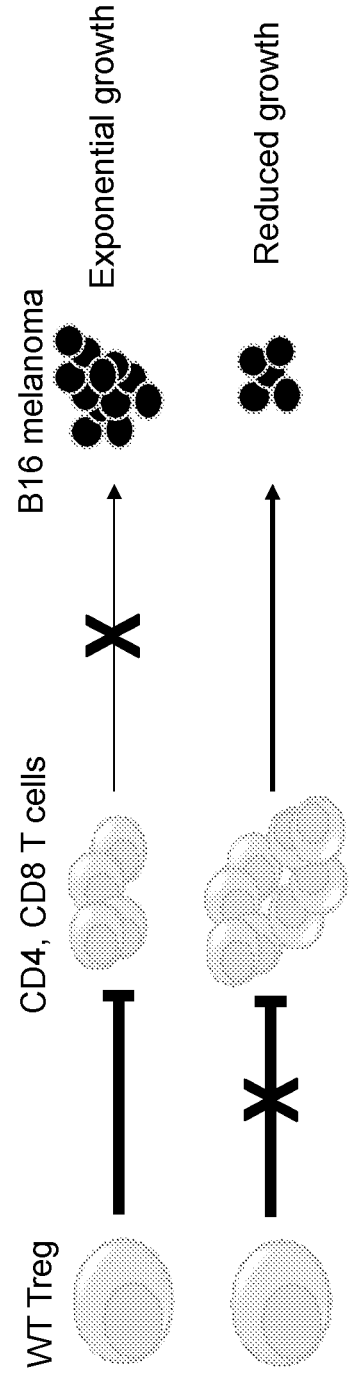
Figure 17D:
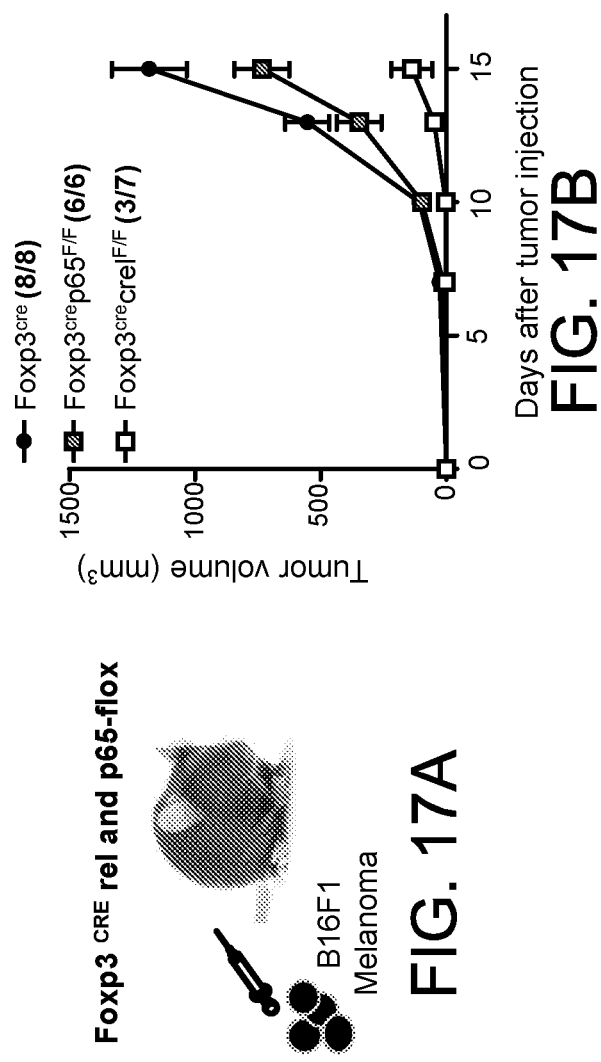

Mice were first transplanted with B16F1 melanoma cells, and treated with vehicle, PTXF and/or anti-PD-1 mAb when the tumors reached a volume >2 mm$^3$ (usually D5 to D6). PTXF or anti-PD-1 monotherapies did not change the growth curves when compared to PBS controls. However the combination of PTXF and anti-PD-1 produced a significant flattening in growth curves (FIG. 11A). Co-administration of PTXF and anti-PD-1 drove increased expression of IFN-γ by CD4 and CD8 T cells (FIG. 11B and FIG. 11C). Moreover, inversion of the CD4/CD8 ratio upon treatment was observed, while CD44 expression remained almost unchanged (FIG. 16A and FIG. 16B).

RNA expression analysis demonstrated a cumulative effect of PTXF and anti-PD-1 treatments, with inflammatory cytokines and activation markers being strongly upregulated in the tumors of mice receiving the combination therapy (FIG. 11D). Also, the total expression of both Foxp3 and Ccl22 were significantly reduced upon combination therapy, while the expression of Ccl4, which is known to recruit effector T cells to the tumor, was augmented. Finally, CD8 depletion with a mAb fully restored tumor growth in PTXF+ anti-PD-1 treated animals (FIG. 11E) demonstrating a requirement for CD8 T cells for improved tumor clearance. Next, we confirmed that these findings were not dependent on one particular anti-PD-1 mAb, by blocking the ligand of PD-1, PD-L1. Even though monotherapy with PTXF or anti-PD-L1 did not affect tumor growth, the combination of both PTXF and anti-PDL1 had a synergistic effect by decreasing and delaying melanoma growth (FIG. 11F).

Finally, the effect of PTXF/anti-PD-1 therapy was assessed in a different genetic background. Balb/c mice were transplanted with CT-26 colon carcinoma, and subsequently treated with PTXF alone and suboptimal doses of anti-PD-1 (since high doses of anti-PD-1 induced a significant decrease in CT-26 growth, data not shown). Again, only the combination of both drugs led to a significant reduction of tumor growth (FIG. 11G).

REFERENCES

All references cited herein throughout the specification and/or listed below are hereby incorporated by reference in their entirety.
1. Algul, H., Treiber, M., Lesina, M., Nakhai, H., Saur, D., Geisler, F., Pfeifer, A., Paxian, S., and Schmid, R. M. (2007). Pancreas-specific RelA/p65 truncation increases susceptibility of acini to inflammation-associated cell death following cerulein pancreatitis. J Clin. Invest. 117, 1490-1501.
2. Baumgartner, J. M., Gonzalez, R., Lewis, K. D., Robinson, W. A., Richter, D. A., Palmer, B. E., Wilson, C. C., and McCarter, M. D. (2009). Increased survival from stage IV melanoma associated with fewer regulatory T Cells. The Journal of surgical research 154, 13-20.
Beg, A. A., Sha, W. C., Bronson, R. T., Ghosh, S., and Baltimore, D. (1995). Embryonic lethality and liver degeneration in mice lacking the RelA component of NF-kappa B. Nature 376, 167-170.
3. Bertrand, A., Kostine, M., Barnetche, T., Truchetet, M. E., and Schaeverbeke, T. (2015). Immune related adverse events associated with anti-CTLA-4 antibodies: systematic review and meta-analysis. BMC medicine 13, 211.
4. Boissonnas, A., Scholer-Dahirel, A., Simon-Blancal, V., Pace, L., Valet, F., Kissenpfennig, A., Sparwasser, T., Malissen, B., Fetler, L., and Amigorena, S. (2010). Foxp3+ T cells induce perforin-dependent dendritic cell death in tumor-draining lymph nodes. Immunity 32, 266-278.
5. Bravo-Cuellar, A., Hernandez-Flores, G., Lerma-Diaz, J. M., Dominguez-Rodriguez, J. R., Jave-Suarez, L. F., De Celis-Carrillo, R., Aguilar-Lemarroy, A., Gomez-Lomeli, P., and Ortiz-Lazareno, P. C. (2013). Pentoxifylline and the proteasome inhibitor MG132 induce apoptosis in human leukemia U937 cells through a decrease in the expression of Bcl-2 and Bcl-XL and phosphorylation of p65. Journal of biomedical science 20, 13.
6. Callahan, M. K., Postow, M. A., and Wolchok, J. D. (2014). CTLA-4 and PD-1 Pathway Blockade: Combinations in the Clinic. Frontiers in oncology 4, 385.
7. Chang, C. L., Hsu, Y. T., Wu, C. C., Yang, Y. C., Wang, C., Wu, T. C., and Hung, C. F. (2012). Immune mechanism of the antitumor effects generated by bortezomib. J Immunol. 189, 3209-3220.
8. Chariot, A. (2009). The NF-kappaB-independent functions of IKK subunits in immunity and cancer. Trends in cell biology 19, 404-413.
9. Chen, S., Lee, L. F., Fisher, T. S., Jessen, B., Elliott, M., Evering, W., Logronio, K., Tu, G. H., Tsaparikos, K., Li, X., et al. (2015). Combination of 4-1BB agonist and PD-1 antagonist promotes antitumor effector/memory CD8 T cells in a poorly immunogenic tumor model. Cancer immunology research 3, 149-160.
10. Curran, M. A., Montalvo, W., Yagita, H., and Allison, J. P. (2010). PD-1 and CTLA-4 combination blockade expands infiltrating T cells and reduces regulatory T and myeloid cells within B16 melanoma tumors. Proc. Natl. Acad. Sci. USA 107, 4275-4280.
11. Deenick, E. K., Elford, A. R., Pellegrini, M., Hall, H., Mak, T. W., and Ohashi, P. S. (2010). c-Rel but not NF-kappaB1 is important for T regulatory cell development. Eur J Immunol 40, 677-681.
12. DiDonato, J. A., Mercurio, F., and Karin, M. (2012). NF-kappaB and the link between inflammation and cancer. Immunological reviews 246, 379-400.
13. Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.
14. Donkor, M. K., Sarkar, A., Savage, P. A., Franklin, R. A., Johnson, L. K., Jungbluth, A. A., Allison, J. P., and Li, M. O. (2011). T cell surveillance of oncogene-induced prostate cancer is impeded by T cell-derived TGF-beta1 cytokine. Immunity 35, 123-134.
15. Dua, P., Ingle, A., and Gude, R. P. (2007). Suramin augments the antitumor and antimetastatic activity of pentoxifylline in B16F10 melanoma. International journal of cancer Journal international du cancer 121, 1600-1608.
16. Dunn, G. P., Bruce, A. T., Ikeda, H., Old, L. J., and Schreiber, R. D. (2002). Cancer immunoediting: from immunosurveillance to tumor escape. Nat Immunol 3, 991-998.
17. Edward, M., and MacKie, R. M. (1991). Pentoxifylline enhances lung colonization and alters cell adhesion and glycosaminoglycan synthesis by metastatic B16 melanoma cells. International journal of cancer Journal international du cancer 49, 711-716.
18. Fingert, H. J., Pu, A. T., Chen, Z. Y., Googe, P. B., Alley, M. C., and Pardee, A. B. (1988). In vivo and in vitro enhanced antitumor effects by pentoxifylline in human cancer cells treated with thiotepa. Cancer research 48, 4375-4381.
19. Francisco, L. M., Sage, P. T., and Sharpe, A. H. (2010). The PD-1 pathway in tolerance and autoimmunity. Immunological reviews 236, 219-242.
20. Gavin, M. A., Rasmussen, J. P., Fontenot, J. D., Vasta, V., Manganiello, V. C., Beavo, J. A., and Rudensky, A. Y. (2007). Foxp3-dependent programme of regulatory T-cell differentiation. Nature 445, 771-775.
21. Godec, J., Tan, Y., Liberzon, A., Tamayo, P., Bhattacharya, S., Butte, A. J., Mesirov, J. P., and Haining, W. N. (2016). Compendium of Immune Signatures Identifies Conserved and Species-Specific Biology in Response to Inflammation. Immunity 44, 194-206.
22. Greten, F. R., Arkan, M. C., Bollrath, J., Hsu, L. C., Goode, J., Miething, C., Goktuna, S. I., Neuenhahn, M., Fierer, J., Paxian, S., et al. (2007). NF-kappaB is a negative regulator of IL-1beta secretion as revealed by genetic and pharmacological inhibition of IKKbeta. Cell 130, 918-931.
23. Grigoriadis, G., Vasanthakumar, A., Banerjee, A., Grumont, R., Overall, S., Gleeson, P., Shannon, F., and Gerondakis, S. (2011). c-Rel controls multiple discrete steps in the thymic development of Foxp3+ CD4 regulatory T cells. PloS one 6, e26851.
24. Hecht, M., Muller, M., Lohmann-Matthes, M. L., and Emmendorffer, A. (1995). In vitro and in vivo effects of pentoxifylline on macrophages and lymphocytes derived from autoimmune MRL-lpr/lpr mice. J Leukoc Biol 57, 242-249.
25. Heise, N., De Silva, N. S., Silva, K., Carette, A., Simonetti, G., Pasparakis, M., and Klein, U. (2014). Germinal Center B-Cell Maintenance and Differentiation Are Controlled by Distinct NF-kappaB Transcription Factor Subunits. J Exp Med 211, 2103-2118.
26. Isomura, I., Palmer, S., Grumont, R. J., Bunting, K., Hoyne, G., Wilkinson, N., Banerjee, A., Proietto, A., Gugasyan, R., Wu, L., et al. (2009). c-Rel is required for the development of thymic Foxp3+ CD4 regulatory T cells. J Exp Med 206, 3001-3014.
27. Jana, S., Jailwala, P., Haribhai, D., Waukau, J., Glisic, S., Grossman, W., Mishra, M., Wen, R., Wang, D., Williams, C. B., et al. (2009). The role of NF-kappaB and Smad3 in TGF-beta-mediated Foxp3 expression. Eur J Immunol 39, 2571-2583.
28. Jandus, C., Bioley, G., Speiser, D. E., and Romero, P. (2008). Selective accumulation of differentiated FOXP3 (+) CD4(+) T cells in metastatic tumor lesions from melanoma patients compared to peripheral blood. Cancer immunology, immunotherapy: CII 57, 1795-1805.
29. Jimenez, J. L., Punzon, C., Navarro, J., Munoz-Fernandez, M. A., and Fresno, M. (2001). Phosphodiesterase 4 inhibitors prevent cytokine secretion by T lymphocytes by inhibiting nuclear factor-kappaB and nuclear factor of activated T cells activation. The Journal of pharmacology and experimental therapeutics 299, 753-759.
30. Joshi, S. K., Hashimoto, K., and Koni, P. A. (2002). Induced DNA recombination by Cre recombinase protein transduction. Genesis 33, 48-54.
31 Kim, H. J., Hawke, N., and Baldwin, A. S. (2006). NF-kappaB and IKK as therapeutic targets in cancer. Cell death and differentiation 13, 738-747.
32. Kleffel, S., Posch, C., Barthel, S. R., Mueller, H., Schlapbach, C., Guenova, E., Elco, C. P., Lee, N., Juneja, V. R., Zhan, Q., et al. (2015). Melanoma Cell-Intrinsic PD-1 Receptor Functions Promote Tumor Growth. Cell 162, 1242-1256.
33. Kontgen, F., Grumont, R. J., Strasser, A., Metcalf, D., Li, R., Tarlinton, D., and Gerondakis, S. (1995). Mice lacking the c-rel proto-oncogene exhibit defects in lymphocyte proliferation, humoral immunity, and interleukin-2 expression. Genes Dev 9, 1965-1977.
34. Laurat, E., Poirier, B., Tupin, E., Caligiuri, G., Hansson, G. K., Bariety, J., and Nicoletti, A. (2001). In vivo downregulation of T helper cell 1 immune responses reduces atherogenesis in apolipoprotein E-knockout mice. Circulation 104, 197-202.
35. Leach, D. R., Krummel, M. F., and Allison, J. P. (1996) Enhancement of antitumor immunity by CTLA-4 blockade. Science 271, 1734-1736.
36. Lio, C. W., and Hsieh, C. S. (2008). A two-step process for thymic regulatory T cell development. Immunity 28, 100-111.
37. Long, M., Park, S. G., Strickland, I., Hayden, M. S., and Ghosh, S. (2009). Nuclear factor-kappaB modulates regulatory T cell development by directly regulating expression of Foxp3 transcription factor. Immunity 31, 921-931.
38. Luo, C. T., Liao, W., Dadi, S., Toure, A., and Li, M. O. (2016). Graded Foxo1 activity in Treg cells differentiates tumour immunity from spontaneous autoimmunity. Nature 529, 532-536.
39. Molinero, L. L., Miller, M. L., Evaristo, C., and Alegre, M. L. (2011). High TCR stimuli prevent induced regulatory T cell differentiation in a NF-kappaB-dependent manner J Immunol 186, 4609-4617.
40. Molinero, L. L., Yang, J., Gajewski, T., Abraham, C., Farrar, M. A., and Alegre, M. L. (2009). CARMA1 controls an early checkpoint in the thymic development of FoxP3+ regulatory T cells. J Immunol 182, 6736-6743.
41. Moran, A. E., Holzapfel, K. L., Xing, Y., Cunningham, N. R., Maltzman, J. S., Punt, J., and Hogquist, K. A. (2011). T cell receptor signal strength in Treg and iNKT cell development demonstrated by a novel fluorescent reporter mouse. J Exp Med 208, 1279-1289.
42. Moreau, P., Richardson, P. G., Cavo, M., Orlowski, R. Z., San Miguel, J. F., Palumbo, A., and Harousseau, J. L. (2012). Proteasome inhibitors in multiple myeloma: 10 years later. Blood 120, 947-959.
43. Mulligan, G., Mitsiades, C., Bryant, B., Zhan, F., Chng, W. J., Roels, S., Koenig, E., Fergus, A., Huang, Y., Richardson, P., et al. (2007). Gene expression profiling and correlation with outcome in clinical trials of the proteasome inhibitor bortezomib. Blood 109, 3177-3188.
44. Nakagawa, H., Sido, J. M., Reyes, E. E., Kiers, V., Cantor, H., and Kim, H. J. (2016). Instability of Helios-deficient Tregs is associated with conversion to a T-effector phenotype and enhanced antitumor immunity. Proc Natl Acad Sci USA.
45. Neo, W. H., Lim, J. F., Grumont, R., Gerondakis, S., and Su, I. H. (2014). c-Rel regulates Ezh2 expression in activated lymphocytes and malignant lymphoid cells. The Journal of biological chemistry 289, 31693-31707.
46. Nishikawa, H., and Sakaguchi, S. (2010). Regulatory T cells in tumor immunity. International journal of cancer Journal international du cancer 127, 759-767.
47. Oeckinghaus, A., Hayden, M. S., and Ghosh, S. (2011). Crosstalk in NF-kappaB signaling pathways. Nat Immunol 12, 695-708.
48. Oh. H., Grinerg-Bleyer, Y., Wang, J., Park, S.-G., Bhatt, D., Heise, N., Schmid, R., Hayden, M. S., Klein, U., Rabadan, R., and Ghosh. S. (2016) An NF-κB-dependent, lineage specific transcriptional program regulates Treg identity and function. (under review)
49. Onizuka, S., Tawara, I., Shimizu, J., Sakaguchi, S., Fujita, T., and Nakayama, E. (1999). Tumor rejection by in vivo administration of anti-CD25 (interleukin-2 receptor alpha) monoclonal antibody. Cancer research 59, 3128-3133.
50. Orlowski, R. Z., and Kuhn, D. J. (2008). Proteasome inhibitors in cancer therapy: lessons from the first decade. Clinical cancer research: an official journal of the American Association for Cancer Research 14, 1649-1657.
51. Ouyang, Z., Wu, H., Li, L., Luo, Y., Li, X., and Huang, G. (2016). Regulatory T cells in the immunotherapy of melanoma. Tumour biology: the journal of the International Society for Oncodevelopmental Biology and Medicine 37, 77-85.
52. Ratheesh, A., Ingle, A., and Gude, R. P. (2007). Pentoxifylline modulates cell surface integrin expression and integrin mediated adhesion of B16F10 cells to extracellular matrix components. Cancer biology & therapy 6, 1743-1752.
53. Ruan, Q., Kameswaran, V., Tone, Y., Li, L., Liou, H. C., Greene, M. I., Tone, M., and Chen, Y. H. (2009). Development of Foxp3(+) regulatory t cells is driven by the c-Rel enhanceosome. Immunity 31, 932-940.
54. Samstein, R. M., Arvey, A., Josefowicz, S. Z., Peng, X., Reynolds, A., Sandstrom, R., Neph, S., Sabo, P., Kim, J. M., Liao, W., et al. (2012). Foxp3 exploits a pre-existent enhancer landscape for regulatory T cell lineage specification. Cell 151, 153-166.
55. Schuster, M., Glauben, R., Plaza-Sirvent, C., Schreiber, L., Annemann, M., Floess, S., Kuhl, A. A., Clayton, L. K., Sparwasser, T., Schulze-Osthoff, K., et al. (2012). IkappaB(NS) protein mediates regulatory T cell development via induction of the Foxp3 transcription factor. Immunity 37, 998-1008.
56. Sharma, P., and Allison, J. P. (2015). Immune checkpoint targeting in cancer therapy: toward combination strategies with curative potential. Cell 161, 205-214.

57. Shono et al., "507 Targeted Therapy of B Lymphoma with a Direct Inhibitor of the NF-kB Subunit c-Rel." 56th ASH Annual Meeting and Exposition, Dec. 6-9, 2014, Session 625, Abstract.
58. Soligo, M., Camperio, C., Caristi, S., Scotta, C., Del Porto, P., Costanzo, A., Mantel, P. Y., Schmidt-Weber, C. B., and Piccolella, E. (2011). CD28 costimulation regulates FOXP3 in a RelA/NF-kappaB-dependent mechanism. European journal of immunology 41, 503-513.
59. Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc Natl Acad Sci USA 102, 15545-15550.
60. Sugiyama, D., Nishikawa, H., Maeda, Y., Nishioka, M., Tanemura, A., Katayama, I., Ezoe, S., Kanakura, Y., Sato, E., Fukumori, Y., et al. (2013). Anti-CCR4 mAb selectively depletes effector-type FoxP3+CD4+ regulatory T cells, evoking antitumor immune responses in humans. Proc Natl Acad Sci USA 110, 17945-17950.
61. Suresh, R., Vig, M., Bhatia, S., Goodspeed, E. P., John, B., Kandpal, U., Srivastava, S., George, A., Sen, R., Bal, V., et al. (2002). Pentoxifylline functions as an adjuvant in vivo to enhance T cell immune responses by inhibiting activation-induced death. J Immunol 169, 4262-4272.
62. Tang, Q., and Bluestone, J. A. (2008). The Foxp3+ regulatory T cell: a jack of all trades, master of regulation. Nat Immunol 9, 239-244.
63. Vignali, D. A., Collison, L. W., and Workman, C. J. (2008). How regulatory T cells work. Nat Rev Immunol 8, 523-532.
64. Visekruna, A., Huber, M., Hellhund, A., Bothur, E., Reinhard, K., Bollig, N., Schmidt, N., Joeris, T., Lohoff, M., and Steinhoff, U. c-Rel is crucial for the induction of Foxp3(+) regulatory CD4(+) T cells but not T(H)17 cells. Eur J Immunol 40, 671-676.
65. Wang, W., Tam, W. F., Hughes, C. C., Rath, S., and Sen, R. (1997). c-Rel is a target of pentoxifylline-mediated inhibition of T lymphocyte activation. Immunity 6, 165-174.
66. Xue, W., Meylan, E., Oliver, T. G., Feldser, D. M., Winslow, M. M., Bronson, R., and Jacks, T. (2011). Response and resistance to NF-kappaB inhibitors in mouse models of lung adenocarcinoma. Cancer discovery 1, 236-247.
67. Zhao, Y., Guo, H., Qiao, G., Zucker, M., Langdon, W. Y., and Zhang, J. (2015). E3 Ubiquitin Ligase Cbl-b Regulates Thymic-Derived CD4+CD25+ Regulatory T Cell Development by Targeting Foxp3 for Ubiquitination. J Immunol 194, 1639-1645.

What is claimed is:

1. A method of treating a PD-1-resistant cancer comprising administering to a subject in need thereof a therapeutically effective amount of a c-Rel inhibitor and a therapeutically effective amount of a PD-1 inhibitor.

2. The method of claim 1, wherein the c-Rel inhibitor is a member selected from the group consisting of pentoxifylline, a pentoxifylline analog, dehydroxymethylepoxyquinomicin (DHMEQ), pyrimidinetrione and its derivatives including IT-603, and any combination thereof.

3. The method of claim 2, wherein the pentoxifylline analog is selected from the group consisting of lisofylline, torbafylline, propentafylline, A81-138, IT-603, dyfylline, doxofylline, theophylline, isobutyl methylxanthine (IBMX), caffeine, and any combination thereof.

4. The method of claim 3, wherein the pentoxifylline analog is selected from the group consisting of torbafylline, propentafylline, A81-138, and any combination thereof.

5. The method of claim 1, wherein the PD-1 inhibitor is an anti-PD-1 antibody or an anti-PD-L1 antibody or a biologically active fragment or variant thereof.

6. The method of claim 5, wherein the anti-PD-1 antibody or the anti-PD-L1 antibody is a humanized monoclonal antibody.

7. The method of claim 1, wherein the effective amount of the c-Rel inhibitor is about 0.1 mg/day to about 5 g/day and the amount of the PD-1 inhibitor is about 0.1 mg/day to about 5 g/day.

8. The method of claim 7, wherein the effective amount of the c-Rel inhibitor is about 400 mg/day to about 1800 mg/day and the amount of the PD-1 inhibitor is about 1 mg/kg/2 weeks to about 10 mg/kg/week.

9. The method of claim 1, wherein the effective amount of the c-Rel inhibitor is about 0.5 mg/day to about 2500 mg/day, about 1 mg/day to about 750 mg/day, about 5 mg to about 500 mg/day or about 10 mg/day to about 100 mg/day.

10. The method of claim 1, wherein the effective amount of the c-Rel inhibitor is about 2500 mg/day, about 2400 mg/day, about 2000 mg/day, about 1800 mg/day, about 1600 mg/day, about 1200 mg/day, about 1000 mg/day, about 800 mg/day, about 600 mg/day, about 500 mg/day, about 400 mg/day, about 200 mg/day, about 100 mg/day, about 50 mg/day, about 25 mg/day, about 10 mg/day, about 5 mg/day, or between about 1 mg/day and 200 mg/day.

11. The method of claim 1, wherein the effective amount of the PD-1 inhibitor is about 1 mg/kg, about 2 mg/kg, about 5 mg/kg, about 7.5 mg/kg, or about 10 mg/kg, administered every week or every two weeks.

12. The method of claim 1, wherein the effective amount of the PD-1 inhibitor is about 200 micrograms, given every 2-3 days by injection.

13. The method of claim 1, wherein the PD-1-resistant cancer is a melanoma.

14. The method of claim 13, wherein the melanoma is a B16F1 melanoma or a B16F10 metastatic melanoma.

15. The method of claim 1, wherein the PD-1-resistant cancer is selected from the group consisting of melanoma, metastatic melanoma, ovarian cancer, fibrosarcoma, breast cancer, lung cancer, non-small cell carcinoma, and colon cancer.

16. The method of claim 1, wherein the PD-1-resistant cancer is selected from the group consisting of B16F1 (melanoma), B16F10 (metastatic melanoma), Id8 (ovarian cancer), Sa1N (fibrosarcoma), TUBO (mammary carcinoma), TC-1 (lung sarcoma), $BRaf^{CA}$, $Pten^{loxP}$, Tyr::Cre-$ER^{T2}$ (melanoma), MC38 (colon carcinoma), and CT-26 (colon carcinoma).

* * * * *

UNITED STATES PATENT AND TRADEMARK OFFICE
CERTIFICATE OF CORRECTION

PATENT NO. : 10,954,300 B2
APPLICATION NO. : 15/763995
DATED : March 23, 2021
INVENTOR(S) : Ghosh et al.

Page 1 of 1

It is certified that error appears in the above-identified patent and that said Letters Patent is hereby corrected as shown below:

On the Title Page

Item (71), please replace the applicant with the following:
THE TRUSTEES OF COLUMBIA UNIVERSITY IN THE CITY OF NEW YORK. New York, NY (US)

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*